(12) United States Patent
Sharon et al.

(10) Patent No.: US 11,291,515 B2
(45) Date of Patent: Apr. 5, 2022

(54) DEVICE FOR AUTOMATICALLY INSERTING AND MANIPULATING A MEDICAL TOOL INTO AND WITHIN A BODILY LUMEN

(71) Applicants: Microbot Medical Ltd., Yokneam Illit (IL); Technion Research & Development Foundation Limited, Haifa (IL)

(72) Inventors: Simon Sharon, Zichron Yaacov (IL); Idan Boader, Carmiel (IL); Evgeny Kofman, Kiriat-Motzkin (IL); Moshe Shoham, Haifa (IL); Eran Cohen, Kiryat-Tivon (IL); Eyal Morag, Tel Aviv (IL)

(73) Assignees: Microbot Medical Ltd., Yokneam Illit (IL); Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 17/233,774

(22) Filed: Apr. 19, 2021

(65) Prior Publication Data

US 2021/0236217 A1 Aug. 5, 2021

Related U.S. Application Data

(63) Continuation-in-part of application No. PCT/IL2020/051226, filed on Nov. 26, 2020.
(Continued)

(51) Int. Cl.
*A61B 34/00* (2016.01)
*A61M 25/01* (2006.01)
(Continued)

(52) U.S. Cl.
CPC .............. *A61B 34/70* (2016.02); *A61B 34/30* (2016.02); *A61B 34/35* (2016.02); *A61B 34/37* (2016.02);
(Continued)

(58) Field of Classification Search
CPC ........ A61M 25/0113; A61M 25/09041; A61M 25/0905; A61B 34/30; A61B 2034/301
See application file for complete search history.

(56) References Cited

U.S. PATENT DOCUMENTS 5,571,072 A 11/1996 Kronner
6,358,199 B1 3/2002 Pauker et al.
(Continued)

FOREIGN PATENT DOCUMENTS

CN 103599585 2/2014
IL 123646 5/2010
(Continued)

OTHER PUBLICATIONS

International Search Report and the Written Opinion dated Feb. 15, 2021 From the International Searching Authority Re. Application No. PCT/IL2020/051224. (24 Pages).
(Continued)

*Primary Examiner* — Wade Miles

(57) ABSTRACT

A compact robotic device for driving movement of two or more elongate surgical tools configured for a telescopic arrangement when said two or more elongate surgical tools are at least partially received within said device, the device comprising: a housing comprising walls which define an inner volume including at least two inner pathways for accommodating the two or more elongate surgical tools; the housing encasing: a plurality of motors, and two or more tool actuation assemblies configured at a position of each of the two or more inner pathways; the actuation assemblies
(Continued)

driven by the plurality of motors and configured to operably contact an elongate surgical tool at least partially received in the inner pathway to at least one of advance, retract and/or roll said elongate surgical tool.

22 Claims, 27 Drawing Sheets

Related U.S. Application Data

(60) Provisional application No. 63/082,508, filed on Sep. 24, 2020, provisional application No. 62/941,842, filed on Nov. 28, 2019.

(51) Int. Cl.
    *A61B 34/37* (2016.01)
    *B25J 9/10* (2006.01)
    *A61B 34/30* (2016.01)
    *A61B 34/35* (2016.01)
    *B25J 9/00* (2006.01)
    *A61M 25/00* (2006.01)
    *A61M 25/02* (2006.01)

(52) U.S. Cl.
    CPC ........ *A61M 25/0113* (2013.01); *B25J 9/0021* (2013.01); *B25J 9/102* (2013.01); *A61B 2034/301* (2016.02); *A61M 2025/0042* (2013.01); *A61M 2025/0253* (2013.01)

(56) References Cited

U.S. PATENT DOCUMENTS

| | | | |
|---|---|---|---|
| 7,615,042 B2 | 11/2009 | Beyar et al. | |
| 8,317,745 B2 | 11/2012 | Kirschenman et al. | |
| 8,423,182 B2 | 4/2013 | Robinson et al. | |
| 8,480,618 B2 | 7/2013 | Wenderow et al. | |
| 8,894,610 B2 | 11/2014 | Macnamara et al. | |
| 9,192,745 B2 | 11/2015 | Bencteux et al. | |
| 9,795,764 B2 | 10/2017 | Pacheco et al. | |
| 10,149,680 B2 | 12/2018 | Parihar et al. | |
| 10,376,323 B2 | 8/2019 | Farritor et al. | |
| 10,524,867 B2 | 1/2020 | Kokish et al. | |
| 10,543,047 B2 | 1/2020 | Yu | |
| 10,820,952 B2 | 11/2020 | Yu | |
| 10,980,608 B2 | 4/2021 | Scheib et al. | |
| 2002/0177789 A1 | 11/2002 | Ferry et al. | |
| 2014/0276647 A1 | 9/2014 | Yu | |
| 2014/0277333 A1* | 9/2014 | Lewis | A61B 34/30 623/1.11 |
| 2014/0305993 A1 | 10/2014 | Timm et al. | |
| 2015/0001968 A1 | 1/2015 | Zirps | |
| 2015/0094732 A1 | 4/2015 | Pacheco et al. | |
| 2015/0112362 A1 | 4/2015 | Inoue et al. | |
| 2015/0374956 A1 | 12/2015 | Bogusky | |
| 2016/0157941 A1 | 6/2016 | Anvari et al. | |
| 2017/0105804 A1 | 4/2017 | Yu | |
| 2019/0125397 A1 | 5/2019 | Arnold et al. | |
| 2020/0155245 A1 | 5/2020 | Yu | |
| 2020/0163726 A1 | 5/2020 | Tanner et al. | |
| 2021/0251709 A1 | 8/2021 | Sharon et al. | |
| 2021/0282875 A1 | 9/2021 | Sharon et al. | |

FOREIGN PATENT DOCUMENTS

| | | |
|---|---|---|
| WO | WO 99/45994 | 9/1999 |
| WO | WO 2019/070696 | 4/2019 |
| WO | WO 2019/173107 | 9/2019 |
| WO | WO 2021/011551 | 1/2021 |
| WO | WO 2021/105997 | 6/2021 |
| WO | WO 2021/105998 | 6/2021 |
| WO | WO 2021/105999 | 6/2021 |

OTHER PUBLICATIONS

International Search Report and the Written Opinion dated Feb. 18, 2021 From the International Searching Authority Re. Application No. PCT/IL2020/051226. (18 Pages).
International Search Report and the Written Opinion dated Feb. 25, 2021 From the International Searching Authority Re. Application No. PCT/IL2020/051225. (14 Pages).
Invitation to Pay Additional Fees and Communication Relating to the Results of the Partial International Search dated Jan. 12, 2021 From the International Searching Authority Re. Application No. PCT/IL2020/051224. (13 Pages).
Official Action dated Jun. 23, 2021 From the US Patent and Trademark Office Re. U.S. Appl. No. 14/187,936. (13 Pages).
Official Action dated Aug. 2, 2021 from the US Patent and Trademark Office Re. U.S. Appl. No. 17/331,837. (19 pages).
Interview Summary dated Oct. 20, 2021 from US Patent and Trademark Office Re. U.S. Appl. No. 17/331,837. (2 pages).

\* cited by examiner

| 2321 | Attach a proximal end of the tool to the robotic device |
| 2323 | Thread a more distal portion of the tool through the robotic device |
| 2325 | Optionally adjust a length of the tool at a curved portion of the tool extending between the attached end and the threaded portion |

DEVICE FOR AUTOMATICALLY INSERTING AND MANIPULATING A MEDICAL TOOL INTO AND WITHIN A BODILY LUMEN

RELATED APPLICATIONS

This application is a Continuation-in-Part (CIP) of PCT Patent Application No. PCT/IL2020/051226 filed on Nov. 26, 2020 which claims the benefit of priority under 35 USC § 119(e) of U.S. Provisional Patent Application Nos. 62/941,842 filed on Nov. 28, 2019, and 63/082,508 filed on Sep. 24, 2020. The contents of the above applications are all incorporated by reference as if fully set forth herein in their entirety.

FIELD AND BACKGROUND OF THE INVENTION

The present invention, in some embodiments thereof, relates to automated actuation of surgical tools inserted into a bodily lumen.

U.S. Pat. No. 10,543,047 discloses "A robotic instrument driver for elongate members includes a first elongate member, and at least one manipulator mechanism configured to manipulate the first elongate member, and at least one articulating drive configured to articulate the first elongate member, positionable on a bed and beside a patient access site. The manipulator and articulating drive are positioned relative to each other a distance less than the insertable length of the first elongate member, stationary in position."

SUMMARY OF THE INVENTION

According to an aspect of some embodiments there is provided a compact robotic device for driving and manipulating movement of one or more elongate surgical tools, comprising:

at least one motor;

at least one tool-moving element driven by the at least one motor, the tool—moving element positioned and configured to operably contact a tool at least partially received in the robotic device to advance, retract and/or rotate the elongate surgical tool; and a device housing shaped and sized to encase the at least one motor and the at least one tool-moving element.

In some embodiments, the at least one motor and the at least one tool-moving element are confined within walls of the housing, and wherein only the one or more elongate surgical tools, when received within the device, extend outwardly from the walls of the housing.

In some embodiments, walls of the housing define an inner volume of less than 2800 cm^3 and wherein the device has a weight of less than 850 grams.

In some embodiments, walls of the housing define at least one entry aperture through which the elongate surgical tool is inserted into the device and at least one exit aperture through which the elongate surgical tool exits the device.

In some embodiments, walls of the housing define at least two entry apertures and at least two exit apertures for at least two elongate surgical tools.

In some embodiments, the device comprises an anchoring location for a proximal portion of the elongate surgical tool, wherein the anchoring location and an entry aperture for the elongate surgical tool are aligned along a similar wall of the housing so that a segment of the elongate surgical tool extending externally to the housing and between the anchoring location and the entry aperture forms a U-shaped curve outside the housing.

In some embodiments, the housing comprises a designated elongate shaft for the elongate surgical tool to extend through, the at least one tool moving element positioned adjacent the shaft and protruding inside the shaft to operably contact the elongate surgical tool.

In some embodiments, the at least one tool-moving element comprises a set of opposing wheels configured to rotate to advance or retract the elongate surgical tool within the shaft.

In some embodiments, the shaft is connected to a gear which when rotated rotates the shaft along with the at least one tool-moving element and the tool received therein about the shaft long axis, thereby rolling the tool with the at least one tool-moving element.

In some embodiments, an inner contour of the shaft is shaped to match an outer contour of the at least one tool-moving element at their interface.

In some embodiments, the device comprises an anchoring location for a proximal portion of the elongate surgical tool, the anchoring location including a holder for holding a proximal portion of the elongate surgical tool, while a more distal portion of the elongate surgical tool is received within the designated elongate shaft.

In some embodiments, one of the motors is configured to drive rotation of the holder and of the elongate shaft, thereby rolling the elongate surgical tool at two spaced apart locations along the length of the elongate surgical tool.

In some embodiments, a bottom wall of the housing is saddle shaped.

In some embodiments, a bottom wall of the housing is flat.

In some embodiments, dimensions of the housing include a height shorter than 30 cm, a width shorter than 30 cm, a length shorter than 30 cm.

In some embodiments, the housing, at the entry aperture and/or at the exit aperture, comprises a conically shaped protrusion having a rounded external lip.

In some embodiments, the housing comprises a removable or movable cover providing access to the one or more elongate surgical tools loaded onto the device.

In some embodiments, the device is configured to drive and manipulate movement of at least one of a guidewire and a microcatheter.

According to an aspect of some embodiments there is provided a surgical system comprising:

a robotic device for example as described herein, and an add-on unit for driving movement of a guiding catheter, the add-on unit mechanically attachable to the housing of the robotic device.

In some embodiments, the system comprises a remote control device in communication with a controller of the robotic device.

In some embodiments, the system comprises an imaging modality in communication with a controller of the robotic device.

According to an aspect of some embodiments there is provided an assembly for driving linear movement and rotational movement of an elongate surgical tool, comprising:

a shaft comprising a slot in communication with a central lumen of the shaft, the lumen extending along the shaft long axis;

a set of wheels positioned opposing each other and aligned on two sides of the slot, the wheels at least partially extending through apertures in the elongate shaft and into the slot to contact an elongate surgical tool received therein;

a gear positioned and configured, when rotated, to rotate the shaft along with the set of wheels about the shaft long axis.

In some embodiments, the gear is linearly aligned with the shaft and is co-axial with the shaft.

In some embodiments, the assembly comprises a motor positioned and configured to drive rotation of the wheels, the motor positioned and configured to rotate with the shaft when the shaft is rotated.

In some embodiments, the gear comprises a slot on its circumference, the slot linearly aligned with the slot of the shaft.

In some embodiments, inner walls of the shaft which define the central lumen are contoured to match at least a portion of an external contour of at least one of the wheels of the set of wheels.

In some embodiments, the assembly comprises motor transmission in contact with the gear and configured to rotate the gear.

In some embodiments, each wheel of the set of wheels is arranged to lie on a plane that is substantially perpendicular to a plane defined by the slot.

In some embodiments, when the assembly is rotated about the shaft long axis, the set of wheels rotates along so that each wheel of the set of wheels remains lying on the plane that is substantially perpendicular to the plane defined by the slot.

According to an aspect of some embodiments there is provided a method of using a surgical robotic device for manipulation of at least one elongate surgical tool, comprising: providing a robotic device shaped and sized to be placed adjacent or on a surgical bed;

loading at least one elongate surgical tool onto the device;

controlling manipulation of the at least one elongate surgical tool by the robotic device via a remote control interface to carry out a surgical procedure; and disposing the robotic device along with the at least one elongate surgical tool following the surgical procedure.

In some embodiments, the robotic device comprises:
one or more motors;
one or more tool-moving elements driven by the one or more motors;
wherein loading places the at least one elongate surgical tool in direct operable contact with the one or more tool-moving elements, and the one or more tool-moving elements are in direct operable contact with the one or more motors.

In some embodiments, the robotic device is not covered by a sterile drape.

In some embodiments, the method comprises introducing the at least one elongate surgical tool into the body and allowing body fluids through the elongate surgical tool and into the robotic device.

According to an aspect of some embodiments there is provided a method of using a surgical robotic device for manipulation of at least one elongate surgical tool, comprising:

providing a robotic device shaped and sized to be attached to a patient's limb;

attaching the robotic device onto the patient's limb;

loading the at least one elongate surgical tool onto the device; and controlling manipulation of the at least one elongate surgical tool by the robotic device to carry out a surgical procedure.

In some embodiments, the limb is one of: a patient's leg where the robotic device is attached to the thigh, a patient's arm where the robotic device is attached adjacent the wrist.

In some embodiments, the method comprises forming an incision in the patient's groin and introducing, using the robotic device, the at least one elongate surgical tool through the incision.

In some embodiments, attaching comprises strapping the robotic device onto the limb.

According to an aspect of some embodiment there is provided a method of controlling a usable length of an elongate surgical tool, comprising:

providing a robotic device comprising a housing;

loading the elongate surgical tool onto the robotic device such that the elongate surgical tool is held at a first location along the length of the elongate surgical tool and slidably held at a second location along the length of the elongate surgical tool; wherein a segment of the tool extending between the first and second locations forms a curve; and sliding the elongate surgical tool at the second location to shorten or lengthen a distance between a maximal point of the curve and the housing of the robotic device to control the length of the elongate surgical tool.

In some embodiments, the method comprises controlling, via the shortening or lengthening, a length of a distal segment of the elongate surgical tool which extends from the robotic device housing to a target point inside the patient's body.

According to an aspect of some embodiments there is provided a compact robotic device for driving and manipulating movement of at least two elongate surgical tools, comprising:

a housing comprising:
at least one motor;
at least two assemblies, each assembly configured for driving linear movement and/or rotation of one of the at least two elongate surgical tools, each assembly comprising tool-moving elements driven by the at least one motor or associated transmission;
wherein the housing defines a volume of less than 2800 cm^3 and has a weight of less than 850 grams.

According to an aspect of some embodiments there is provided a compact robotic device for driving and manipulating movement of at least one elongate surgical tool, comprising:

a housing comprising:
at least one motor;
a first tool-moving element driven by the at least one motor, the tool-moving element positioned and configured to operably contact an elongate surgical tool at least partially received in the robotic device to advance or retract the elongate surgical tool; and
a second tool-moving element driven by the at least one motor and configured to roll the elongate surgical tool about the long axis of the elongate surgical tool.

In some embodiments, the housing comprises a shaft for the elongate surgical tool to extend through, the first tool-moving element at least partially protruding into the shaft to contact the elongate surgical tool.

In some embodiments, inner walls of the shaft are contoured to match at least a portion of an external contour of the first tool-moving element.

In some embodiments, the first tool-moving element comprises at least one pair of wheels which advance or retract the elongate surgical tool dependent on the wheel direction of rotation.

In some embodiments, the second tool-moving element comprises a gear aligned linearly along the shaft and configured to rotate the shaft.

According to some embodiments, there are provided advantageous medical devices for inserting and advancing a medical tool within bodily lumen(s), wherein the devices are configured to advance the medical tool in a linear movement and/or rotational movement. In some embodiments, the advantageous devices disclosed herein allow the insertion and advancement of more than one medical tool, separately or simultaneously, while being small in size, thereby configured to be mounted onto the subject body, or at least in close proximity thereto. In some embodiments, the devices disclosed herein are configured to operate automatically and/or controlled manually by a user, utilizing a remote controller. In some embodiments, further provided are systems which include the disclosed devices and methods of using the same in various medical procedures.

According to some embodiments, there is provided a medical device for advancing and inserting a medical tool into a bodily lumen, the device being configured to be mounted on the subject's body or to be positioned in close proximity thereto, and including: a housing configured for positioning the medical device on the body of the subject or in close proximity to the subject's body; at least one movement control unit comprising at least one actuator configured for linearly advancing the medical tool and at least one rotational actuator configured for rotating the medical tool; wherein the at least one rotational actuator and the at least one linear actuator are activated simultaneously and/or and independently from each other.

According to some embodiments, the device may further include a controller configured to activate the at least one linear actuator and the at least one rotational actuator. According to some embodiments, the controller may be configured for manual operation by a user. According to some embodiments, the controller may be configured for receiving commands from a processor. In some embodiments, the device may be autonomously computer controlled.

According to some embodiments, the at least one linear actuator and the at least one rotational actuator may have one or more common actuators.

According to some embodiments, the at least one linear actuator may include an actuator selected from: a DC motor, an AC motors, a stepper motors, an electromagnetic actuator, a piezoelectric actuator, a pneumatic actuator, an hydraulic actuator, or any combination thereof.

According to some embodiments, the at least one rotational actuator may include an actuator selected from: a DC motor, an AC motors, a stepper motors, an electromagnetic actuator, a piezoelectric actuator, a pneumatic actuator, an hydraulic actuator, or any combination thereof. In some embodiments, the medical device is disposable. In some embodiments, the medical device is miniature in size. In some embodiments, the medical device is lightweight.

According to some embodiments, the medical tool may be selected from: a guidewire, micro-catheter, balloon catheter, guiding catheter, stenting catheter, embolization catheter, stent retriever device, and the like, or any combination thereof.

According to some embodiments, the body lumen may be selected from a blood vessel, urethra and trachea, gastric anatomy, and the like. According to some embodiments, the device may include more than one movement control unit, wherein each control unit may be configured to linearly advance and/or rotate a separate medical tool or combination of two or more motors can perform a decoupled or combined motion of the medical tools.

According to some embodiments, the device may include two movement control units, wherein a first movement control unit is configured to linearly advance and/or rotate a first medical tool, and a second movement control unit configured to linearly advance and/or rotate a second medical tool.

According to some embodiments, the first medical tool may be a guidewire and the second medical tool may a catheter.

According to some embodiments, the first medical tool may be configured to advance through a lumen of the second medical tool.

According to some embodiments, the device may be further configured to allow control over the tip parameters of the medical tool.

According to some embodiments, the movement control unit may include at least two discs opposing each other along a portion of their external circumference, such that the medical tool is capable of being placed in a space formed therebetween, while maintaining at least partial contact with at least one of the discs, whereby upon spinning of said discs, the medical tool linearly advances. The surface of the external circumference of the discs may be rough, soft, smooth, coated, spongy, hydrophilic, hydrophobic, or with other characteristics that may optimize the interaction with the medical tool. The driving discs may be assembled in such a way that the medical tool is not actuated along a straight line, but along a curved route, thus allowing for higher driving force and higher rotational moment.

According to some embodiments, the medical device may further include a power source.

According to some embodiments, the device may be configured to linearly advance the medical tool at a constant or varying rate (velocity).

According to some embodiments, the device may be configured to automatically insert and advance the medical tool into the bodily lumen.

According to some embodiments, there is provided a system for inserting a medical tool into a bodily lumen, the system includes: a medical device for inserting the medical tool into the bodily lumen, the device being configured for positioning on or in close proximity to a body of a subject, and comprising: at least one movement control unit comprising at least one actuator configured for linearly advancing the medical tool and at least one rotational actuator configured for rotating the medical tool; a controller configured to activate the at least one linear actuator and the at least one rotational actuator, said controller is configured to activate the at least one rotational actuator and the at least one linear actuator at least one of simultaneously and independently from each other; and a processor configured to provide commands to said controller.

According to some embodiments, the controller may be configured for manual operation by a user.

According to some embodiments, the controller may include activating buttons, selected from: press buttons, sliding buttons, joystick, or any combination thereof.

According to some embodiments, the system disclosed herein is used for automatically inserting and advancing the medical tool into the bodily lumen in a medical procedure.

According to some embodiments, the medical procedure may include an endovascular procedure, selected from coronary, peripheral and cerebral endovascular procedures, gastric procedures, procedures in the urinal tract and in procedures in the respiratory tract.

According to some embodiments, the system may further include or be configured to operate in conjunction with an imaging device. According to some embodiments, the imaging device may be selected from: X-ray device, fluoroscopy device, CT device, cone beam CT device, CT fluoroscopy device, MRI device and ultrasound device. According to some embodiments, there is provided a method for inserting and advancing a medical tool into a bodily lumen, the method comprising: mounting and securing the medical device disclosed herein on a subject's body or positioning the medical device in close proximity to the subject's body, and advancing the medical tool into the bodily lumen of the subject. In some embodiments, the method is automatic (i.e. advancing of the medical tool is performed automatically by the medical device).

According to some embodiments, there is provided a body mountable medical device for inserting a medical tool into a bodily lumen, the device includes: a housing configured for positioning on a body of a subject and securing thereto; at least one linear actuator configured for linearly advancing the medical tool; at least one rotational actuator configured for rotating the medical tool; a controller configured to activate the at least one linear actuator and the at least one rotational actuator; wherein the controller is configured to activate the at least one rotational actuator and the at least one linear actuator at least one of simultaneously and independently from each other.

According to some embodiments, the guidewire and microcatheter, entering and exiting the device from the rear and front end, advantageously allow the motion of a microcatheter over the guidewire without having the microcatheter drive impair the guidewire drive.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

According to an aspect of some embodiments there is provided a medical device for advancing and inserting a medical tool into a bodily lumen, comprising: a housing configured for positioning the medical device on a or in close proximity to a body of a subject and securing thereto; at least one movement control unit comprising at least one actuator configured for linearly advancing the medical tool and at least one rotational actuator configured for rotating the medical tool; wherein the at least one rotational actuator and the at least one linear actuator are activated simultaneously and/or and independently from each other.

In some embodiments, the device comprises a controller configured to activate the at least one linear actuator and the at least one rotational actuator.

In some embodiments, the controller is configured for manual operation by a user.

In some embodiments, the controller is configured for receiving commands from a processor.

In some embodiments, the at least one linear actuator and the at least one rotational actuator have one or more common actuators.

In some embodiments, the at least one linear actuator comprises an actuator selected from: a DC motor, an AC motors, a stepper motors, an electromagnetic actuator, a piezoelectric actuator, pneumatic actuator, hydraulic actuator, or any combination thereof.

In some embodiments, the at least one rotational actuator comprises an actuator selected from: a DC motor, an AC motors, a stepper motors, an electromagnetic actuator, a piezoelectric actuator, pneumatic actuator, hydraulic actuator, or any combination thereof.

In some embodiments, the medical device is disposable.

In some embodiments, the medical tool is selected from: a guide wire, micro-catheter, balloon catheter, a guiding catheter, stent, retrieval device, or any combination thereof.

In some embodiments, the body lumen is selected from, a blood vessel, urethra, trachea and gastrointestinal.

In some embodiments, the device comprises more than one movement control unit, wherein each control unit is configured to linearly advance and/or rotate a separate medical tool.

In some embodiments, the device comprises two movement control units, wherein a first movement control unit is configured to linearly advance and/or rotate a first medical tool, and a second movement control unit configured to linearly advance and/or rotate a second medical tool.

In some embodiments, the first medical tool is a guidewire and the second medical tool is a catheter.

In some embodiments, the first medical tool is configured to advance through a lumen of the second medical tool.

In some embodiments, the device is further configured to allow control over the tip parameters using additional actuator of the medical tool.

In some embodiments, the movement control unit comprises at least two discs opposing each other along a portion of their external circumference, such that the medical tool is capable of being placed in a space formed therebetween, while maintaining at least partial contact with at least one of the wheels whereby upon spinning of the discs, the medical tool linearly advances. In some embodiments, the device comprises a power source.

In some embodiments, the device is configured to linearly advance the medical tool at a constant or varying rate (velocity).

In some embodiments, the device is configured to automatically insert and advance the medical tool into the bodily lumen.

According to an aspect of some embodiments there is provided a system for inserting a medical tool into a bodily lumen, the system comprising: a medical device for inserting the medical tool into the bodily lumen, the device comprising: a housing configured for positioning the medical device on a body of a subject or in close proximity thereto, and securing thereto; at least one movement control unit comprising at least one actuator configured for linearly advancing the medical tool and at least one rotational actuator configured for rotating the medical tool; a controller configured to activate the at least one linear actuator and the at least one rotational actuator, the controller is configured to activate the at least one rotational actuator and the at least one linear actuator at least one of simultaneously and independently from each other; and a processor configured to provide commands to the controller.

In some embodiments, the controller is configured for manual operation by a user.

In some embodiments, the controller comprises activating buttons, selected from: press buttons, sliding buttons, joystick, or any combination thereof.

In some embodiments, the at least one linear actuator and the at least one rotational actuator have one or more common actuators.

In some embodiments, the at least one linear actuator comprises an actuator selected from: a DC motor, an AC motors, a stepper motors, an electromagnetic actuator, a piezoelectric actuator, a pneumatic actuator, an hydraulic actuator, or any combination thereof.

In some embodiments, the at least one rotational actuator comprises an actuator selected from: a DC motor, an AC motors, a stepper motors, an electromagnetic actuator, a piezoelectric actuator, a pneumatic actuator, an hydraulic actuator, or any combination thereof.

In some embodiments, the medical device is disposable.

In some embodiments, the medical tool is selected from: a guide wire, micro-catheter, a guiding catheter and balloon catheter.

In some embodiments, the body lumen is selected from, a blood vessel, urethra, gastric and trachea.

In some embodiments, the system comprises two movement control units, wherein a first movement control unit is configured to linearly advance and/or rotate a first medical tool, and a second movement control unit configured to linearly advance and/or rotate a second medical tool. In some embodiments, the first medical tool is a guidewire and the second medical tool is a catheter.

In some embodiments, the system is configured for automatically inserting and advancing the medical tool into the bodily lumen in a medical procedure.

In some embodiments, the medical procedure is selected from coronary, peripheral, and cerebral endovascular procedures, gastric procedure, urinal procedures and respiratory tract procedures.

In some embodiments, the system further comprises an imaging device.

In some embodiments, the imaging device is selected from: Xray device, fluoroscopy device, CT device, cone beam CT device, CT fluoroscopy device, MRI device and ultrasound device.

According to an aspect of some embodiments there is provided a method for inserting and advancing a medical tool into a bodily lumen, the method comprising: positioning a medical device on or in close proximity to a body of a subject, the device comprising: a housing configured for positioning the medical device on or in close proximity to a body of a subject and securing thereto; at least one movement control unit comprising at least one actuator configured for linearly advancing the medical tool and at least one rotational actuator configured for rotating the medical tool; wherein the at least one rotational actuator and the at least one linear actuator are activated simultaneously and/or and independently from each other; and; advancing the medical tool into the bodily lumen of the subject.

In some embodiments, the medical tool is selected from: a guidewire, a micro-catheter, a guiding catheter and a balloon catheter.

In some embodiments, the body lumen is selected from, a blood vessel, urethra and trachea.

In some embodiments, advancing of the medical tool is performed automatically by the medical device.

According to an aspect of some embodiments there is provided a medical device for inserting a medical tool into a bodily lumen, comprising: a housing configured for positioning on a body of a subject or in close proximity to the subject and securing thereto; at least one linear actuator configured for linearly advancing the medical tool; at least one rotational actuator configured for rotating the medical tool; a controller configured to activate the at least one linear actuator and the at least one rotational actuator; wherein the controller is configured to activate the at least one rotational actuator and the at least one linear actuator at least one of simultaneously and independently from each other.

In some embodiments, the controller is configured for manual operation by a user.

In some embodiments, the controller is configured for receiving commands from a processor.

In some embodiments, the controller is configured to receive commands from wireless remote controller.

In some embodiments, the wireless remote controller is a Wi-Fi remote controller, and Bluetooth remote controller.

In some embodiments, the at least one linear actuator and the at least one rotational actuator have one or more common actuators.

In some embodiments, the at least one linear actuator comprises at least one piezoelectric actuator.

In some embodiments, the at least one rotational actuator comprises at least one piezoelectric actuator.

According to an aspect of some embodiments there is provided a compact robotic device for driving movement of two or more elongate surgical tools when the two or more elongate surgical tools are at least partially received within the device, the device comprising:
a housing comprising walls which define an inner volume including at least two inner pathways for accommodating the two or more elongate surgical tools
the housing encasing:
a plurality of motors;
two or more tool actuation assemblies configured at a position of each of the two or more inner pathways; the actuation assemblies driven by the plurality of motors and configured to operably contact an elongate surgical tool at least partially received in the inner pathway to at least one of advance, retract and/or roll the elongate surgical tool.

In some embodiments, each of the two or more inner pathways extends across the inner volume between an entry aperture and an exit aperture, the entry aperture and the exit aperture being configured on opposite walls of the device housing and in communication with the inner volume.

In some embodiments, no inner barrier exists between the two or more inner pathways such that the two or more tool actuation assemblies and the plurality of motors all share the inner volume with no separation therebetween.

In some embodiments, at least one fixation location is defined externally to the walls of the housing for securing a proximal end of an elongate surgical tool to the housing.

In some embodiments, the at least one fixation location is located at one of the exit apertures, such that an elongate surgical tool exiting the inner volume through the exit aperture is led into a lumen of a proximal end of a second elongate surgical tool, forming a telescopic arrangement of the two tools.

In some embodiments, the at least one fixation location and one of the at least two entry apertures are defined along the same wall of the housing such that an elongate surgical tool secured to the device at the at least one fixation location forms a curve before entering the inner volume through the at least one entry aperture.

In some embodiments, the two or more inner pathways are parallel to each other and have a similar axial extent.

In some embodiments, a distance between long axes of the inner pathways is shorter than 10 cm.

In some embodiments, the tool actuation assemblies are both confined within the walls of the housing, and wherein only portions of the two or more elongate surgical tools, when received within the device, extend outwardly from the walls of the housing to a distance of at least 1 cm away from the housing.

In some embodiments, the inner volume is smaller than 2800 cm^3 and wherein the device has a weight of less than 850 grams.

In some embodiments, the plurality of motors comprises 3-5 motors.

In some embodiments, each of the actuation assemblies comprises:
a designated elongate shaft extending axially along at least a portion of a length of the inner pathway for the elongate surgical tool to extend through; and
at least one pair of wheels positioned adjacent the shaft and protruding inside the shaft to operably contact the elongate surgical tool received within the shaft.

In some embodiments, each of the actuation assemblies comprises a plurality of wheels pairs, each wheel pair comprising a set of opposing wheels arranged to define the inner pathway therebetween.

In some embodiments, the at least one pair of wheels comprises a set of opposing wheels configured to rotate to advance or retract the elongate surgical tool within the shaft.

In some embodiments, the shaft is connected to a gear which when rotated rotates the shaft along with the plurality of wheels and with the elongate surgical tool received therein about the shaft long axis, thereby rolling the elongate surgical tool.

In some embodiments, dimensions of the housing include a height shorter than 30 cm, a width shorter than 30 cm, a length shorter than 30 cm; wherein each of the inner pathways extends axially along the length.

In some embodiments, the housing, at at least one of the entry aperture and/or at at least one of the exit aperture, comprises a conically shaped protrusion having a rounded external lip.

In some embodiments, the housing comprises a removable or movable cover providing access to the one or more elongate surgical tools loaded onto the device and extending along at least a portion of the inner pathways.

In some embodiments, the device is configured to drive movement of a guidewire and a microcatheter, the guidewire configured to at least partially extend through a lumen of the microcatheter.

In some embodiments, the device comprises a controller configured to control the plurality of motors for driving the two or more actuation assemblies.

In some embodiments, the controller is controlled remotely by an external remote control device.

In some embodiments, there is provided a kit comprising: a device for example as described herein; a guidewire for loading onto the device such that at least a portion of the guidewire extends along one of the inner pathways; and microcatheter for loading onto the device such that at least a portion of the microcatheter extends along a second of the inner pathways.

In some embodiments, there is provided a surgical system comprising: a robotic device for example as described herein; and an add-on unit for driving movement of a guiding catheter, the add-on unit mechanically attachable to the housing of the robotic device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 8:
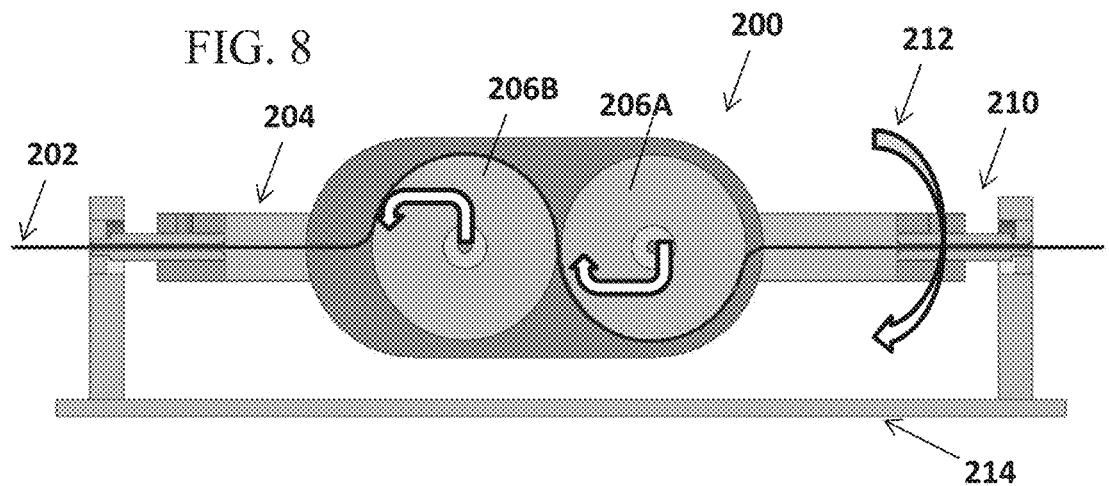
Figure 9A:
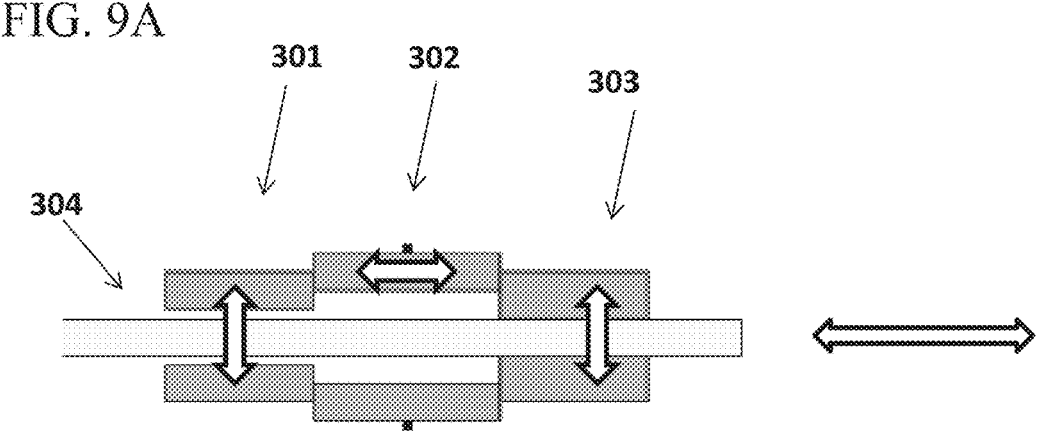
Figure 9B:
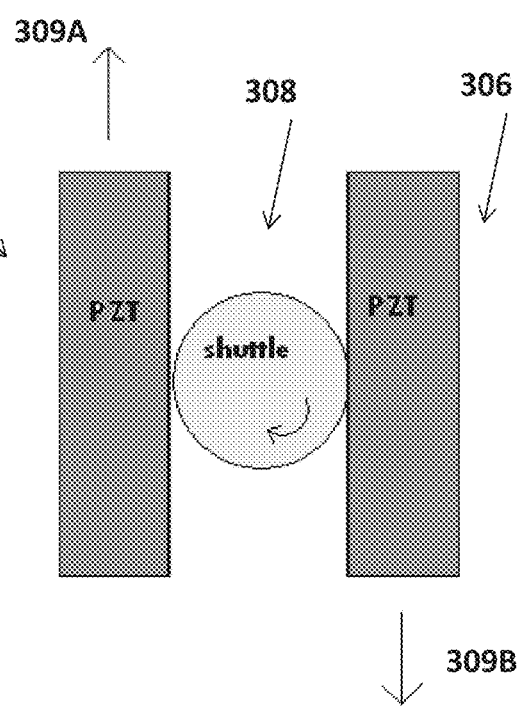
Figure 10:
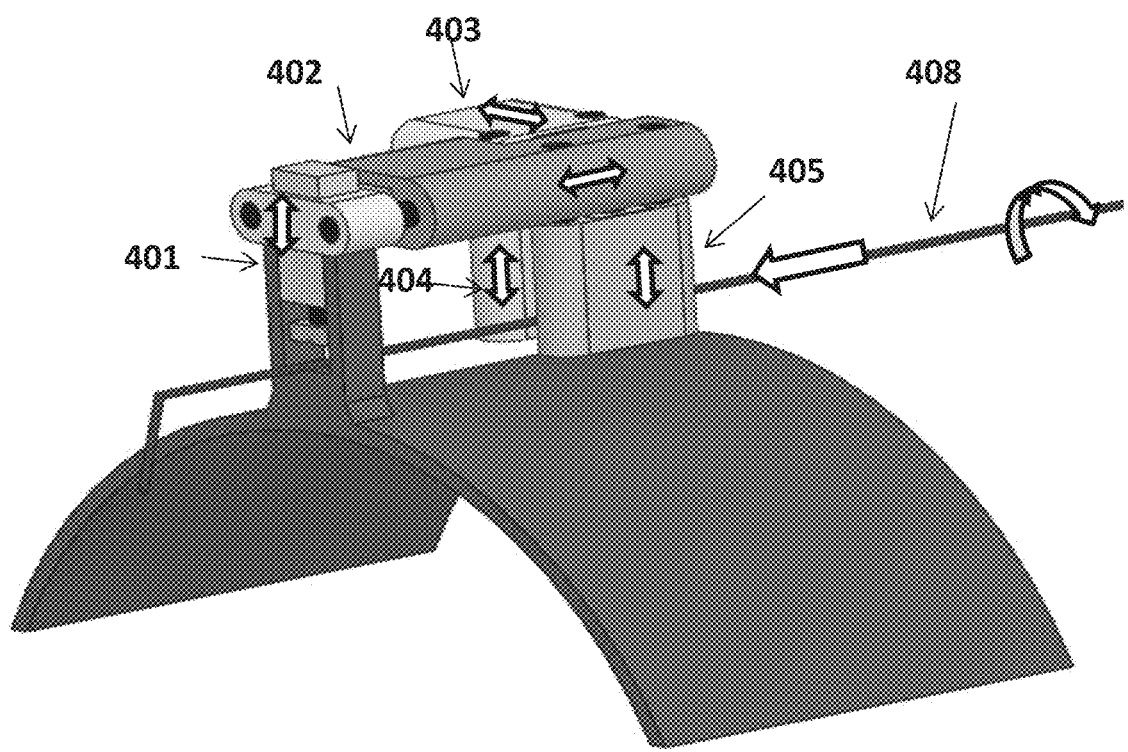
Figure 11:
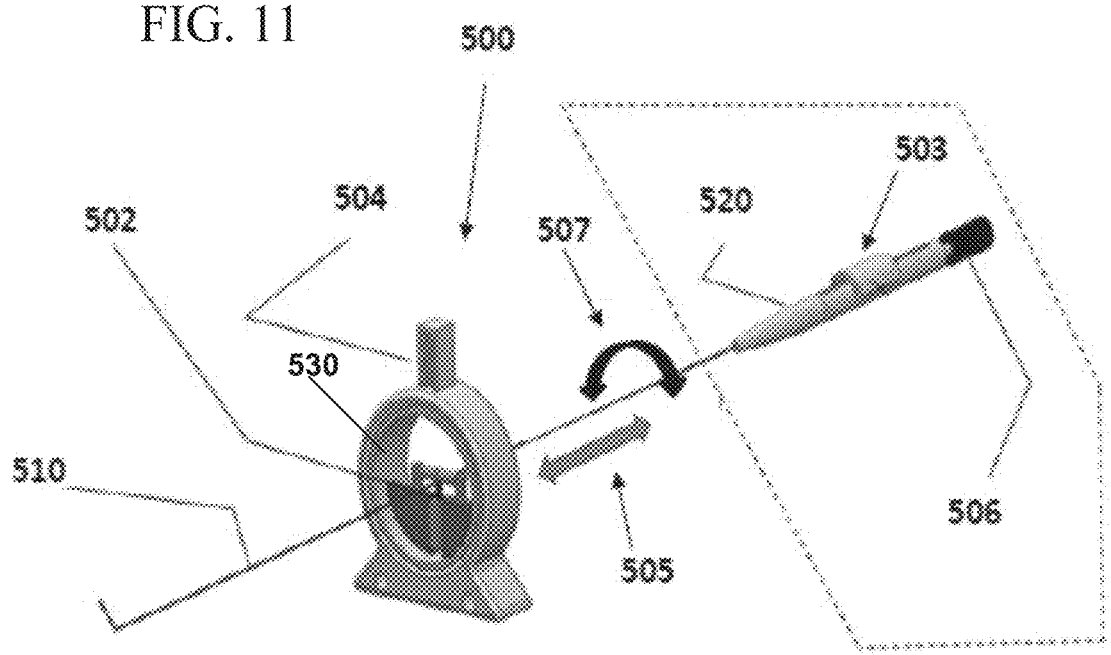

FIG. 8 schematically illustrates a movement control unit, according to some embodiments;

FIGS. 9A-9B illustrate moving units for linear advancement and/or rotational movement of a medical instrument, according to some embodiments. FIG. 9A shows schematically a piezoelectric actuated mechanism for linear translation of a medical tool, according to some embodiments, and FIG. 9B shows schematically a piezoelectric actuated mechanism for rotating a medical tool, according to some embodiments;

FIG. 10 depicts schematic illustrations of an exemplary device capable of imparting both linear and rotational motion on a medical tool, according to some embodiments;

FIG. 11 illustrates a movement control unit, according to some embodiments.

Figure 12:
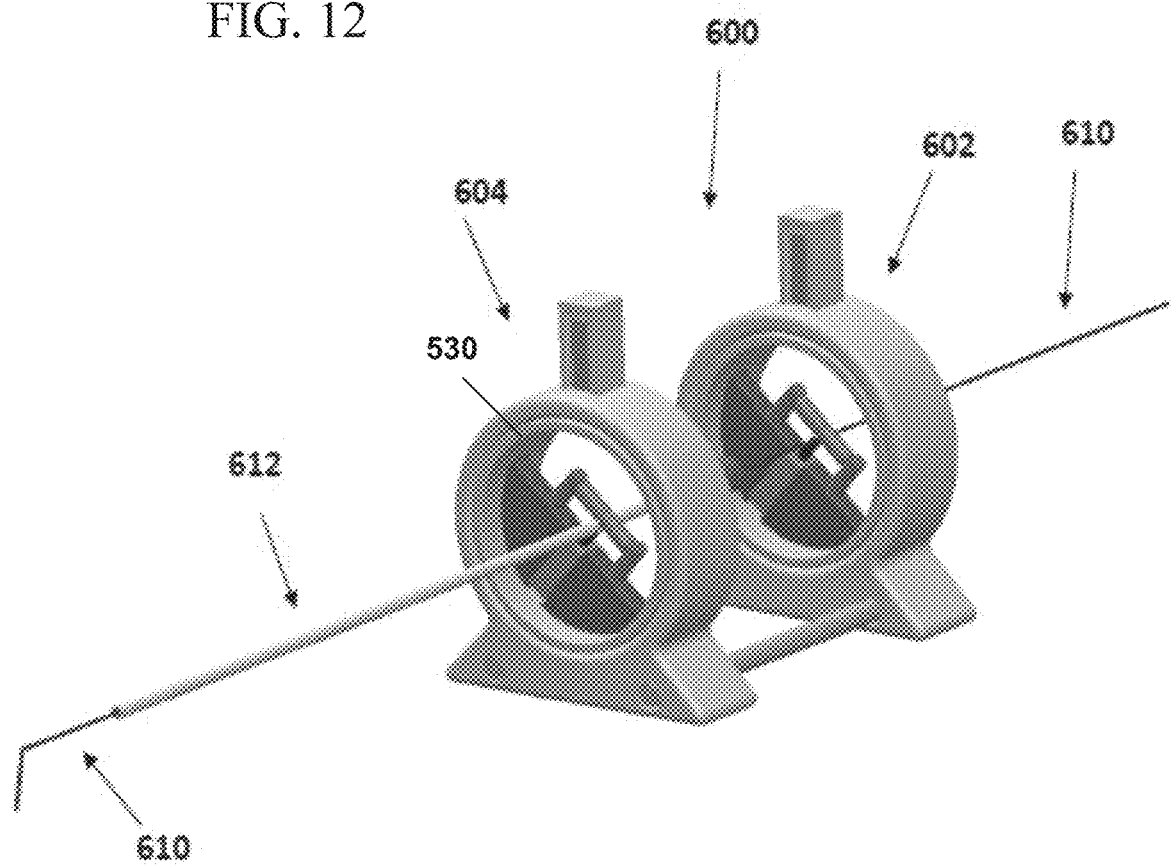
Figure 13:
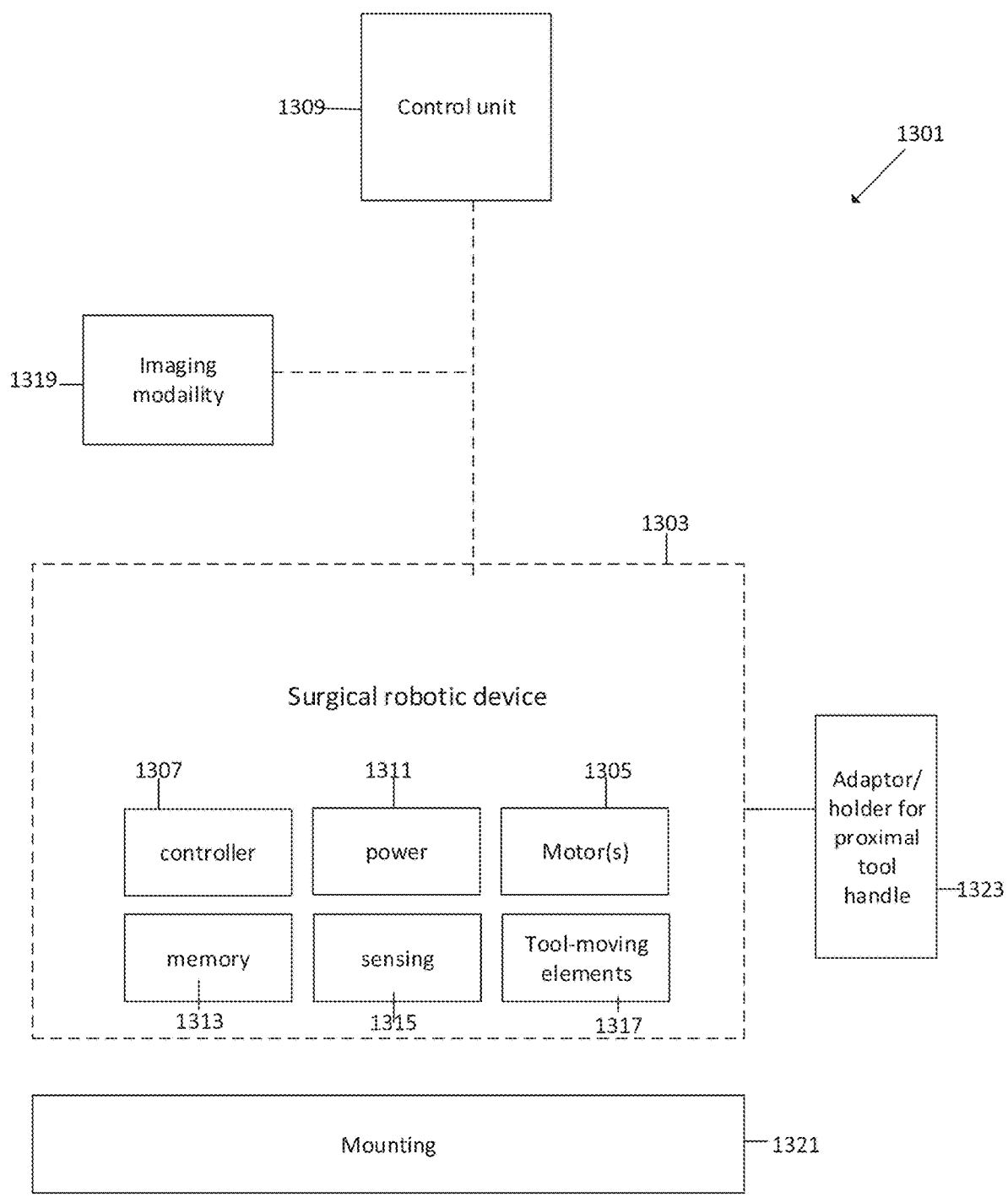
Figure 14:
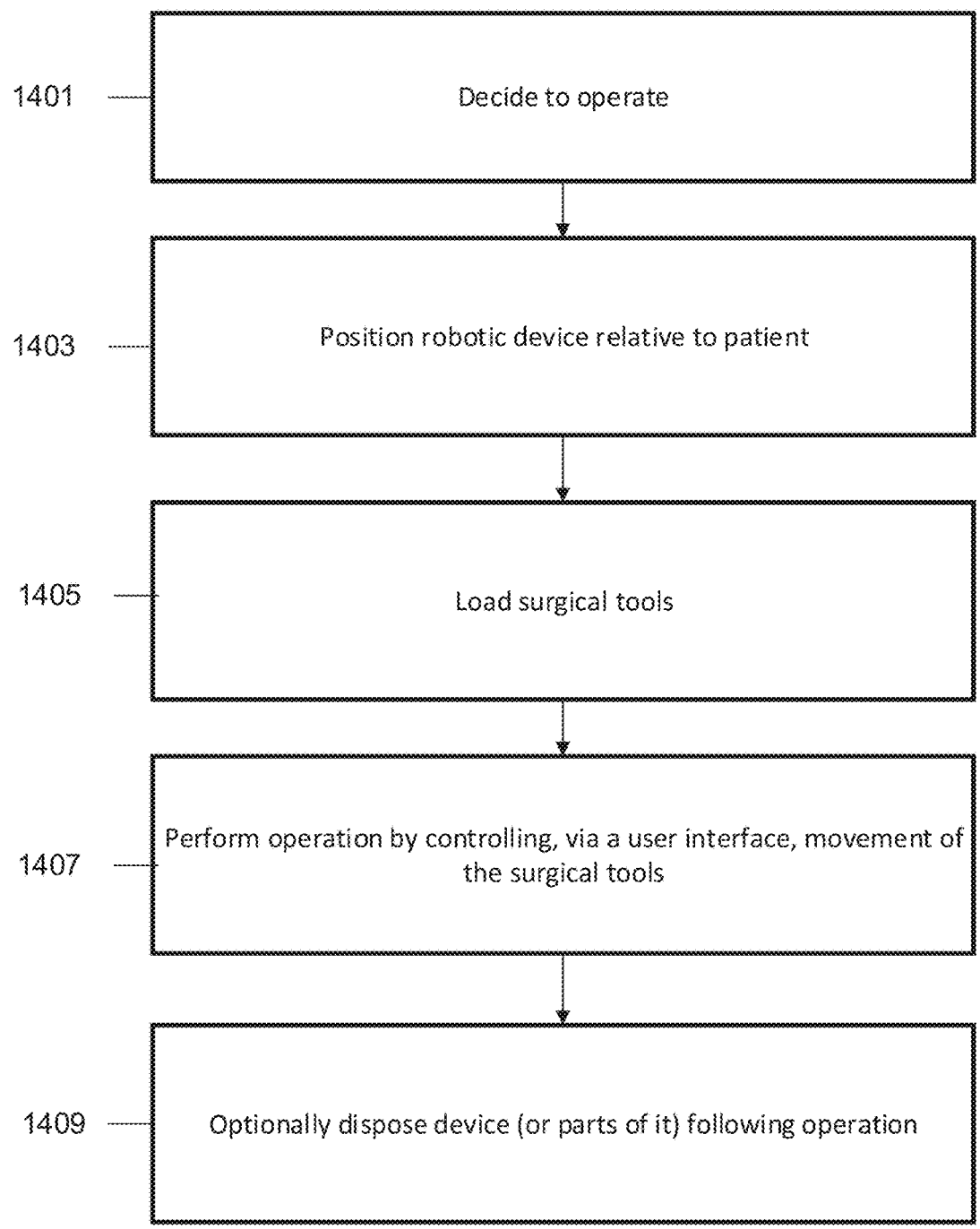
Figure 15:
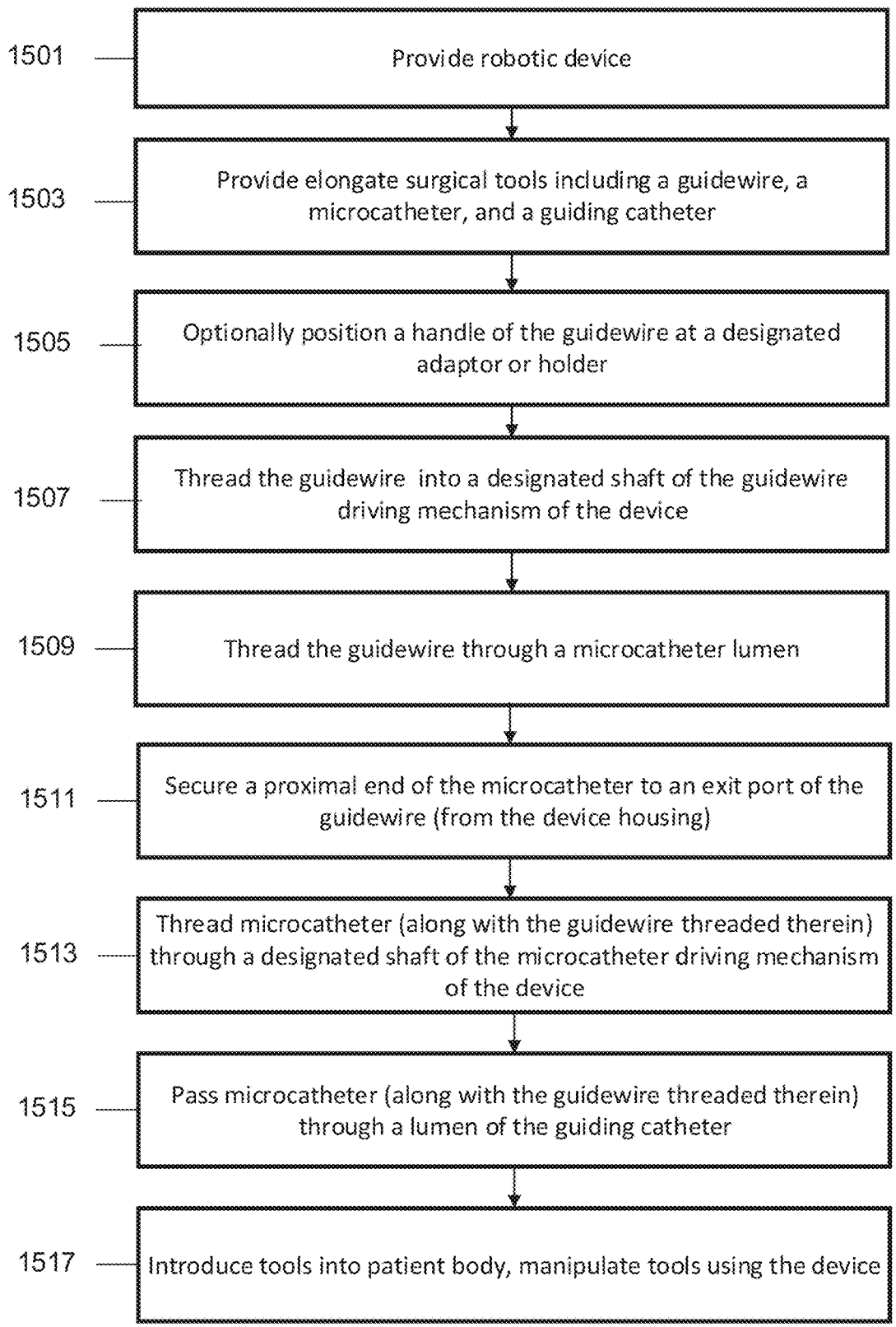
Figure 17:
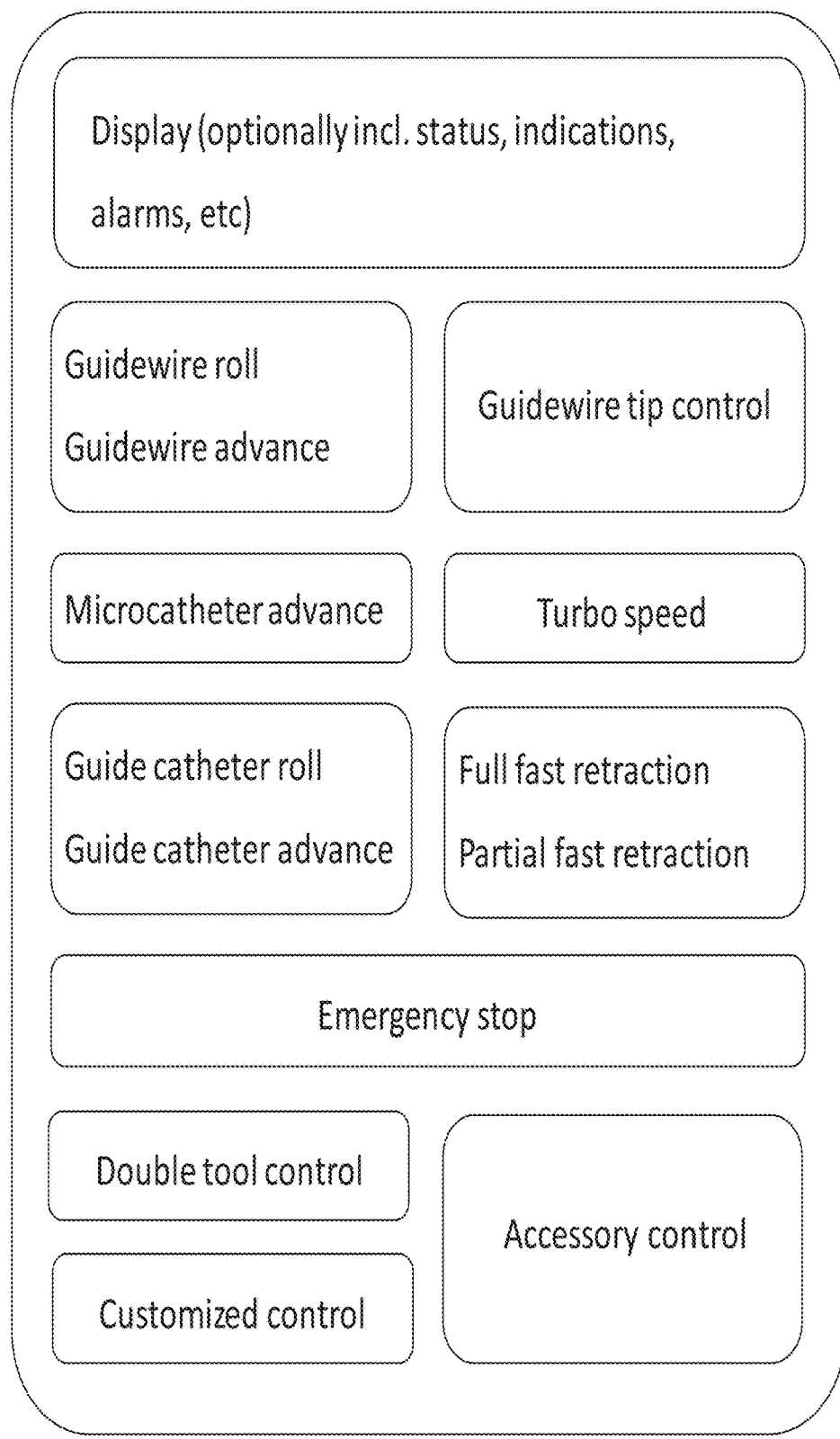
Figure 18A:
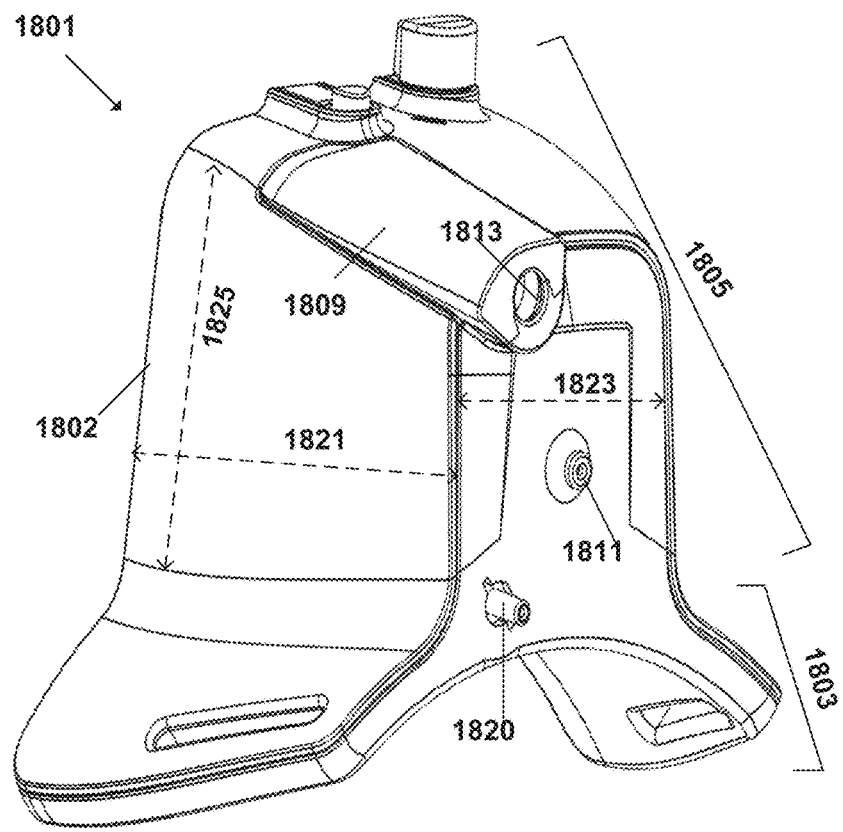
Figure 18B:
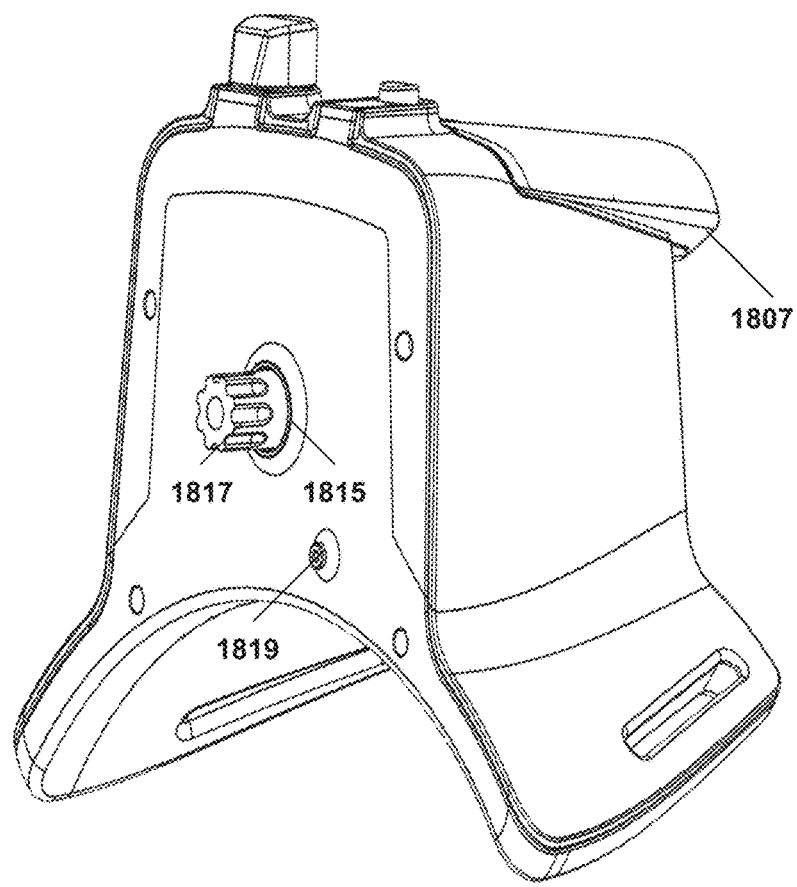
Figure 19A:
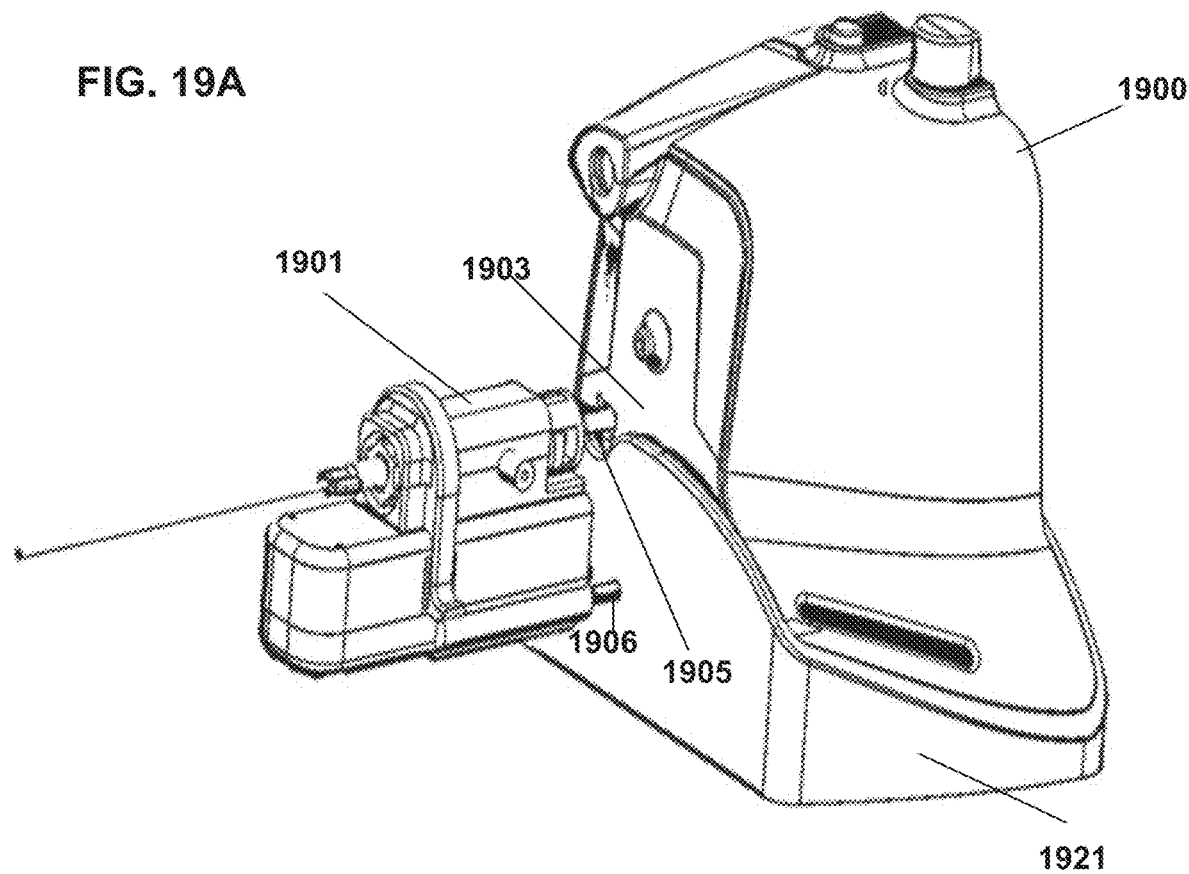
Figure 19B:
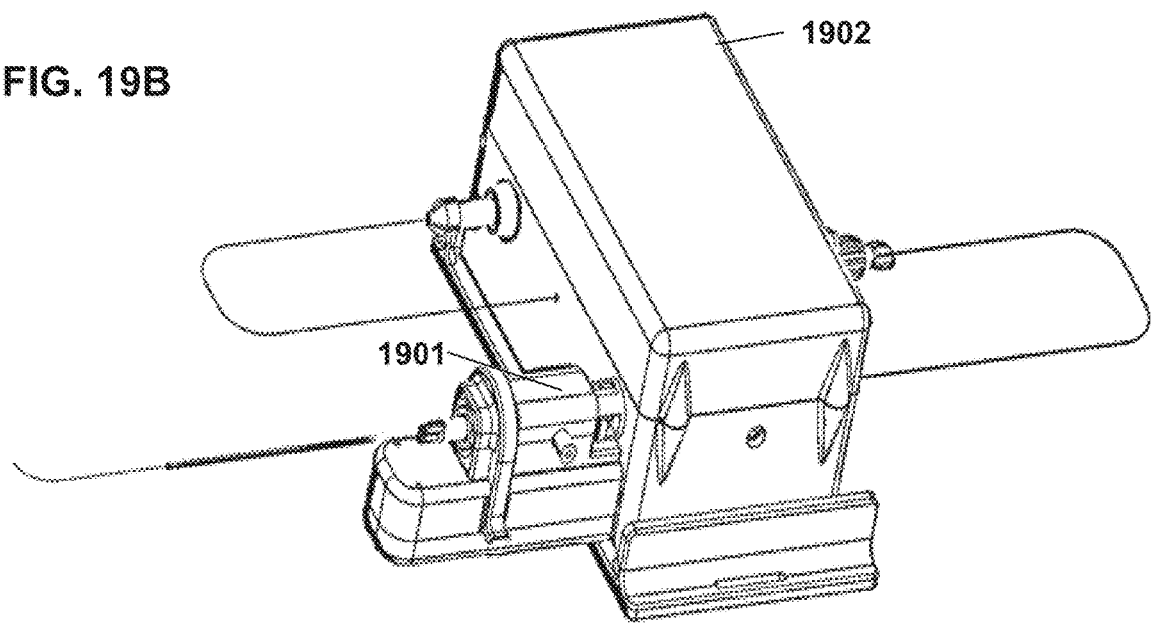
Figure 20A:
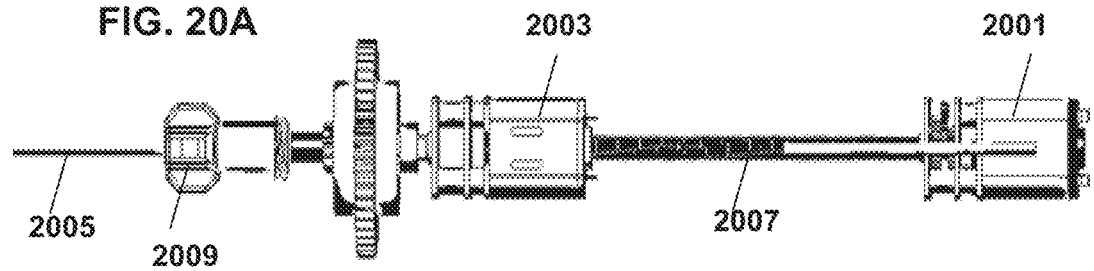
Figure 20B:
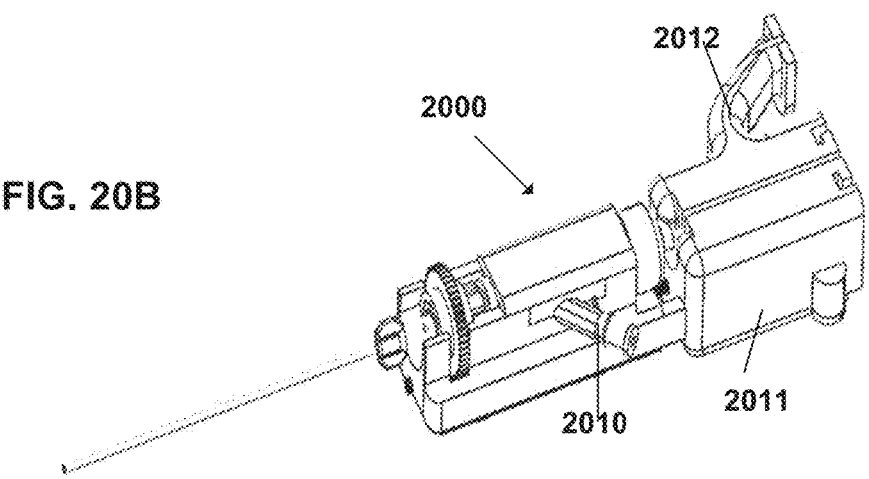
Figure 20C:
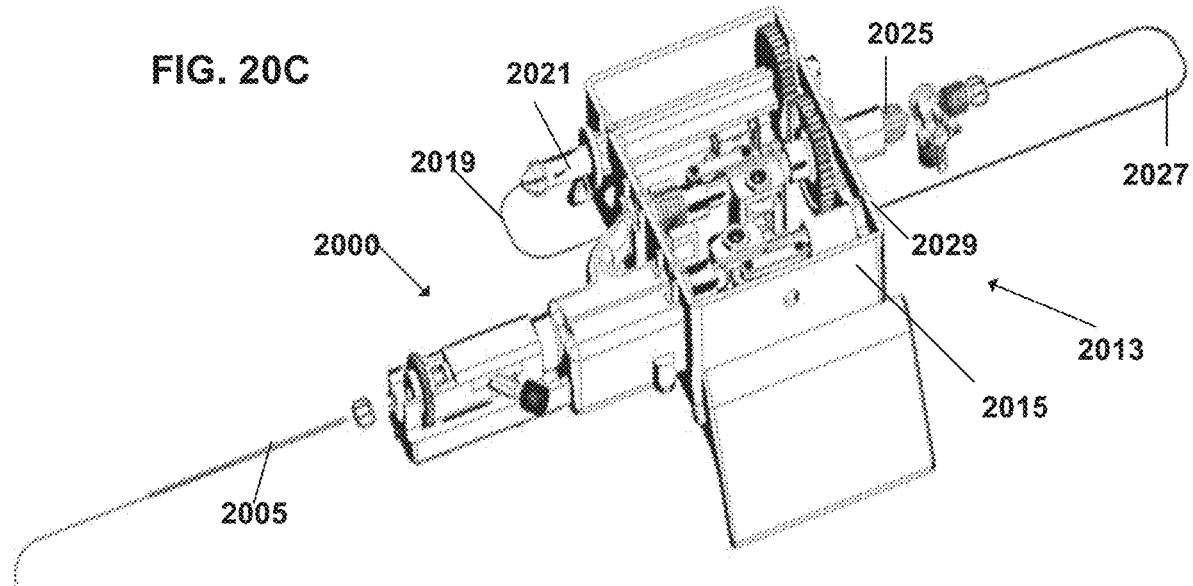
Figure 21A:
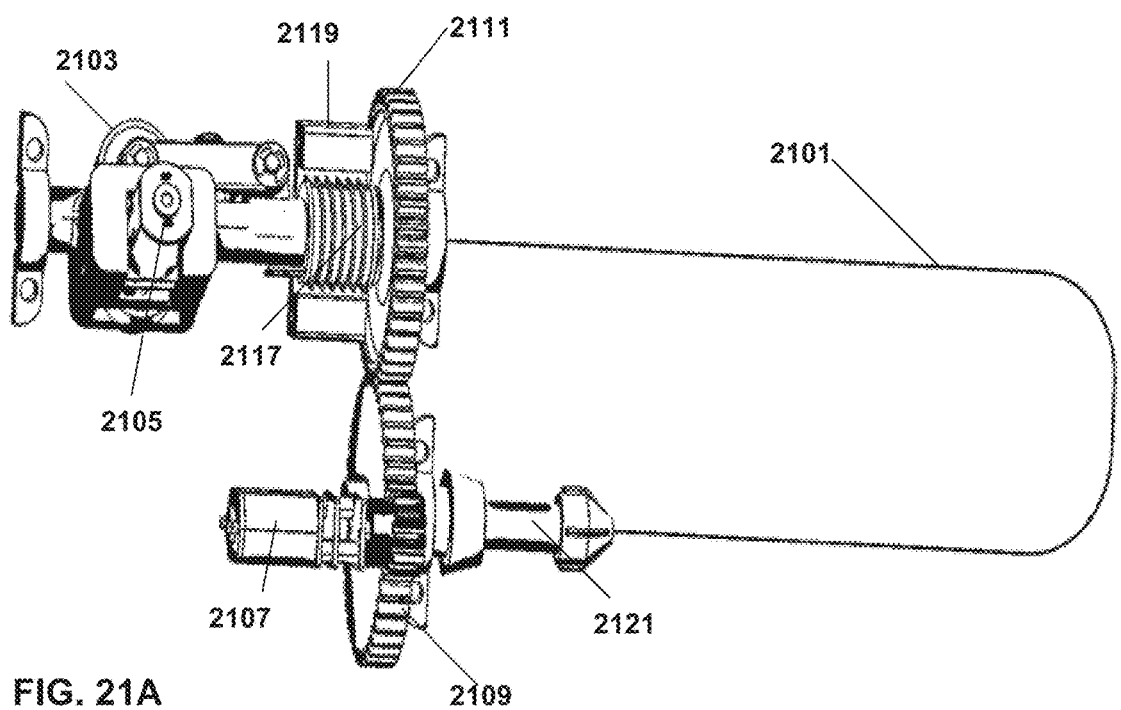
Figure 21B:
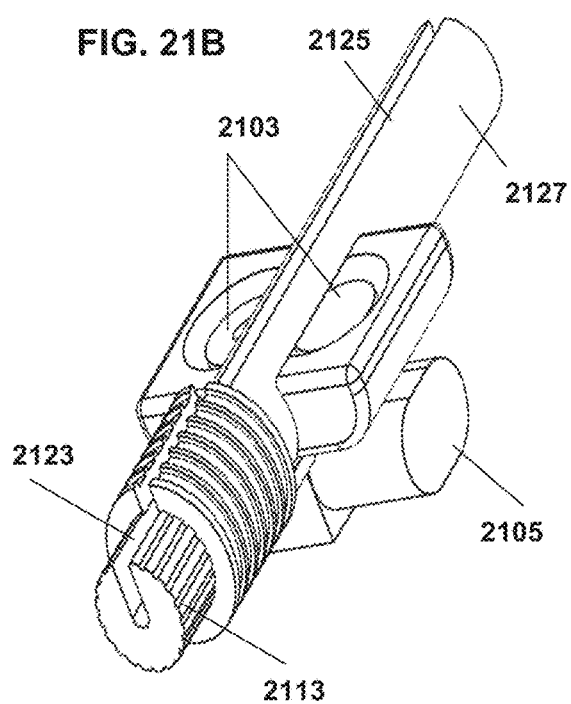
Figure 21C:
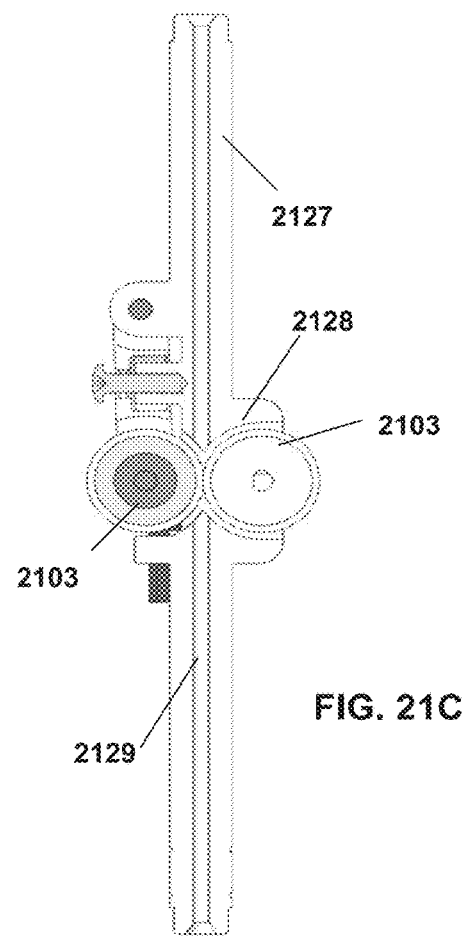
Figure 22:
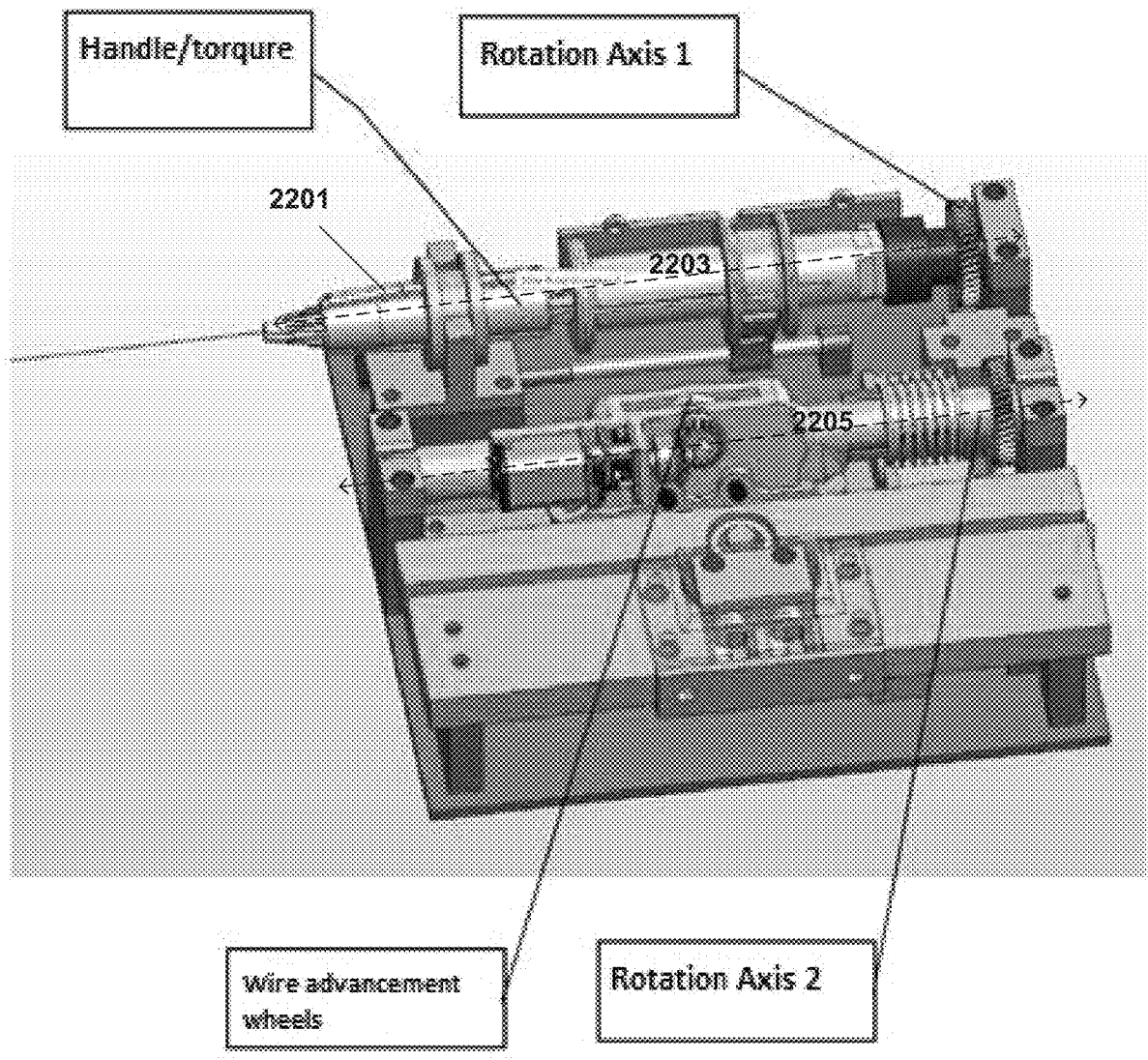
Figures 23A, 23B:
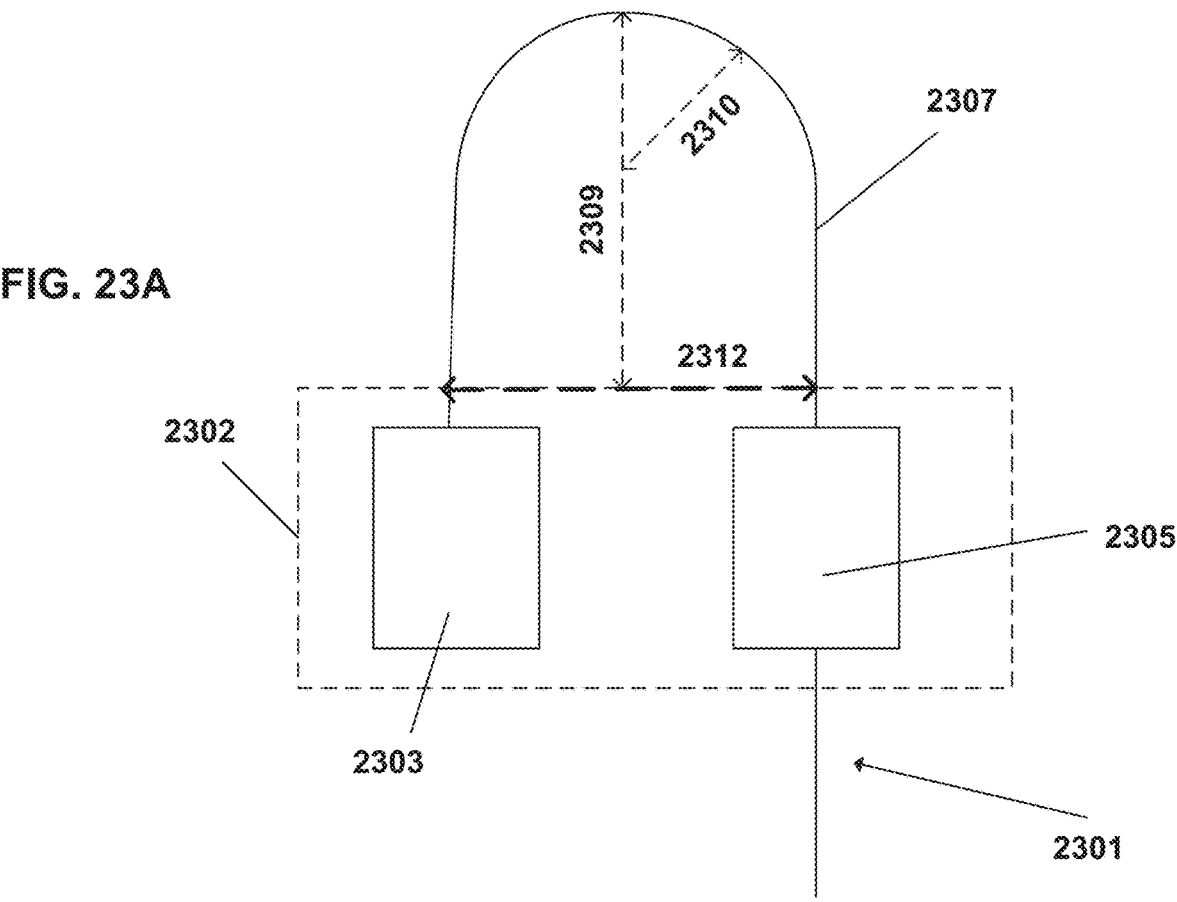
Figure 24:
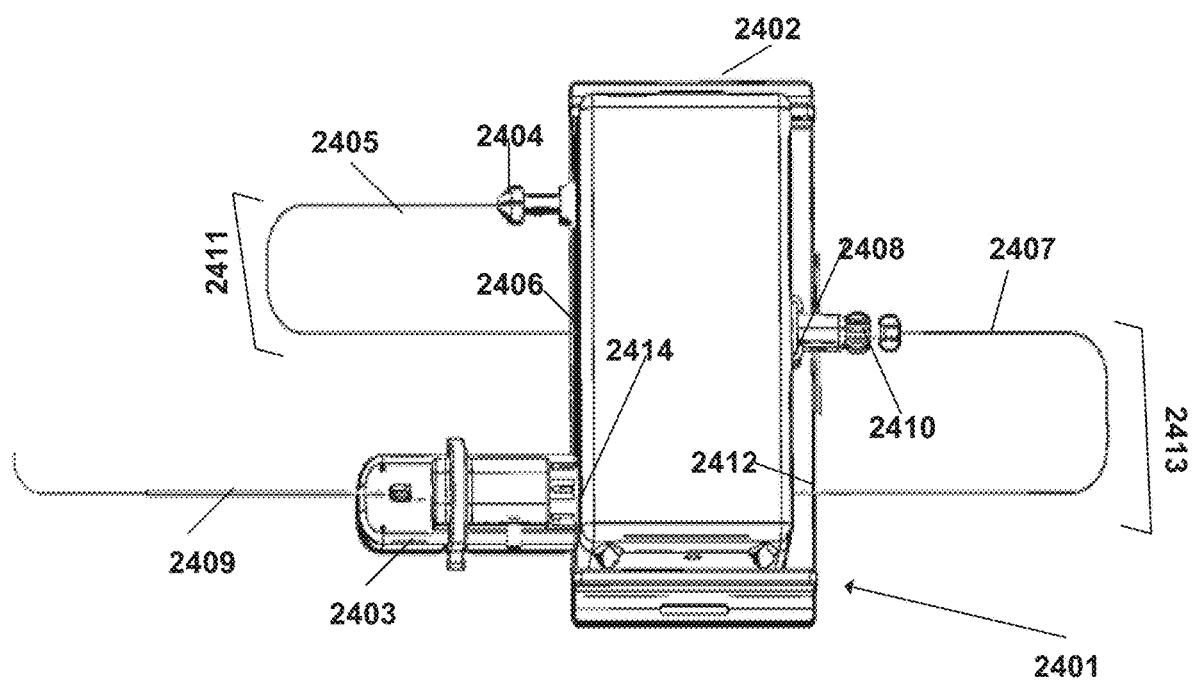
Figure 25:
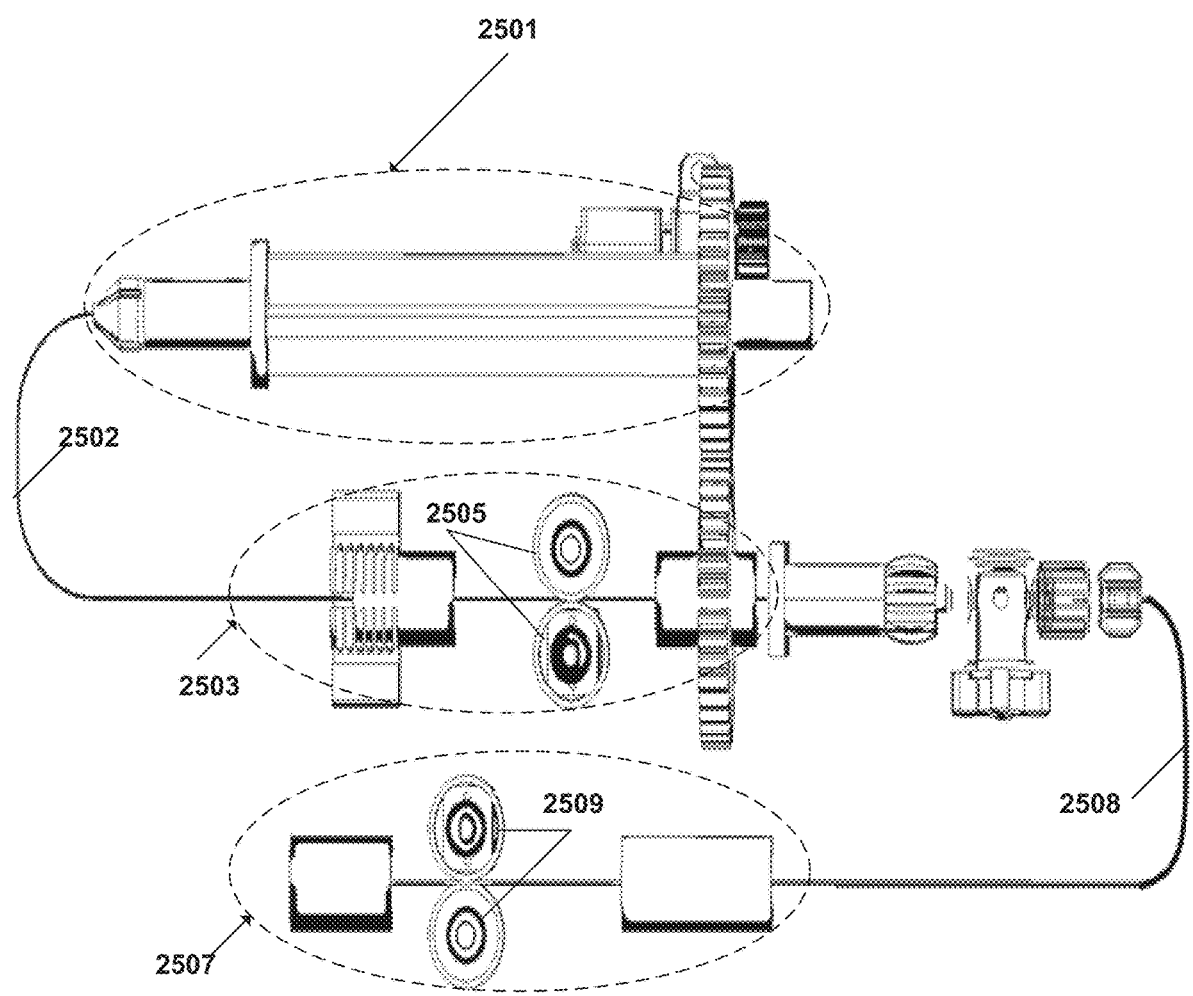
Figure 26A:
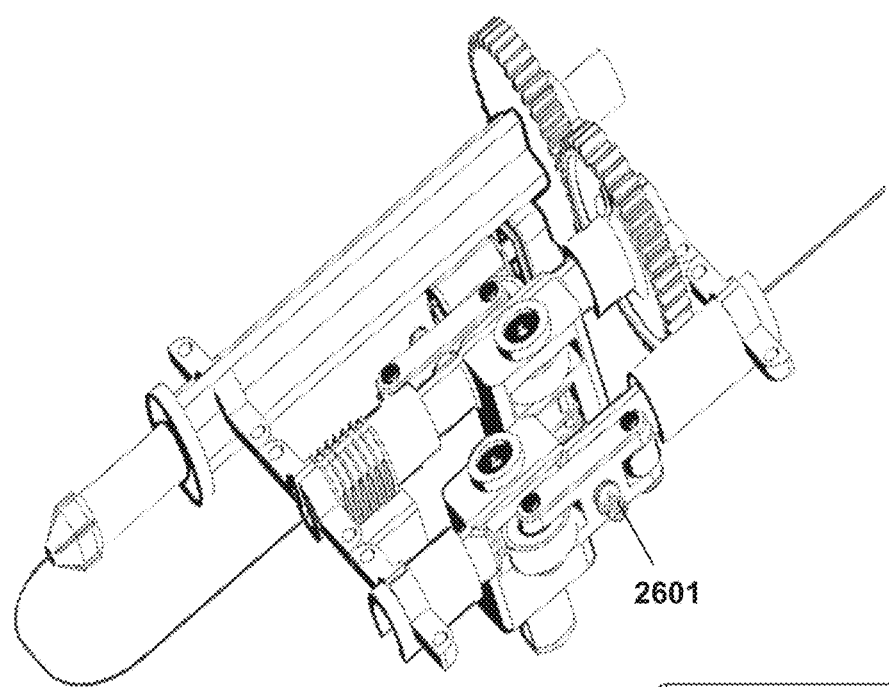
Figure 26B:
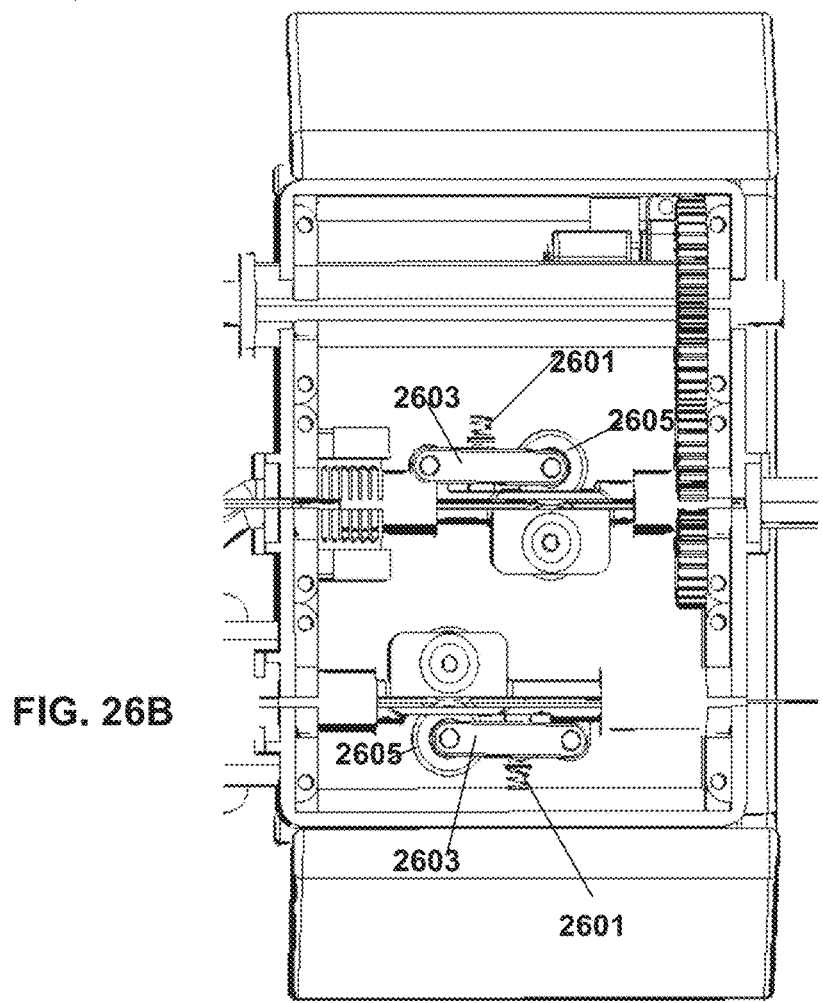
Figure 27:
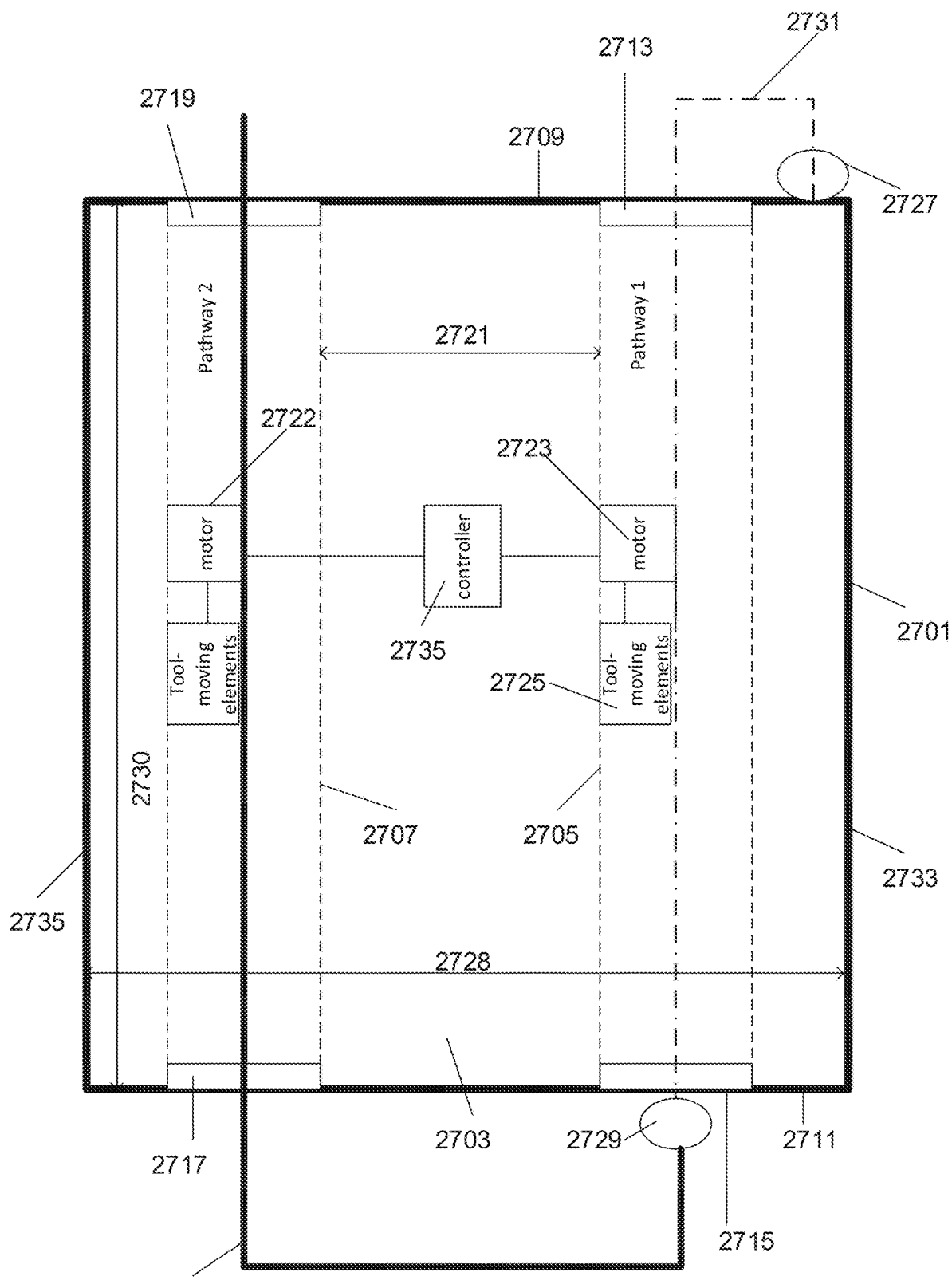
Figure 28:
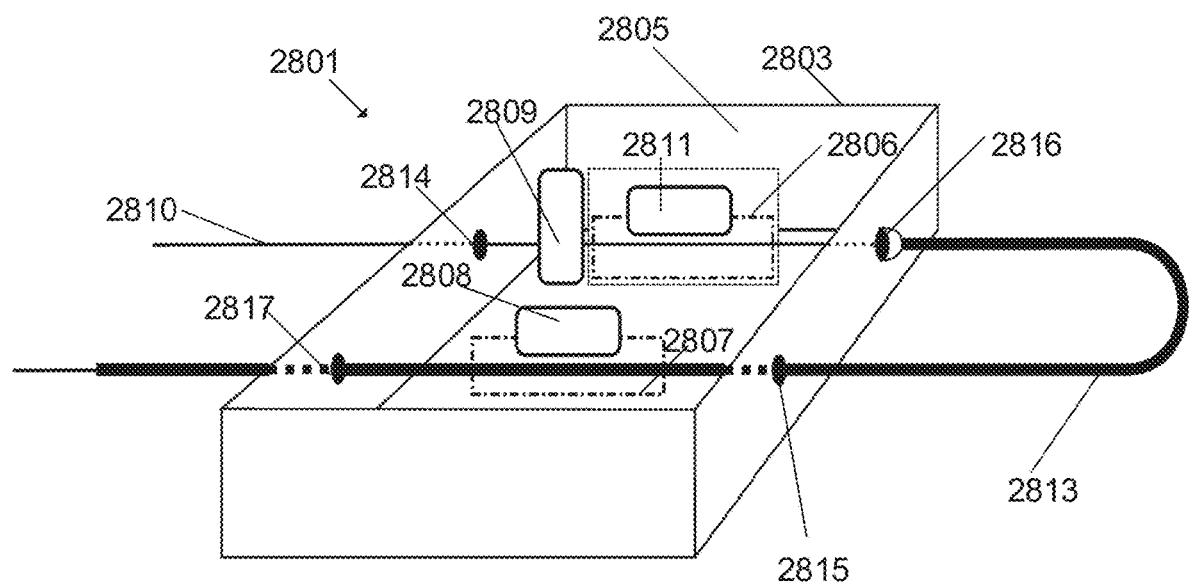
Figure 29:
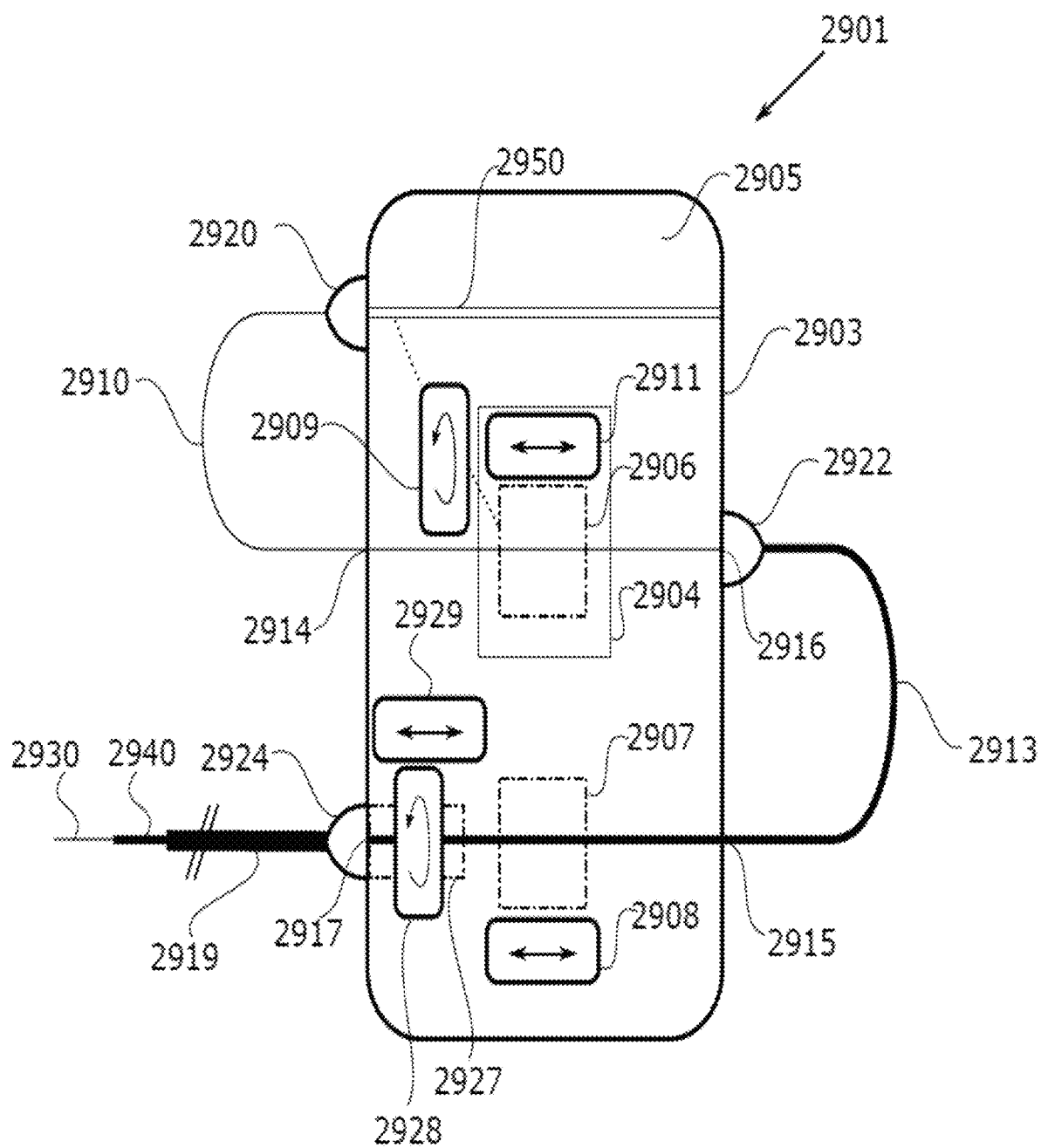

FIG. 12 illustrates an assembly of movement control units, for controlling movement of more than one medical instrument, according to some embodiments;

FIG. 13 is a block diagram of a surgical robotic system, according to some embodiments;

FIG. 14 is a flowchart of a general method of using a surgical robotic device, according to some embodiments;

FIG. 15 is a flowchart of a method of loading a plurality of surgical tools onto the surgical robotic device, according to some embodiments;

FIGS. 16A-D are various configurations of a remote control device of the surgical robotic system, according to some embodiments;

FIG. 17 is a schematic example of a screen interface associated with the surgical robotic system, according to some embodiments;

FIGS. 18A-B are different views of a robotic device, according to some embodiments;

FIGS. 19A-B schematically illustrates a surgical robotic device including or attached to a guiding catheter driving unit, according to some embodiments;

FIGS. 20A-C are an example of an isolated mechanism of the guiding catheter driving unit, an example of a guiding catheter driving unit housing, and a guiding catheter driving unit assembled onto the robotic surgical system, according to some embodiments;

FIG. 21A-C show mechanisms for actuating rotation (roll) and/or linear movement of a tool actuated by the robotic surgical system, according to some embodiments;

FIG. 22 shows an exemplary arrangement of mechanisms driving movement of a guidewire, according to some embodiments;

FIGS. 23A-B are a schematic diagram and a flowchart pertaining to controlling a length and/or position of a tool by adjusting a curved portion of the tool, according to some embodiments;

FIG. 24 shows a system configuration defining an arrangement of tools in which a tool length can be adjusted, according to some embodiments;

FIG. 25 schematically illustrates tool-movement driving mechanisms of the system, according to some embodiments;

FIGS. 26A-B are examples of a device configuration including elastic elements (e.g. springs) for selectively engaging tools received by the system, according to some embodiments;

FIG. 27 is a schematic block diagram of a robotic device configured for manipulating two or more elongate surgical tools, according to some embodiments;

FIG. 28 schematically illustrates a robotic device for manipulation of a guidewire and a microcatheter, the guidewire extending at least in part within the microcatheter lumen, according to some embodiments; and FIG. 29 schematically illustrates a robotic device for manipulation of three or more elongate surgical tools configured for a telescopic arrangement, according to some embodiments.

DESCRIPTION OF SPECIFIC EMBODIMENTS OF THE INVENTION

The present invention, in some embodiments thereof, relates to automated actuation of elongate surgical tools inserted into a bodily lumen.

A broad aspect of some embodiments relates to a compact robotic device for manipulating movement of elongate surgical endoluminal tools which extend and curve outside of the device housing. Some embodiments described herein pertain to structural, functional and/or design features suitable for manipulating the tool using a compact sized robotic device which dimensions are not affected by the length of the tool being manipulated. In some embodiments, properties of the robotic device such as volume, weight are dictated solely by the electrical and mechanical components of the device and substantially not by the tools being manipulated.

An aspect of some embodiments relates to a compact robotic device shaped and sized to be mounted onto a patient's body and/or onto a surgical bed. In some embodiments, a volume of the device is smaller than 3000 cm^3, 2800 cm^3, 2500 cm^3, or intermediate, larger or smaller volume. In some embodiments, a weight of the device is less than 1000 grams, 850 grams, 500 grams or intermediate, larger or smaller weight.

In some embodiments, the device comprises a plurality of actuation mechanisms for moving one or more elongate surgical tools (e.g. a guidewire, a microcatheter), for example, for advancing or retracting the tool linearly, for rolling the tool. In some embodiments, a device housing encapsulates the actuation mechanisms, while walls of the housing define a plurality of entry and/or exit apertures and/or anchoring locations for the tool. In some embodiments, an anchoring location (e.g. a holder) at which a proximal end portion of the tool is coupled to the housing, and an entry aperture for a tool leading to the inner side of the housing are aligned with respect to each other along a similar horizontal or vertical axis, so that a tool segment extending between the anchoring location and the entry aperture forms a curve externally to the device housing. In some embodiments, an anchoring location and an entry aperture of a tool are defined in a similar face (or wall) of the device housing. In some embodiments, an entry aperture and an exit aperture for the same tool are configured on opposing walls of the housing, so that a tool entering the housing extends across the inner space defined by the housing, to the exit aperture.

In some embodiments, no device portions protrude outwardly from the housing, and optionally only the tools loaded onto the device extend outwardly from the housing.

In some embodiments, a maximal dimension of the robotic device housing (e.g. a width, a height, such as in a box shaped device) is a function of a distance between exit and entry apertures of a tool that curves externally to the device. The distance between the exit and entry apertures may be set, for example, in accordance with a minimal radius of curvature that the tool can withstand. In an example, a maximal dimension of the device housing is between 2-6 times, 2-10 times, 2-5 times or intermediate, higher or lower number of times a minimal radius of curvature of a tool manipulated by the device and curving outside of the housing. A potential advantage of a device housing where a maximal dimension is determined in accordance with a minimal radius of curvature of a tool that bends upon exiting and re-entering the housing may include providing for a compact, minimalized size housing. In an example, for a tool having a minimal radius of curvature of X, a minimal distance between entry and exit apertures of the tool would be 2x. In such situation, a wall of the housing through which the tool exits and enters comprises a width of, for example, 2×, 2.1×, 3×, 5× or intermediate, larger or smaller dimension.

In some embodiments, a minimal radius of curvature of an elongate tool includes a maximal bend of the tool which still allows for the tool to function, for example allows the transferring of torque along the length of the tool. In some embodiments, a minimal radius of curvature of an elongate tool includes a bend in which the tool remains intact (for example, not broken).

In some embodiments, exit and entry apertures from and to the housing are shaped to reduce or avoid friction between the tool and the edges of the aperture, for example by having a conical profile and/or rounded lip of the aperture. A potential advantage of apertures formed with no sharp edges may include reducing friction contact between the tool and the walls of the housing, which may reduce a risk of wear or tear of the tool, especially when the tool extends and curves externally to the housing, before re-entering the housing.

In some embodiments, a shape and/or size of the housing is dictated by the mechanical and/or electrical components within the housing, for example, motor(s), motor transmission (e.g. gears), tool actuation mechanisms (e.g. tool-moving elements, such as wheels). In some embodiments, the housing is sized to be as small as possible while still fully encasing the mechanical components inside it. Optionally, no mechanical components of the robotic device protrude outwardly from the housing. Optionally, no additional mechanical components from outside the housing are required for performing actuation of the tools. In some embodiments, the housing is shaped and configured so that only the elongate surgical tools extend into and out of the housing. In some embodiments, extending out of the housing comprises extending at least 1 cm, at least 2 cm, at least 4 cm or intermediate, longer or shorter distance away from a wall of the housing, such as from a wall throughout which the tool exits the housing. For example, extending of a surgical tool such as a guidewire or microcatheter at least 1 cm away from the housing.

In some embodiments, components which are integral to the housing, for example protrusions which define lips of entry and/or exit apertures of the housing, extend out of the housing to a distance of less than 1 cm, less than 0.5 cm, less than 0.3 cm, or intermediate, longer or shorter distance.

In some embodiments, a housing of the robotic device is not limited to a certain orientation, for example, so that the housing can be positioned in at least a first orientation and in a second orientation, for example where the second orientation is 90 degrees or 180 degrees to the first orientation. In some embodiments, a symmetry exists so that at least two opposing faces of the housing are similar in contour and in size, allowing for positioning the device in one of two "flipped" orientations.

In some embodiments, a plurality of pathways are defined through an inner volume of the device, where actuation mechanism(s) for driving movement of a tool received within a pathway are configured along the pathway. In some embodiments, a pathway extends between an entry aperture leading into the inner volume of the device housing, and an exit aperture leading out of the inner volume. In some embodiments, the entry and exit apertures are defined on opposing walls of the housing. In some embodiments, the device includes multiple pathways (e.g. 2, 3, 4, 6, or intermediate, larger or smaller number of pathways) for receipt of a corresponding number of elongate surgical tools, each tool received within a pathway. In some embodiments, long axes of pathways are parallel. In some embodiments, actuation mechanisms of multiple pathways are aligned side-by-side, and optionally extend along a similar axial extent. In some embodiments, no barrier (e.g. wall, shielding, drape, and the like) exists between actuation mechanisms of the multiple pathways, and the actuation mechanism share a similar space.

An aspect of some embodiments relates to a single-use robotic device for manipulation of elongate surgical tools. In some embodiments, the device is disposed (optionally along with the tools manipulated by it) following the surgical procedure. In some embodiments, the single-use device does not need to be covered by a sterile drape or cover. In some embodiments, no additional mechanical components are needed to be operably connected to the single-use robotic device for driving and/or manipulating tools loaded within the device. In some embodiments, the device is provided packaged and pre-sterilized, optionally with one or more pre-loaded tools. Additionally or alternatively, tools are loaded onto the device in the surgical room.

In some embodiments, a tool that is loaded onto the device comes in direct operable contact with one or more tool-moving elements that manipulate it. In some embodiments, one or more tool-moving elements are in direct operable contact with the one or more motors. In some embodiments, the one or more motors and the one of more tool-moving elements are encased in a single housing, and the housing, together with its content, are disposed when the clinical procedure is completed.

In some embodiments, components of the robotic device such as the tool driving assemblies, and optionally the robotic device as a whole, are disposed following use along with the tools which were manipulated by the device. A potential advantage of a disposable device may include that the tools manipulated by the device are allowed to come into direct contact and/or exist in a similar shared volume with device components, including movement driving components such as motors and/or transmission gears.

In some embodiments, no bordering element or barrier exists between the tool and its moving elements and/or driving motors within the housing. This is enabled, in some embodiments, due to that the device is disposed following use, therefore risk of contamination which may occur, for example, upon re-use, is avoided. Some potential advantages of a device in which the loaded tool may contact the device's tool-moving elements (and/or other device components, e.g. motors) directly may include simplifying use, potentially reducing loading time, and potentially improving the mechanical engagement with the tool (for example since no "bordering" elements are needed), thereby reducing or avoiding unwanted tool movements such as slippage, twisting, or kinking of the tool.

In some embodiments, no sterile barriers are required between the device actuation components and the tools manipulated by the device. In some cases, existence of the tools and device actuation components in a same shared volume may imply that during operation, fluid (e.g. blood, saline) contacted by and/or flowing within the tool may also come in contact with the device actuation components, yet a risk of contamination would be reduced or prevented since the device is supplied in a sterile state and does not require cleaning or re-sterilization following its use.

In some embodiments, the device is constructed from durable, lightweight, disposable and optionally recyclable materials, such as plastic, aluminum, steel, copper, and/or other suitable metals.

An aspect of some embodiments relates to a dual-function assembly in which both linear movement and rotational movement (e.g. roll) of an elongate tool are carried out at a same physical location. In some embodiments, the assembly is configured for linearly moving the tool while the tool is being rolled; or vice versa—rolling the tool while the tool is being moved linearly.

In some embodiments, the assembly comprises an elongate shaft with a central lumen in which the tool is received. A set of wheels are positioned adjacent the shaft and each of the wheels at least partially extends into the central lumen to operably contact the tool inside. In some embodiments, a motor which drives rotation of the wheels is mounted adjacent the wheels, for example, under the shaft. In some embodiments, rotation of the wheels pushes or retracts the tool, depending on the direction of rotation. In some embodiments, the motor which drives rotation of the wheels is configured as a part of the assembly. Alternatively, driving force is transferred to the wheels via motor transmission.

In some embodiments, the inner walls of the shaft, which define the central lumen, are contoured to match an outer contour of at least some of the wheels. In such construction, the central lumen extends into a space in between the wheels, feeding the tool into close contact with the wheels. In an example, in a 4-wheel assembly, the inner walls of the shaft may be contoured to match at least one, two, three or all four of the wheels, at the central lumen segment which is closest to a contact point where the tool contacts the wheel(s).

In some embodiments, a gear that is co-axial with the shaft is connected along the shaft and/or at a proximal or distal end of the shaft, so that upon rotation of the gear, the shaft and wheel set are rotated by the gear as a single unit, thereby rolling the tool (e.g. guidewire, steerable microcatheter) that is within the central lumen of the shaft.

A potential advantage of an assembly which drives linear and rotational movement of a tool at a same physical location (such as a specific physical location within the device housing and/or a specific location of engagement with the tool) may include reducing or avoiding unwanted tool movement such as slippage, kinking, twisting which may occur for example if two spaced apart mechanisms were to each drive linear movement and rotational movement respectively, and the tool would need to extend in between—where the unwanted movement may occur. Another potential advantage is the compact design enabled by assigning two functions, such as rotation and advancement/retraction of the tool, to the same site.

An aspect of some embodiments relates to driving rotation (roll) of an elongate tool, at two spaced apart engagement locations along the length of the tool, using the same motor. In some embodiments, the tool is engaged by elements which rotate the tool at two or more points along the length of the tool, for example, at a proximal portion of the tool (e.g. adjacent a handle of the tool), and at a more distal portion. In an exemplary construction, a first gear rotates a holder which holds a proximal portion of the tool; rotation of the first gear then rotates a second gear which is a part of the linear movement assembly (such as described herein), where the second gear rotates a shaft in which a more distal portion of the tool is received. In such arrangement, actuation of a single motor drives rotation of both the first and second gears, generating rotation (roll) of the tool at both engagement locations.

A potential advantage of driving rotational movement at two spaced apart engagement locations along the length of the tool using a single motor may include improved control over the tool, for example as compared to use of two different motors for driving rotation at the two locations, where actuation timing and/or speed and/or direction of the two motors would need to be synchronized to ensure uniform roll of the tool along its length.

In some embodiments, one or more tools which are manipulated by the device are engaged and manipulated only from their proximal portion (e.g. from a tool handle); while one or more additional tools are engaged at a more distal segment thereof (i.e. not from the tool handle).

An aspect of some embodiments relates to controlling a usable length of an elongate surgical tool by modifying a size of a curve of the tool outside of the robotic device. In some embodiments, a tool manipulated by the device extends in a curved manner (bends) outside of the housing one or more times. In some embodiments, when a length of a more distal segment (e.g. a tool segment extending between an exit aperture from the device housing and a target within the patient's body) changes, the curve is expanded or contracted in size. In some embodiments, a tool passes into and out from the device housing several times, forming more than one curve outside the housing. For example, a guidewire is curved twice—once independently, optionally between a proximal handle and a more distal portion, and a second time while being received within a lumen of a curved microcatheter. In some embodiments, the curve is a "U" shaped curve, which can be modified, for example, by lengthening or shortening a distance of a maximal point of the "U" shape relative to the closest wall of the device housing.

The invention, in accordance with some embodiments, relates to automated devices for inserting an elongate surgical medical tool into a bodily lumen, and more specifically to body-mountable automated devices for inserting elongate surgical medical tools, such as guidewires and microcatheters into blood vessels.

Many medical procedures, such as catheterization for diagnostic and/or therapeutic purposes, require insertion of a catheter into the patient's blood vessels and other body lumens.

Typically, the physician first inserts a guidewire into an artery, such as the femoral artery, or a vein, and navigates it through the torturous vasculature until it reaches the target, which may be the heart, an artery, a peripheral blood vessel, the brain etc. Once properly positioned, the physician places a catheter over the guidewire, and pushes the catheter until it too reaches the target. In some cases, the procedure requires use of a small radius catheter, typically known as a microcatheter. In such cases, the physician may insert the microcatheter directly, without use of a guidewire. Manual insertion and navigation of guidewires/microcatheters through the torturous vasculature is not only challenging for the physician, but it may also be hazardous to the patient, as even subtle erroneous movements may result in unintentional perforation of the blood vessel wall. Further, manual procedures require the physician and additional medical personnel to be present at the procedure room during the entire procedure. Since most invasive procedures are done under imaging, such as X-ray, CT, etc., the medical personnel, as well as the patient, are exposed to radiation.

Remotely manipulated automated (robotic) devices have been developed in recent years, however, existing robotic devices are cumbersome and expensive. Therefore, there is a need for a small, inexpensive and easy to use automated device for inserting guidewires and/or microcatheters into bodily lumens, such as blood vessels, and navigating therethrough to a target region.

According to some embodiments, the insertion device may include a power source. In some embodiments, the power source may be a battery, a power supply, and the like. In some embodiments, the battery is disposable. In some embodiments, the battery is reusable. In some embodiments, the battery is rechargeable. In some embodiments, the power supply may be directly or indirectly connected to mains power. In some embodiments, insertion device may include one or more printed circuit boards (PCBs), configured to relay/process/convey instructions and/or electrical connection between various components of the device.

According to some embodiments, the insertion device may allow the linear and/or rotational advancement/movement of the medical instrument. In some embodiments, the insertion device may be configured to automatically advance the insertion device and/or further automatically allow the rotational movement thereof by rotating the insertion device. In some embodiments, when the medical tool is a guidewire, the insertion device may allow controlling the linear and/or rotation and/or tip parameters of the guidewire. In some embodiments, when the medical tool is a guidewire, the insertion device may allow automatically and/or remotely controlling the linear and/or rotation and/or tip parameters of the guidewire. In some embodiments, the medical instrument may be preloaded onto the medical device, prior to being used for a medical procedure. In some embodiments, the medical instrument may be preloaded onto the medical device, prior to being placed on the subject's body.

According to some embodiments, there is provided an insertion device configured to remotely and automatically linearly advance one or more medical tools (such as a guidewire and catheter) into and within bodily lumens, such as blood vessels, for endovascular procedures, including coronary, peripheral and cerebral endovascular procedures. In some embodiments, the insertion device is configured to further automatically and/or remotely control/allow the rotational movement of the one or more medical tools. In some embodiments, the insertion device is further configured to control parameters of the one or more medical tools, such as, tip stiffness. In some embodiments, the device is configured to control a force applied by a distal tip of the tool, for example by controlling one or more of: speed of advancement of the tool, a stiffness of the tool. Optionally, the tool is manipulated such that its distal tip applies a constant force or a varying force onto structures encountered by the tip (e.g. tissue such as a vessel wall).

According to some embodiments, there is provided an insertion device configured to remotely and automatically linearly advance one or more medical tools (such as a guidewire and catheter) into and within bodily lumens, for various endoluminal procedures. According to some embodiments, when the first tool is a guide wire and the second medical tool is a catheter, the insertion device may allow the linear, rotational and/or tip parameters control of the guidewire, and the linear motion (over the guidewire) of the catheter, and rotation motion thereof (relative to the insertion device).

According to some embodiments, the linear velocity of advancement of the medical instrument may be in the range of about 0-100 mm/sec or any subranges thereof. In some exemplary embodiments, the linear velocity of the medical instrument may be in the range of about 0-50 mm/sec, 1-100 mm/sec, 5-50 mm/sec or intermediate, higher or lower velocity. The velocity may be constant and/or in varying increments and may be adjusted (manually and/or automatically), during the procedure. In some embodiments, the velocity may be in the range of about 0-25 mm/sec with increments of about 0.1 mm/sec. In some embodiments, the velocity may be in the range of about 25-50 mm/sec with increments of about 1 mm/sec. In some embodiments, the position holding stability at actuator is about 0.1 mm. According to some embodiments, the rotational movement may be in anywhere in the range of 360 degrees.

According to some embodiments, the rotational movement may be continuous in the range of 360 degrees. In some embodiments, the number of full revolutions may be limited. In some embodiments, the number of full revolutions may be limited to about 5-10 revolutions in each direction from the neutral (starting) setting.

According to some embodiments, the rotation position resolution may be in increments of 1-5, 0.5-10 degrees, 0.1-1 degrees or intermediate, higher or lower resolution. In some exemplary embodiments, the rotational position resolution may be about +/−2 degrees, +/−1 degree, +/−0.5 degrees or intermediate, higher or lower resolution.

According to some embodiments, the controller of the device may be a remote controller. In some embodiments, the controller of the device may be integrated with the device. In some embodiments, the controller of the device may be connected by wired or wireless means. In some embodiments, the controller may be configured to allow control over the operation of the medical device. In some embodiments, the controller may be configured to allow control of advancement of the medical instrument, including, but not limited to: linear direction of advancement, velocity of advancement, increment of advancement, rotational movement, degree of rotational movement, and the like or any combination thereof. In some embodiments, the controller may include one or more operating buttons. In some embodiments, the buttons may include pressure buttons, slider buttons, joystick, and the like, or any combination thereof. In some embodiments the system may have means for injecting a contrast agent into the lumen, e.g., the vasculature. The injection mechanism may be remotely operated, so as to allow the surgeon/physician to perform the entire procedure from a remote location. In some embodiments, the system may be configured to control linear and/or rotational movements of a guiding catheter, if used in the procedure.

As referred to herein, a "robotic device" or "device" may refer to the device housing inclusive of mechanical and/or electrical components accommodated inside the housing. In some embodiments, the "device" is not meant to cover add-ons or external components such as a guiding catheter driving unit (when coupled externally to the housing and not integrated in it), a mounting of the device, a remote control of the device, and the like.

As referred to herein, an "assembly" or "actuation assembly" may include tool-moving elements, such as wheels, and/or a coupling for the tool, such as an elongate shaft in which the tool is received. In some embodiments, an "assembly" or "actuation assembly" further comprises one or more motors and/or transmission (e.g. gears) which transfer force from one or more motors external to the assembly.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 1:
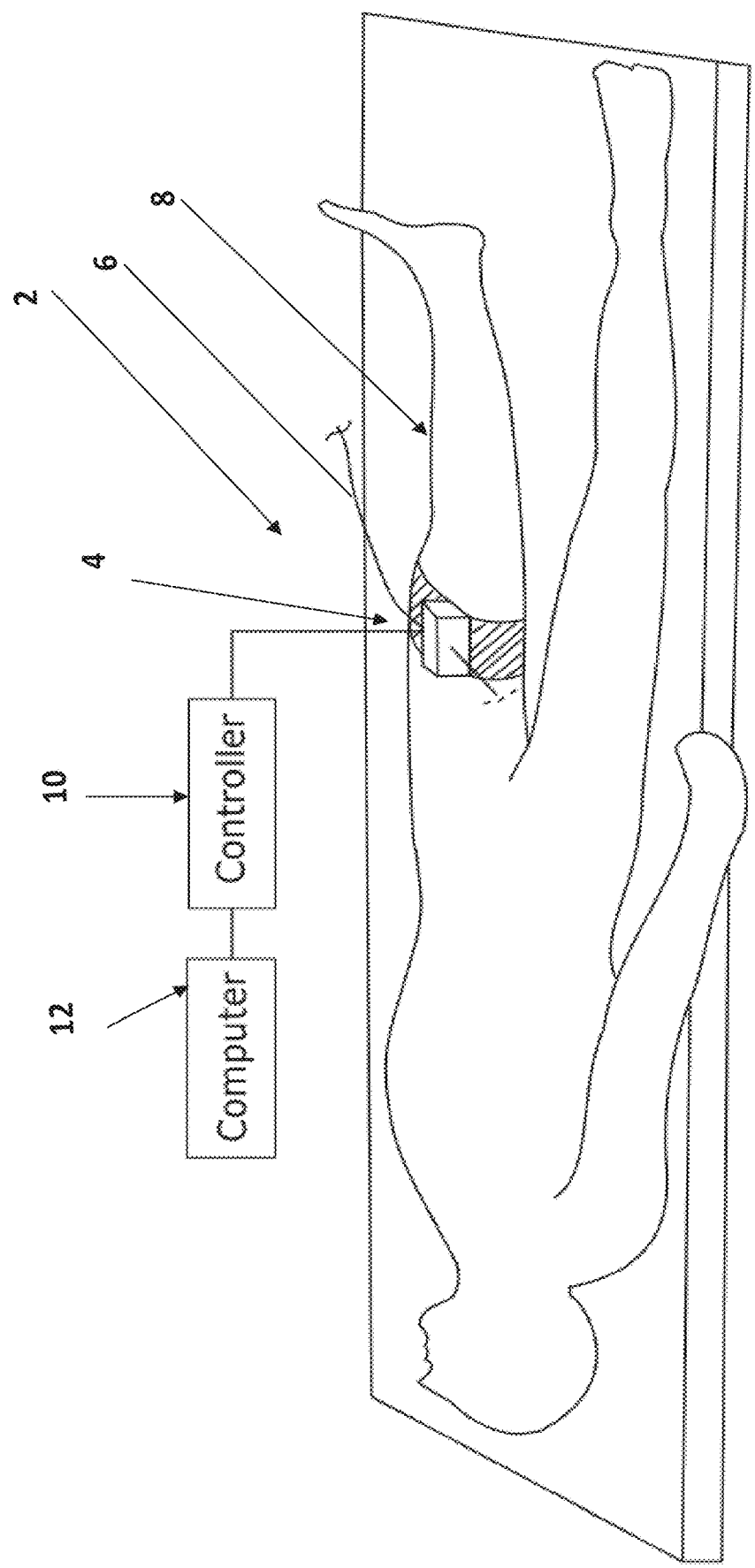
FIG. 1 shows a schematic diagram of a medical system comprising an insertion device secured to a subject's body, according to some embodiments.

Reference is made to FIG. 1, which shows a schematic diagram of an exemplary medical system, according to some embodiments. As illustrated in FIG. 1, system 2 includes a body-mountable miniature automated insertion device 4, configured to insert a medical instrument, such as a guidewire 6, into a subject's 8 lumen (such as, a blood vessel). According to some embodiments, depending on the location of the target tissue (for example, the heart, a peripheral blood vessel in the lower extremities, brain, liver, and the like) and the purpose of the procedure, the entry point may be selected from, but not limited to, at the patient's groin (i.e., the femoral artery), arm (i.e., the radial artery) or neck (i.e., the jugular vein). Accordingly, the location of the insertion device 4 on the patient's body may vary. In the example shown in FIG. 1, the device is attached to, the patient's thigh, to allow access to the patient's femoral artery. It can be appreciated that the device may additionally or alternatively be attached to the patient's arm, or any other desired location on the patient's body, depending on the selected entry point. According to some embodiments, the device may be attached/mounted/secured to the patient's body using any suitable attachment element. For example, the device may be attached to the patient's body using a band, which can be pulled over the patient's leg up to his/her thigh. The band may be flexible, such that it stretches according to the circumference of the thigh, or it may be substantially rigid or semi-flexible and include a length-adjusting mechanism. Alternatively, one or more straps may be wrapped around the patient's thigh directly. Such straps may be substantially rigid or semi-flexible, having a length-adjusting mechanism, and provided with connectors (e.g., buckles) at their opposite ends, for fastening the straps and securing them to the patient's thigh. The bands/straps may include one or more sensors, such as force sensor, disposed thereon.

According to some embodiments, the insertion device is not body mountable, but configured for positioning in close proximity to the patient's body, e.g., using a robotic arm, a base structure configured for securing to the patient's bed, etc.

In some embodiments, the insertion device may be disposable, either partially, such that some of its components are discarded and replaced between procedures, or entirely, such that the entire insertion device is disposed of once the procedure has been completed, i.e., a single-use device. In other embodiments, the insertion device may be reusable, such that it can be used repeatedly with new medical instruments (e.g., guidewires and/or catheters).

In some embodiments, the device may be configured such that it can be used to insert into bodily lumens a variety of different medical instruments, of varying lengths and diameters, including, for example, guidewire, catheter, microcatheters, and the like. In some exemplary embodiments, without limitation, the device may be adapted to insert into a blood vessel, a guidewire such as that disclosed in co-owned U.S. Patent 15 U.S. Pat. No. 9,586,029, titled "Guidewire Having Selectively Adjustable Stiffness and Tip Curvature", and/or in co-owned U.S. Patent Application Publication No. US 2018/214,675, titled "Double Concentric Guidewire", both to Shekalim et al, and incorporated herein by reference in their entireties.

According to some embodiments, the system may further include a controller 10 for controlling the operation of the device, in particular, the insertion and/or steering of the medical instrument/s (such as, a guidewire and/or a catheter) toward the target (e.g., heart chamber, blocked artery, etc.). The controller 10 may be coupled to the insertion device 4 via a wired connection or a wireless connection, and it may be either manually operated by a physician (for example, the controller may be in a form of a joystick), or automatically operated using a dedicated software. In the latter case, the system may further comprise a computer 12, which may include at least one processor, user interface and a display. The computer 12 may be a personal computer (PC), a laptop, a tablet, a smartphone or any other processor-based device. In some embodiments, the controller 10 is disposable. In some embodiments, the controller 10 is reusable.

In some embodiments, the controller 10 is configured to interact/couple to more than one insertion device.

In some embodiments, the system 2 may further include an imaging device, or it may be used in conjunction with an imaging device. The utilized imaging modality may be any one of X-ray fluoroscopy, CT, cone beam CT, CT fluoroscopy, MRI, ultrasound, or any other suitable imaging modality. According to some embodiments, the insertion device may be capable of advancing the medical instrument linearly within the bodily lumen. In some embodiments, the device may further be capable of rotating the medical instrument within the lumen alternatively or in addition to linearly advancing the medical instrument. In some embodiments, the device may further be capable of rotating the medical instrument within the vessel separately and/or also simultaneously, while linearly advancing the medical instrument. For example, in some exemplary embodiments, the insertion device may be capable of advancing a guidewire and/or catheter linearly within the blood vessel. In some embodiments, the device may further be capable of rotating a guidewire and/or catheter within the vessel alternatively or in addition to linearly advancing the guidewire and/or catheter. In some embodiments, the device may further be capable of rotating a guidewire and/or catheter within the vessel separately and/or also simultaneously, while linearly advancing the guidewire and/or catheter. According to some embodiments, as further exemplified herein, the insertion device is configured to allow the linear advancement of the medical instrument within the bodily lumen along with the rotational movement thereof, by utilizing one or more actuators that further advantageously enable the smooth movement of the medical instrument, without deforming the medical instrument (i.e., without forming tension or twists along the length of the medical instrument). According to some embodiments, as further exemplified herein, the linear and rotational movements of the medical instrument (such as a guidewire and/or microcatheter) may be generated by separate actuators, or by one or more dual-purpose actuators, configured to allow both rotational and linear movement of the instrument/s.

Figure 2A:
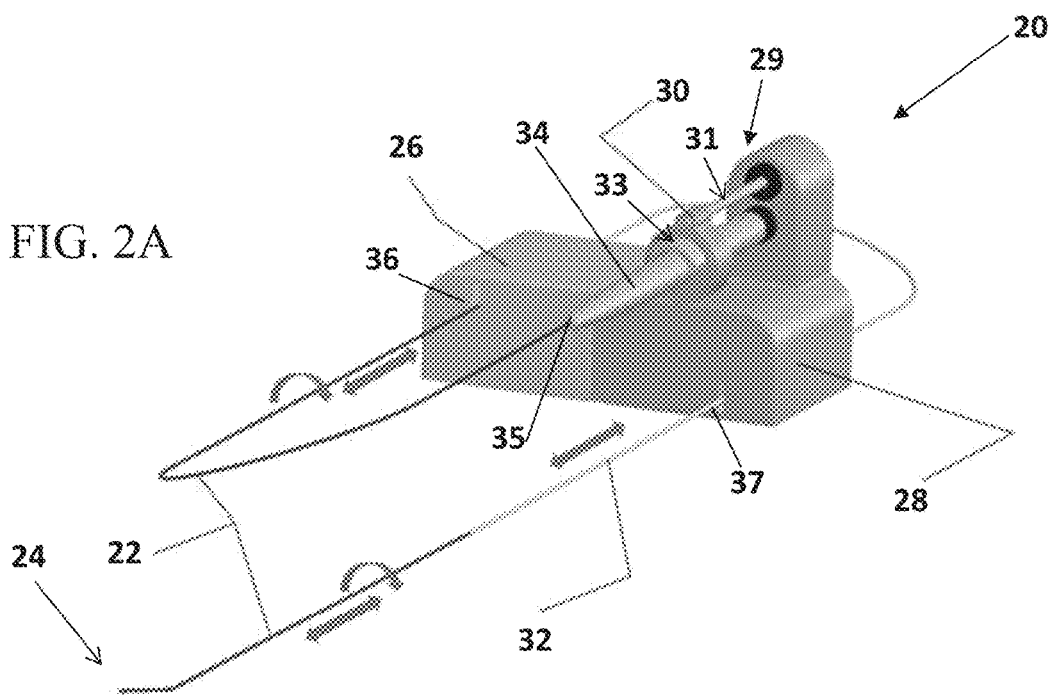
FIGS. 2A-2B illustrate schematic perspective views (front and rear, respectively), of an insertion device, according to some embodiments.
Figure 2B:
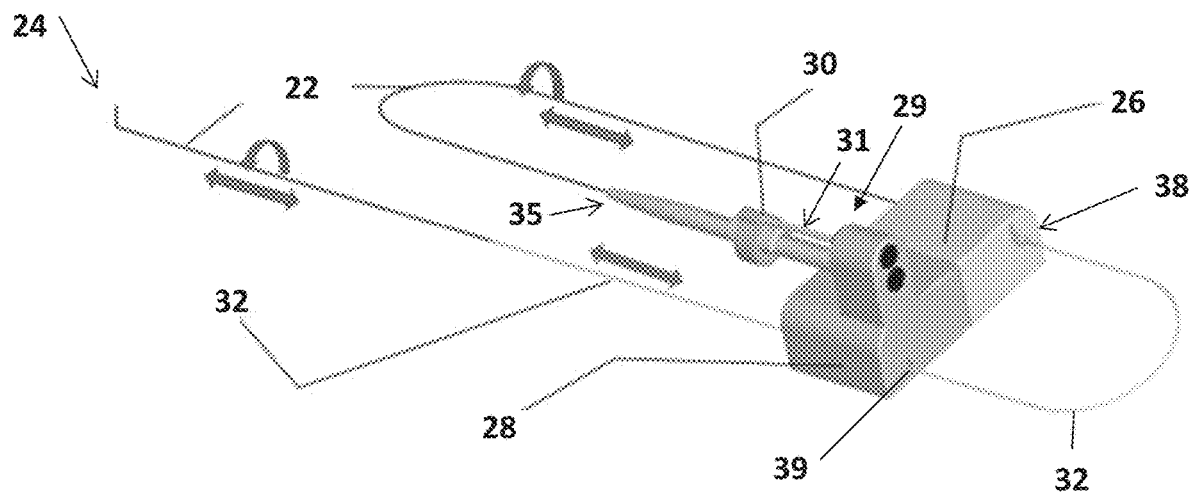

Reference is now made to FIGS. 2A-2B, which illustrate schematic perspective views (front and rear, respectively), of an insertion device, according to some embodiments. As shown in FIG. 2A, insertion device includes elements for advancing a first medical instrument (shown as guidewire 22), in a linear direction and optionally in rotational direction (as indicated by the movement arrows). As illustrated in FIG. 2A, the proximal end of the guidewire 22 may be secured to a dedicated holder 34, that may further allow control over tip parameters of the guidewire 22, as described below. The guidewire 22 advances from a first opening 35 in the holder (on the front face of the device 20), to enter the insertion device 20 via a second opening 36, and re-exit the device 20 from a different opening (first rear opening (not shown)) at the rear (back) face of the device 20. The guidewire 22 can then re-enter the insertion device 20 through another opening (second rear opening (not shown)) at the rear face of the device 20, and can re-exit the insertion device 20 from a third (front) opening 37, such that the distal end 24 of the guidewire 22 after exiting the third opening 37 can be configured to be inserted into a body of a subject, more particularly to a bodily lumen, such as a blood vessel.

In some embodiments, as illustrated in FIG. 2A, the guidewire 22 exits the insertion device 20 into the lumen of a second medical instrument (shown as catheter 32), which can be connected/attached/associated with the first rear opening, re-enter the insertion device 20 via the second rear opening and exit the front face of the insertion device 20 via the third front opening 37. In some embodiments, the second medical instrument is configured to be inserted into the bodily lumen. In some embodiments, the second medical instrument (such as, catheter 32) may be inserted into the bodily lumen together with and/or following the advancing of the first medical instrument (e.g., guidewire 22) by the automated medical device 20. The above-described winding path of the guidewire 22 and/or the catheter 32 enables a compact spatial arrangement (e.g., side by side) of the movement control units (described below), thus minimizing the device's overall size. In some embodiments, pathways (e.g. shafts) through which the tools extend inside the housing are aligned side by side, and are optionally parallel to each other. A lateral alignment in which the movement actuation mechanisms are positioned substantially side by side may provide for a smaller device size, such as a thinner device width.

The small size of the device allows, in some embodiments, positioning of the device on the subject's body.

In some embodiments, the medical device 20 includes one or more actuators/elements configured to allow the linear and/or rotation movement/advancement of the medical instrument/s. In some embodiments, as illustrated in FIG. 2A, device 20 includes a first movement control unit 26 configured to allow linear and/or rotational movement of the guidewire 22. The first movement control unit 26 may include one or more actuators/motors allowing the movement of the guidewire 22, as further detailed herein below. Device 20 may further include a second movement control unit 28) configured to allow linear and/or rotational movement of the catheter 32. The second movement control unit 32 may include one or more actuators/motors allowing the movement of the catheter 32, as further detailed herein below.

Optionally, device 20 may further include at least one additional movement control unit, for example, in instances in which the guidewire is comprised of a hollow outer wire and an inner wire disposed within a lumen of the outer wire, as disclosed, for example, in abovementioned U.S. Patent Application Publication No. US 2018/214,675. In such instances, an additional movement control unit 29 may be used to allow the controlling of the movement of the inner wire of the guidewire 22 relative to the outer wire of the guidewire 22, to control tip parameters of the guidewire 22, such as stiffness and/or curvature. The movement of the inner wire relative to the outer wire may be achieved by means of an adjuster/slider 33 attached to the inner wire, a non-rotating nut 30 and a lead screw 31 threaded therein. Rotation of the screw 31 by a motor/actuator causes linear movement of the nut 30 along the length of the lead screw 31, which in turn causes linear movement of the adjuster/slider 33 and the inner wire attached thereto. In some embodiments, the movement control unit 29 may allow one or more of the following relative states between the inner and outer wires of the guidewire 22: 1) the distal tip of the inner wire extends distally beyond the distal tip of the outer wire, 2) the distal tip of the inner wire is translated proximally such that it resides within the outer wire (i.e., the distal tip of the outer wire extends beyond the distal tip of the inner wire, and/or 3) the distal tips of the inner and outer wires are aligned. In some embodiments, rotation of the guidewire 22 and the holder 34 to which it is attached, at its proximal end, may be controlled by the movement control unit 26. In some embodiments, in order to ensure that the holder 34 smoothly rotates together with guidewire 22, so as to prevent twisting/kinking of the guidewire 22 (as the guidewire 22 may not be able to rotate relative to the holder 34), the movement control unit 29 may include an additional actuator/motor, e.g., coupled to the proximal end of the holder 34, to further control the rotation of the holder 34.

Reference is now made to FIG. 2B, which shows a perspective rear view of insertion device 20. As shown in FIG. 2B, insertion device 20, includes elements/units for advancing a first medical instrument (shown as guidewire 22), in a linear direction and optionally in rotational direction (as indicated by the movement arrows). As illustrated in FIG. 2B, the proximal end of the guidewire 22 may be secured to a dedicated holder 34. The guidewire 22 may advance from the first opening 35 in the holder 34 (on the front face of the device), to enter the insertion device 20 via a second opening (not shown in FIG. 2B), and re-exit the device 20 from a first rear opening 38 at the rear (back) face of the device 20. The guidewire 22 may then re-enter the insertion device 20 through a second rear opening 39 at the rear face of the device 20, and then re-exit the insertion device 20 from a third (front) opening (not shown in FIG. 2B), such that the distal end 24 of the guidewire 22, after exiting the third opening, may be configured to be inserted into a body of a subject, more particularly to a bodily lumen, such as a blood vessel.

In some embodiments, as illustrated in FIG. 2B, the guidewire 22 may exit the insertion device 20 from the first rear opening 38 into the lumen of a second another medical instrument (shown as catheter 32), which may be connected/attached/associate with the first rear opening 38, re-enter the insertion device 20 via the second rear opening 39 and exit the front face of the insertion device 20 via the third front opening. In some embodiments, the second medical instrument 32 is configured to be inserted into the bodily lumen. In some embodiments, the second medical instrument (such as, catheter 32) may be inserted into the bodily lumen together with and/or following the advancing of the first medical instrument (e.g., guidewire 22) by the automated medical device.

Figure 3A:
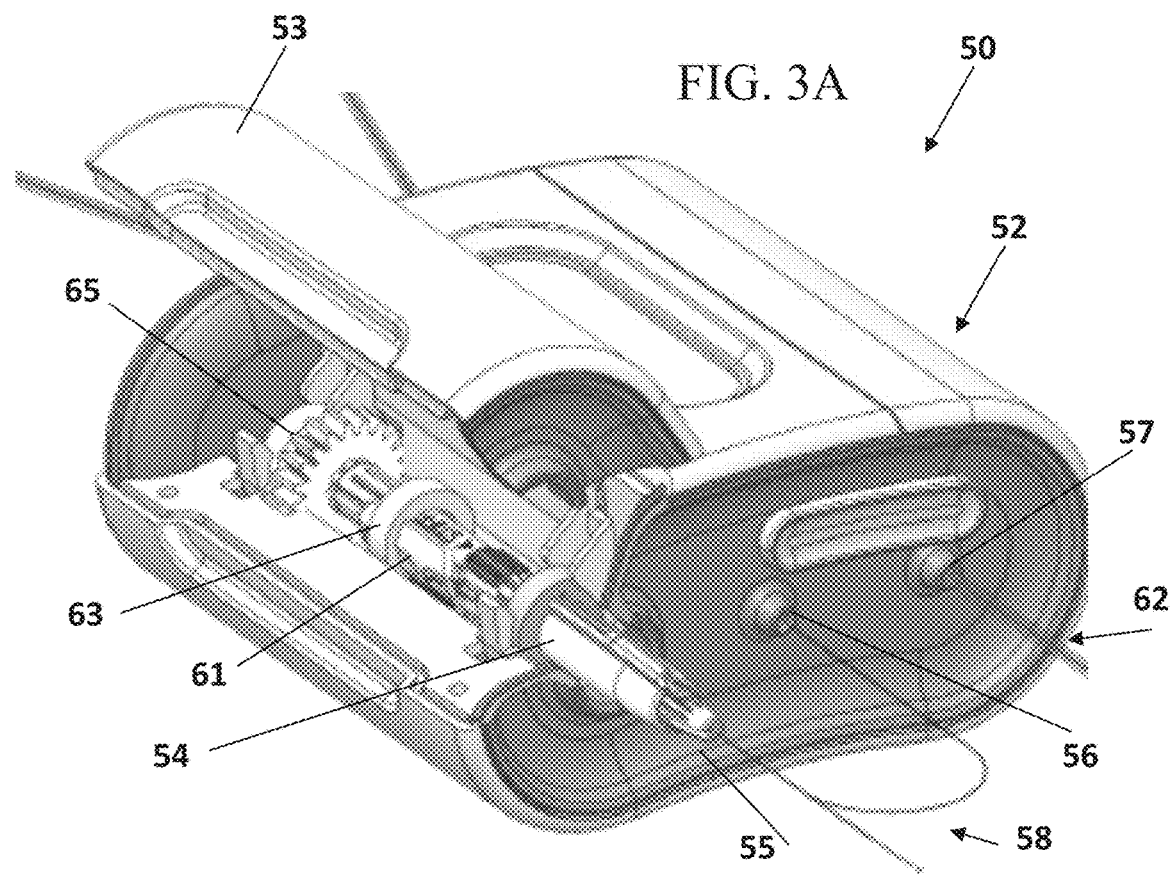
FIGS. 3A-3B illustrate schematic perspective views of an insertion device, according to some embodiments.
Figure 3B:
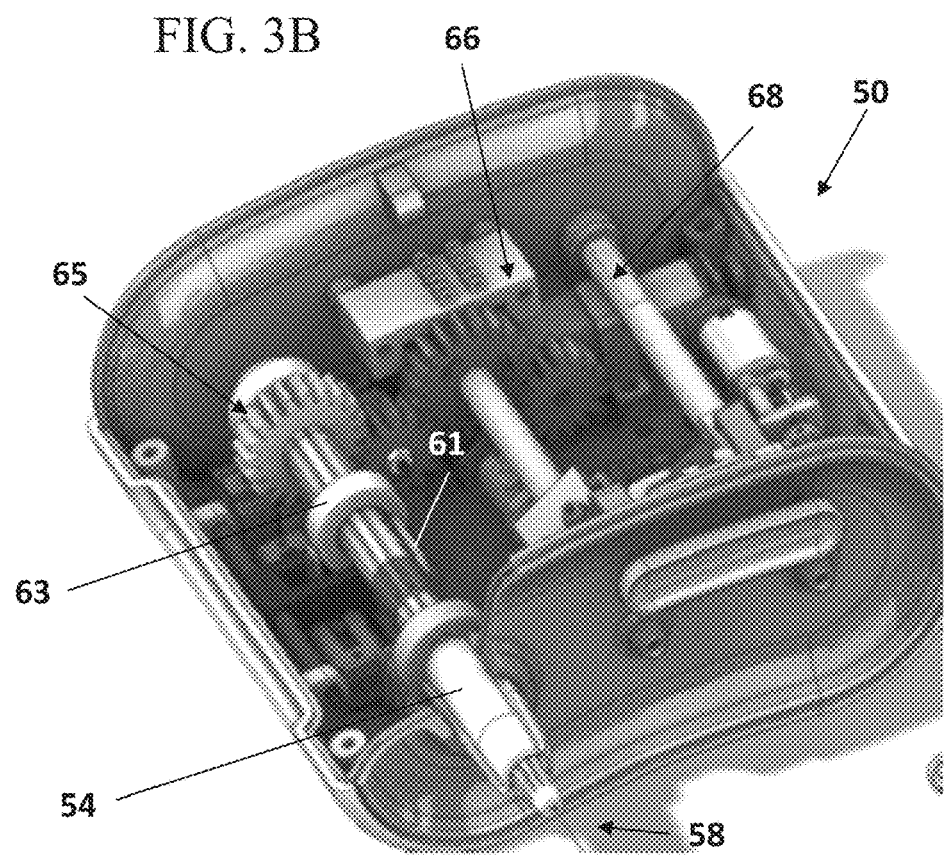

Reference is now made to FIGS. 3A-3B, which illustrate schematic perspective top views, of an insertion device, according to some embodiments. As shown in FIG. 3A, insertion device 50 includes a casing 52 and a top cover 53, which is shown in an open configuration. Further shown is a holder 54 which holds the proximal end of the guidewire 58 and may further allow, in some embodiments, to adjust the tip parameters of the guidewire 58. In some embodiments, the top cover 53 is intended to allow access 14 to the holder 54, such that the holder 54, with the guidewire 58 attached thereto, may be inserted into and/or removed from the casing 52. As shown in FIG. 3A, the guidewire 58 may advance from a first front opening 55 in the holder 54, to enter the casing 52 via a second front opening 56, and re-exit the casing 52 from a first rear opening (not shown)) at the rear face of the casing. The guidewire 58 can then re-enter the casing through a second rear opening (not shown) on the rear face of the casing 52, and re-exit the casing 52 from a third front opening 57. In some embodiments, as illustrated in FIG. 3A, the guidewire 58 exits the first rear opening of the casing 52, while being threaded within the lumen of another medical instrument (shown as catheter 62), which may be connected/attached/associated with the first rear opening, re-enter the casing 52 via the second rear opening and exit the front face of the casing 52 via the third front opening 57. In some embodiments, the second medical instrument 62 is configured to be inserted into the bodily lumen. In some embodiments, the second medical instrument (such as, catheter 62) may be inserted into the bodily lumen together with and/or following the advancing of the first medical instrument (e.g., guidewire 58) by the automated medical device, i.e. the guidewire 58 may serve as a rail on which the catheter 62 rides.

The above-described winding path of the guidewire 58 and/or the catheter 62 enables a compact spatial arrangement of the movement control units of the device 50, as described below, thus minimizing the device's overall size. The small size of the device allows, in some embodiments, positioning of the device 50 on the subject's body. In some embodiments, the medical device includes one or more actuators/elements/units configured to allow the linear and/or rotation movement/advancement of the first and second medical instruments.

Reference is made to FIG. 3B, which schematically illustrates the medical device of FIG. 3A, with the top cover 53 and a top portion of the casing 52 removed. As illustrated in FIG. 3B, the device 50 may include a first movement control unit 66 configured to allow linear and/or rotational movement of the guidewire 58. The device 50 may further include a second movement control unit 68, configured to allow linear and/or rotational movement of the catheter. The first movement control unit 66 and the second movement control unit 68 may include one or more: actuators/motors, gears, racks shafts, rotational screws, allowing the movement (linear and/or rotational) of the guidewire and/or catheter, respectively, as further detailed herein below. In some embodiments, the device 50 may include one or more additional movement control units. For example, in instances in which the guidewire is secured at its proximal end to a holder 54, the device 50 may further include a movement control unit having at least a motor/actuator and a gear 65 which control the rotation of the holder 54 about its axis.

As shown in FIG. 3B, in instances wherein the guidewire 58 includes a hollow outer wire and an inner wire disposed within the lumen of the outer wire, the device may include an additional movement control unit comprised of a non-rotating nut 63 attached to an adjuster/slider 61 of the holder, which is rigidly attached to the proximal end of the inner wire, and a lead screw (not shown) threaded within the nut 63, to allow the controlling of the movement of the inner wire relative to the outer wire, thus controlling the tip parameters of the guidewire (such as, adjusting the stiffness and/or curvature thereof). Rotation of the lead screw by a motor/actuator (not shown) causes linear movement of the nut 63 along the length of the lead screw, which in turn causes linear movement of the adjuster/slider 61 and the inner wire attached thereto.

In some embodiments, one or more of the following relative states between the inner and outer wires of the guidewire may be enabled by the above movement control unit: 1) the distal tip of the inner wire extending distally beyond the distal tip of the outer wire, 2) the distal tip of the inner wire being translated proximally so as to be disposed within the outer wire (i.e., the distal tip of the outer wire extending beyond the distal tip of the inner wire, and/or 3) the distal tips of the inner and outer wires being aligned.

Figure 4A:
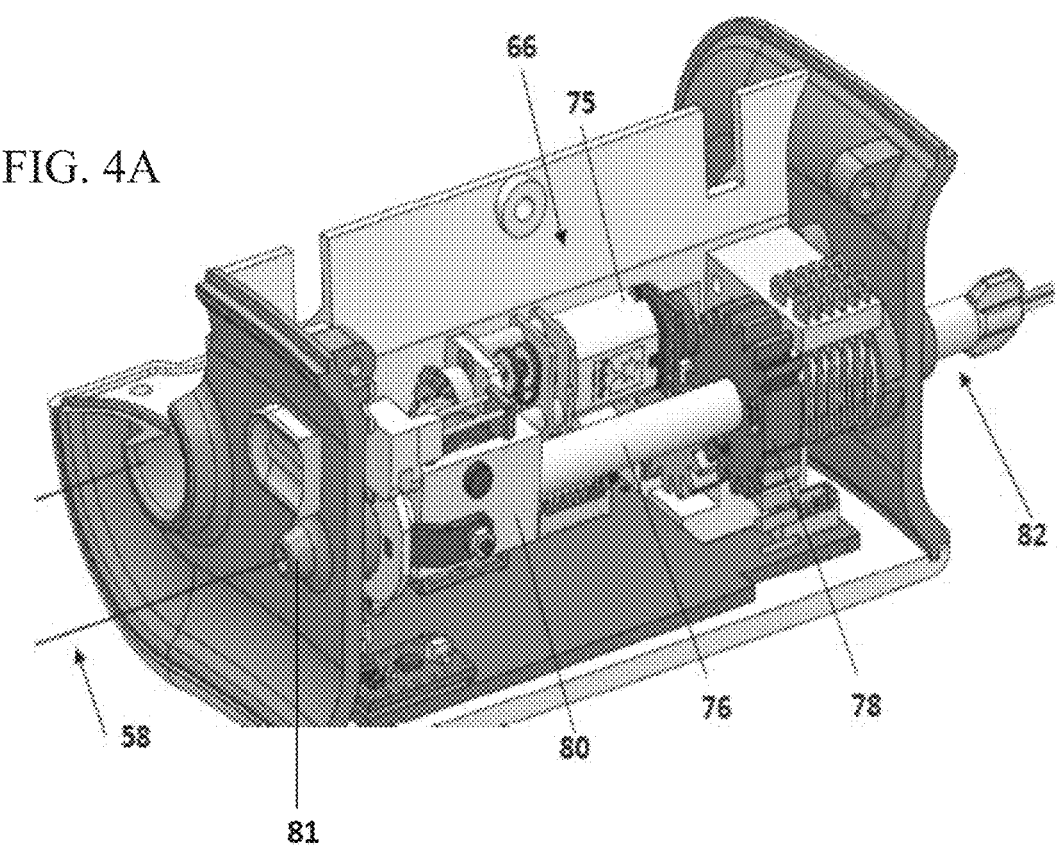
FIGS. 4A-4B show schematic perspective cross-sectional views of the insertion device shown in FIGS. 3A-3B, according to some embodiments.
Figure 4B:
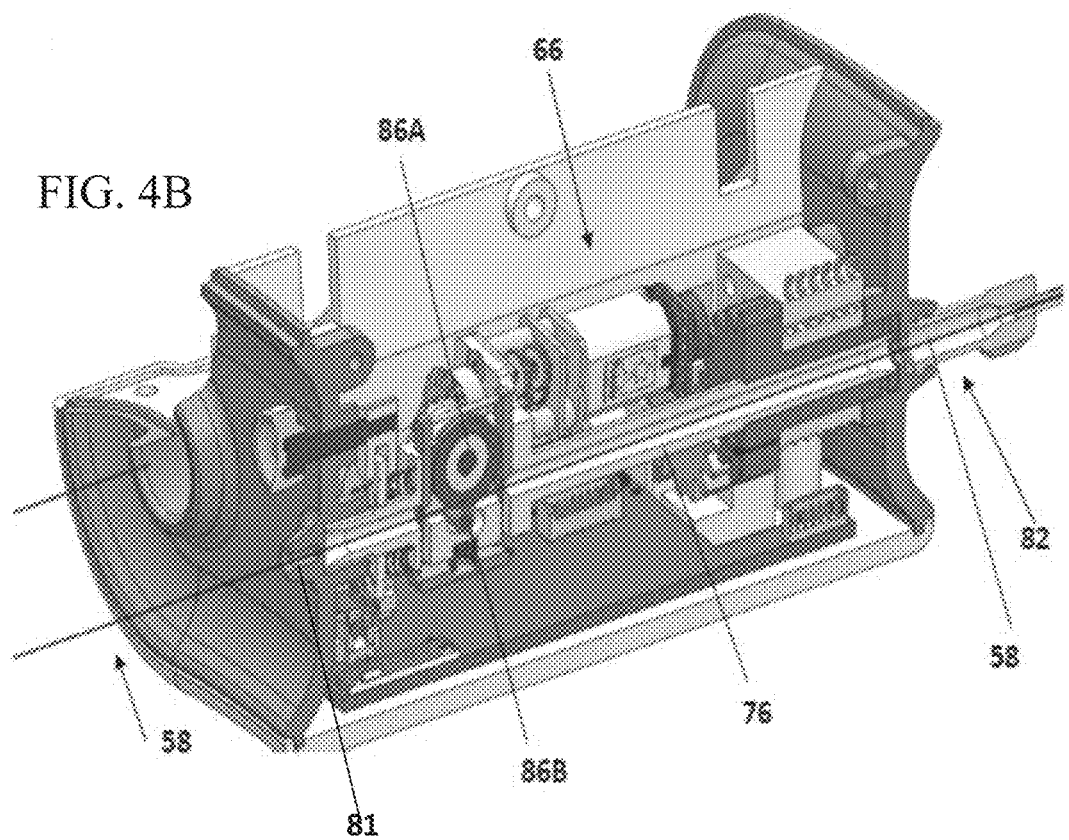

Reference is now made to FIGS. 4A-4B, which show perspective views of cross sections of the insertion device of FIGS. 3A-3B, according to some embodiments. Shown in FIG. 4A, is a longitudinal cross-section view of insertion device 50 (illustrated in FIGS. 3A-3B), cross sectioned at a line between the first movement control unit (66 in FIG. 3B), and the second movement control unit (68 in FIG. 3B). As shown in FIG. 4A, the first movement control unit 66 includes at least one motor (shown as motor 75), a shaft 76, through which the first medical instrument (shown as guidewire 58) is moved. Also shown are gears (such as exemplary gear 78). In addition, movement element 80 is indicated. As further elaborated below, movement element 80 includes at least two opposing round discs/wheels/rings placed one above the other and/or placed on adjacent the other and having a space therebetween, such that the medical instrument (shown as guidewire 58) is located in this space.

Further shown in FIG. 4A is the rear end opening 82, through which the guidewire 58 can exit the device, for example into a catheter lumen, which is configured to be connected to the rear end opening. Reference is now made to FIG. 4B, which illustrates a longitudinal cross section of the first movement control unit 66.

As shown in FIG. 4B, the movement element 80 includes two opposing spinning wheels/discs/rings (86A, 86B), placed one over the other and/or one adjacent the other, with a space therebetween. In the space formed between the wheels, guidewire 58 is located, such that upon spinning of the wheels (which is actuated, for example, by various interconnected gears), linear movement of the guidewire 58 within the shaft 76 towards the rear opening 82 is facilitated. By controlling the velocity of the spinning, the velocity of advancement of the guidewire 58 may be controlled. In some embodiments, the movement control unit 66 and/or the movement element 80 may be rotated along a longitudinal axis, thereby further allowing the rotational movement of the guidewire 58. In some embodiments, the wheels may be similar or different in size, shape, stiffness, material or composition.

As can be further observed in FIGS. 4A-B, in some embodiments, an aperture through which a tool passes into and/or out of the housing is structured to reduce friction between the tool and the walls of the housing. For example, aperture 81 (through which guidewire 48 re-enters the housing) defines a conically shaped protrusion ending with a rounded lip. A potential advantage of an aperture of the housing being formed with a rounded shape and no sharp corners may include reducing friction between the tool and the walls of the housing, thereby potentially reducing a risk of tear or wear of the tool (e.g. due to the tool rubbing against the wall). This may be especially advantage for devices such as described herein, in which the tool extends and curves outside of the housing, and may therefore be more prone to touching the aperture walls, for example as compared to tool which is held solely along a single straight linear axis.

Figure 5:
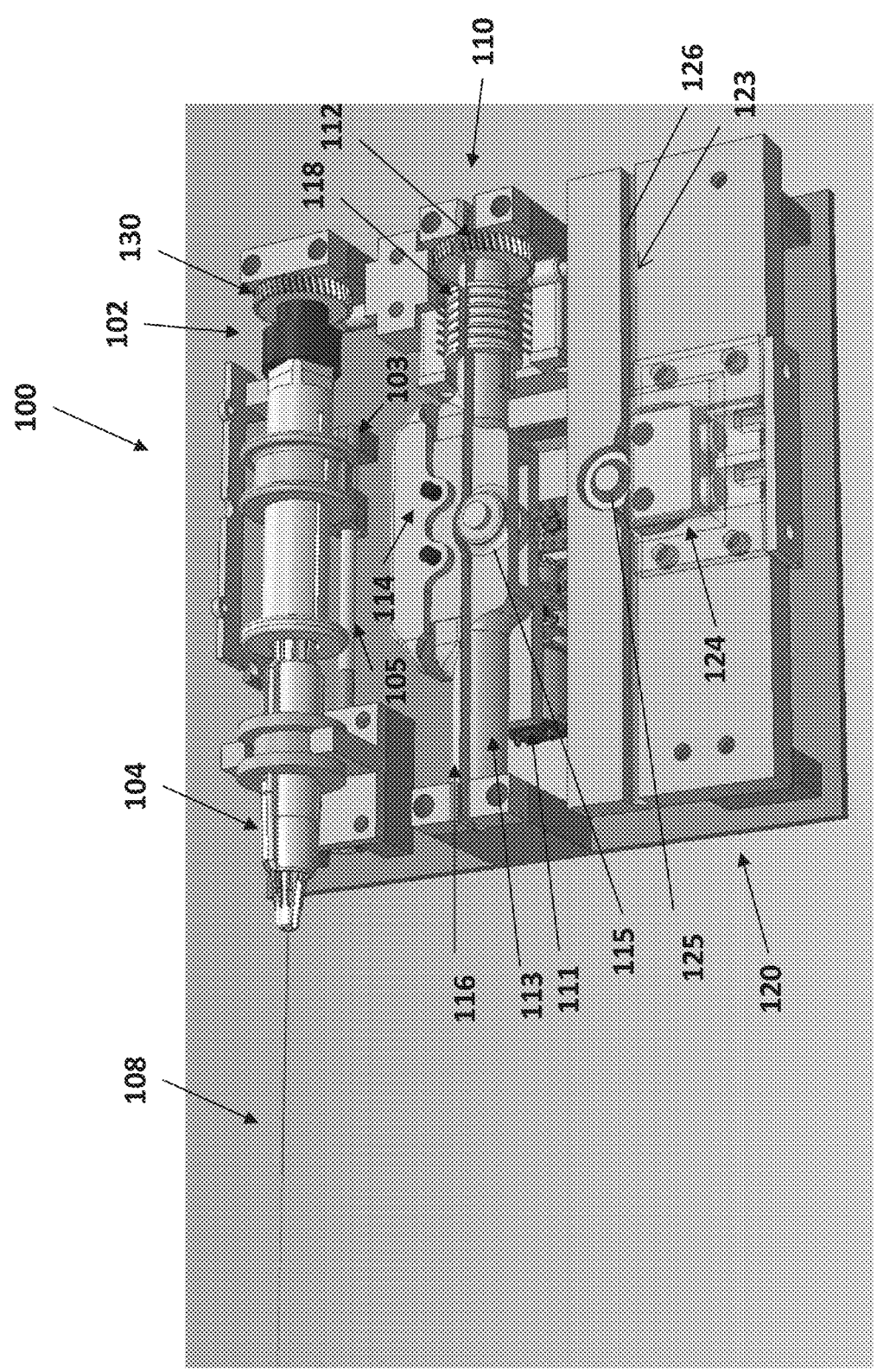
FIG. 5 illustrates a schematic perspective top view of movement control units of an insertion device, according to some embodiments.

Reference is now made to FIG. 5, which illustrates a schematic perspective top view of movement control units of an exemplary insertion device, according to some embodiments. As shown in FIG. 5, insertion device 100, includes several movement control units. A first movement control unit 110 is configured to allow advancement of the guidewire 108, which is inserted therethrough after having been re-inserted into the insertion device (as detailed above). A second movement control unit 120 is configured to allow advancing of a second medical tool (such as a catheter) after the guidewire 108 has re-entered the insertion device, while being threaded within the lumen of the second medical tool (catheter), via a second rear opening, towards the front face of the insertion device (via a corresponding front opening), as detailed above. A third, optional, movement control unit 102 is configured to allow controlling the rotation of the holder 104, in instances in which a holder 104 is used for holding the proximal end of the 30 guidewire 108, depending on the type of guidewire being used, so as to prevent twisting/kinking/tangling of the guidewire 108 while the guidewire is being rotated.

As shown in FIG. 5, the first movement control unit 110 may include a channel/shaft 113, through which the guidewire 108 is passed, and a movement element 114. Further shown are a motor 111) and one or more gears (representative gear 112 is shown), which allow controlling the operation of the movement control unit 110. The movement element 114 may include a rotating disc/ring/wheel 115, which is positioned so as to be in contact with the guidewire 108, whereupon spinning/rotation thereof, the guidewire 108 may linearly advance along its route. The guidewire 108 may be pushed toward the rotating disc/ring/wheel 115 by means of a spring/screw preloaded pinion. In some embodiments, the guidewire is pushed to the rotating disc/ring/wheel 115 by means of a pair of spring/screw preloaded pinions.

As shown in FIG. 5, facing the wheel 115 may be a groove, which forms a bent in the guidewire 108. The built-in bent in the guidewire's path increases the perpendicular distance of the line of action of force from the axis of rotation, which would be equal to the radius of the guidewire if the guidewire were to follow a linear path, thus enabling to exert a sufficient rotating moment (torque) on the thin guidewire, without having to apply a high normal force on the guidewire.

As further shown in FIG. 5, the channel/shaft 113 may have an opening/slit 116 along its length, to allow access to the guidewire 108 and further to allow placement/removal of the guidewire 108, if need be. In some embodiments, the first movement control unit 110 may rotate about an axis (for example, by the control of actuators 118), thereby allowing the rotational movement of the guidewire 108 (and the holder 104). In instances where rotational movement is actuated, the opening 113 may accordingly face another direction.

As further shown in FIG. 5, the second movement control unit 120 includes at least a channel 123, through which the medical instrument(s) are passed, and a movement element 124. Movement element 124 may include a rotating disc/ring/wheel 125, which is in contact with the medical instrument (e.g., the catheter with the guidewire threaded therein) placed in the channel 123, whereupon rotation thereof, the medical instrument can advance along its route.

As shown in FIG. 5, the channel 123 may have an opening/slit 126 along its length, to allow access to the medical instrument and further allow placement/removal of the medical instrument, if need be. In some embodiments, the second movement control unit 120 may be configured to rotate about its axis, thereby allowing the rotational movement of the second medical instrument (e.g., the catheter).

As further shown in FIG. 5, the third, optional, movement control unit 102 may include at least one gear 130, allowing the rotation of the holder 104. In some embodiments, in which the guidewire 108 comprises a double concentric guidewire (i.e., an inner wire disposed within the lumen of an outer hollow wire), the device 100 may further include actuators/element to allow controlling of the relative movement between the inner and outer wires of the guidewire, so as to control parameters of the tip of the guidewire (for example, the stiffness and/or curvature of the guidewire), in some embodiments, the device may include a non-rotating nut 103 attached to an adjuster/slider of the holder 104, which is rigidly attached to the proximal end of the inner wire, and a lead screw 105 threaded within the nut 103, to allow the controlling of the movement of the inner wire relative to the outer wire, thus controlling the tip parameters of the guidewire (such as, adjusting the stiffness and/or curvature thereof). Rotation of the lead screw 105 causes linear movement of the nut 103 along the length of the lead screw 105, which in turn causes linear movement of the adjuster/slider and the inner wire attached thereto.

In some embodiments, one or more of the following relative states between the inner and outer wires of the guidewire may be enabled by the above movement mechanism: 1) the distal tip of the inner wire extending distally beyond the distal tip of the outer wire, 2) the distal tip of the inner wire being translated proximally so as to be disposed within the outer wire (i.e., the distal tip of the outer wire extending beyond the 20 distal tip of the inner wire), and/or 3) the distal tips of the inner and outer wires being aligned.

Figure 6A:
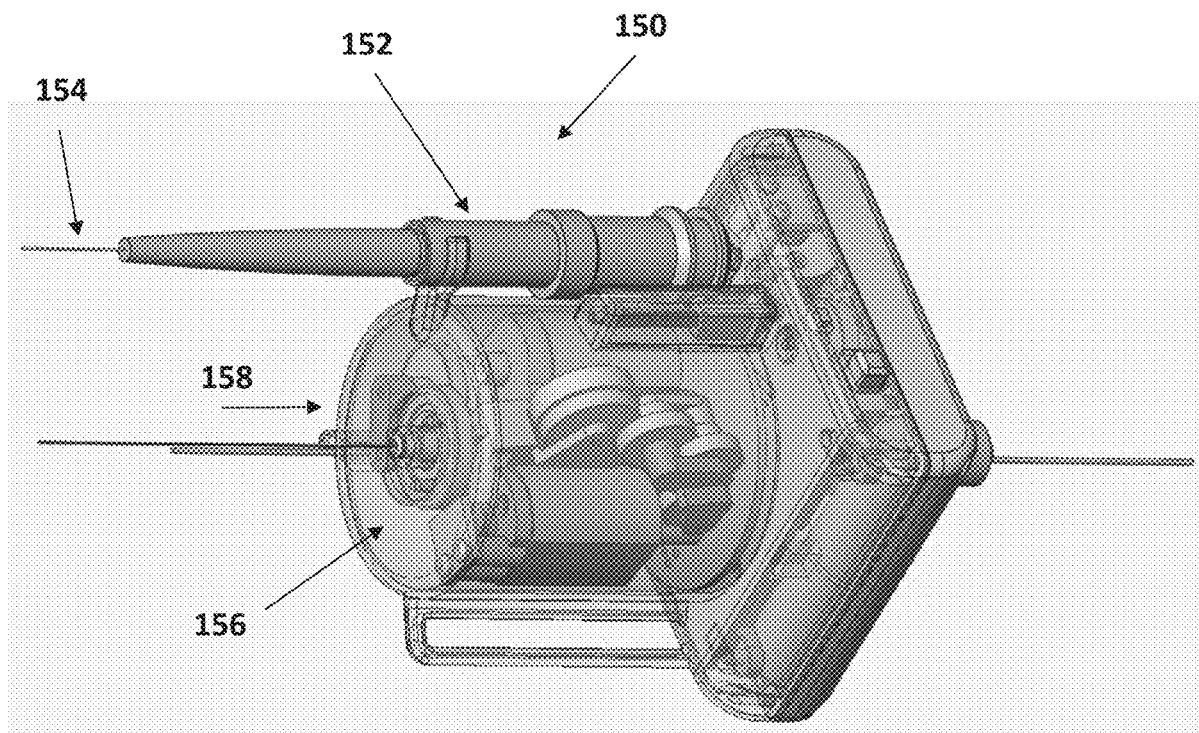
FIG. 6A illustrates a schematic perspective view of an insertion device, according to some embodiments.

Reference is now made to FIG. 6A, which illustrates a schematic perspective view of an exemplary insertion device, according to some embodiments. As shown in FIG. 6A, the insertion device 150 may include a housing (shown as semi-transparent housing 158) which encases movement control units 156 configured for advancing a medical instrument (such as a guidewire 154), in a linear direction and, optionally, in rotational movement. As illustrated in FIG. 6A, the proximal end of the guidewire 154 may be secured to a dedicated holder 152 that may further allow control over tip parameters of the guidewire 154. The guidewire 154 can advance from the holder 152 to enter the insertion device via an opening, and re-exit the device from a different opening at the opposite face of the device. In some embodiments, the guidewire 154 may exit the insertion device 150 into the lumen of another medical instrument (such as a catheter), which can be connected/attached/associated with an opening of the device.

Figure 6B:
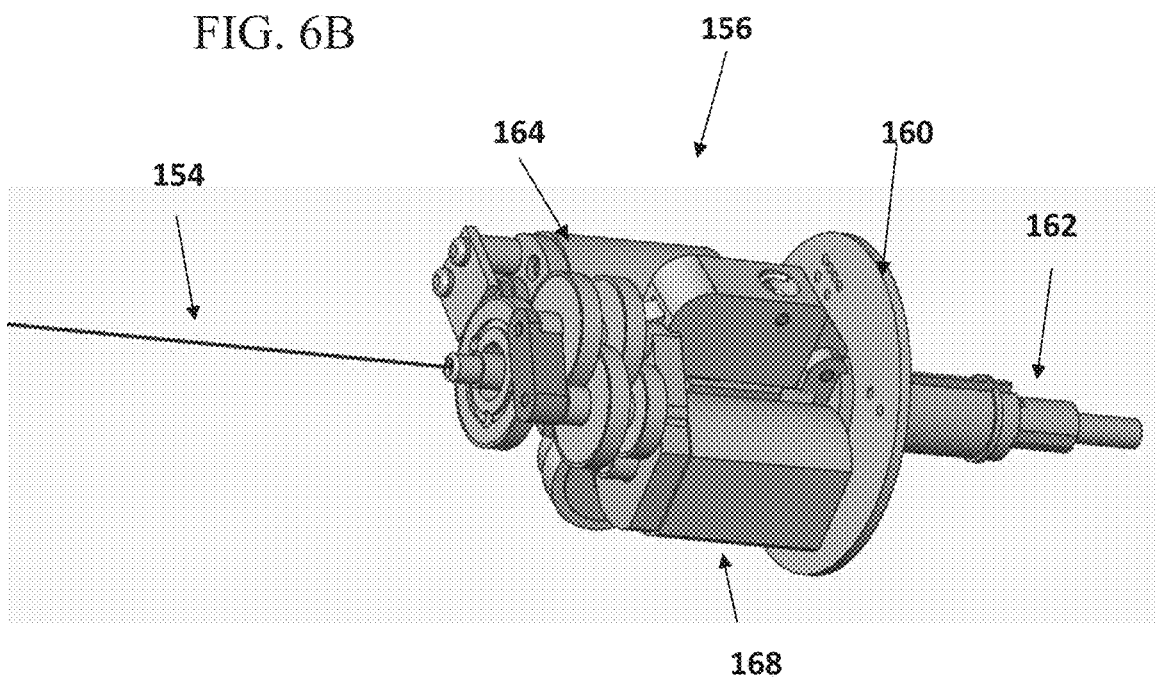
FIG. 6B shows a perspective view of a movement control unit, according to some embodiments.
Figure 6C:
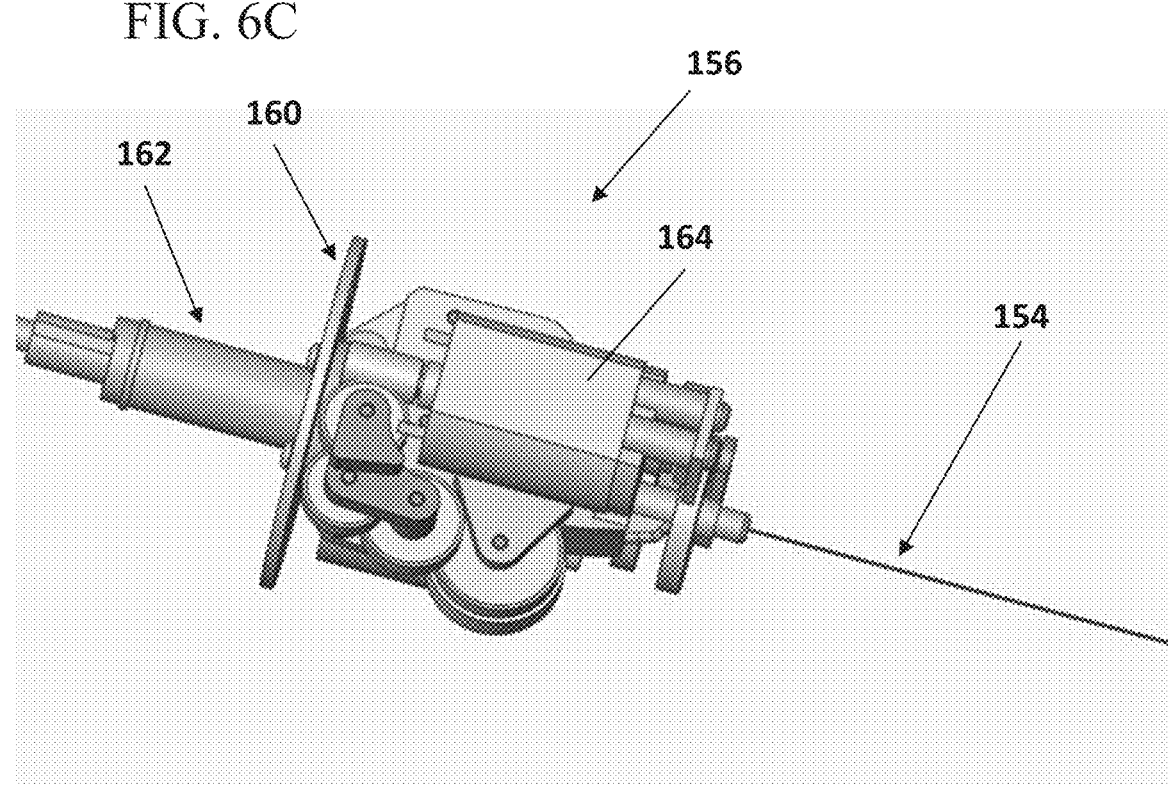
FIG. 6C shows a side view of a movement control element, according to some embodiments.

Reference is now made to FIG. 6B, which shows a perspective view of the movement control unit 156. As shown in FIG. 6B, the movement control unit 156 may include a shaft/channel 162, through which the medical tool (such as guidewire 154) can pass/advance. Movement control unit 156 further includes a medical instrument linear drive (168) and optionally a rotational drive (164). The movement control unit 156 may further include a slip ring 160 configured to allow rotational movement. The movement control unit 156 may further include one or more rotating/spinning elements (such as wheels and gears), configured to mediate mechanical movement of various moving parts, as detailed below. Reference is now made to FIG. 6C, which shows a side view of the movement control unit 156. Shown in FIG. 6C is shaft 162, guide wire 154, rotational drive 164, as well as slip ring 160.

Figure 7:
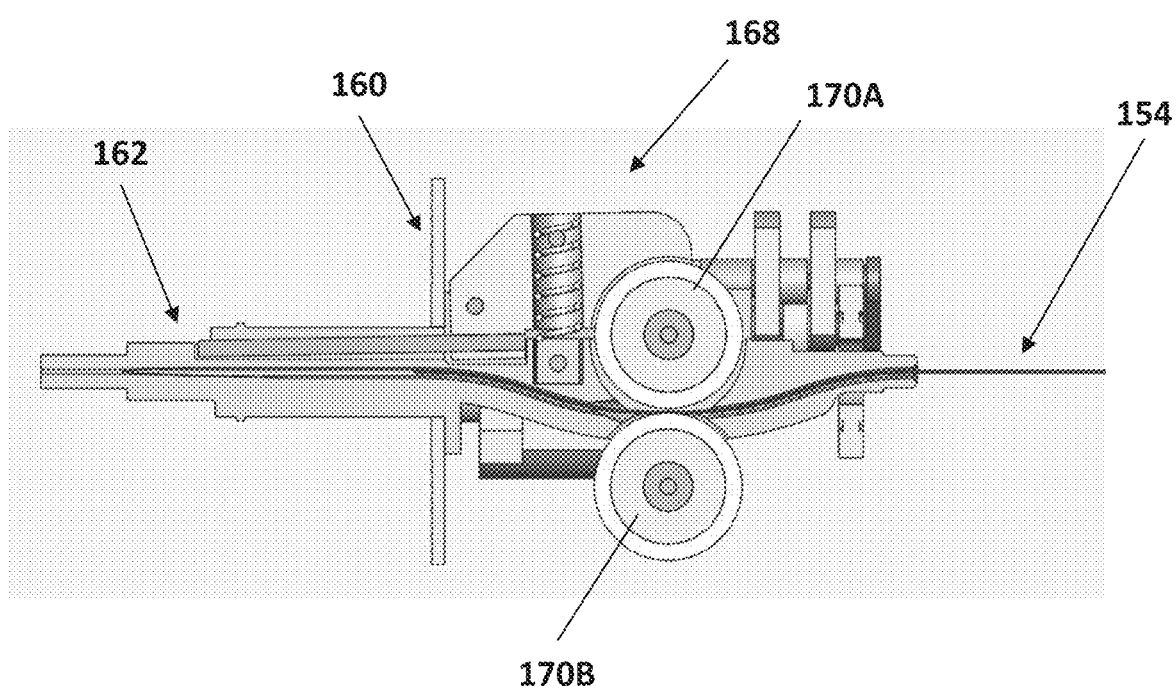
FIG. 7 shows a longitudinal cross section view of a movement control element of FIG. 6C.

Reference is now made to FIG. 7, which shows a longitudinal cross section view of the linear drive 168 of the movement control unit shown in FIG. 6C, essentially along the center of shaft 162.

As shown in FIG. 7, the linear drive 168 may include at least two rings/wheels/discs (170A, 170B), placed/situated/located one above the other and having a limited space therebetween. The medical instrument (such as guide wire 154) is configured to pass via the tight space between wheels 170A and 170B, such that upon spinning/rotation of the wheels, the guidewire, which is at least partially in contact with both wheels, advances linearly.

In some embodiments, the wheels/rings/discs 170A and 170B may be identical in size, shape, composition, or form. In some embodiments, the wheels/rings/discs 170A and 170B may be different in size, shape, composition, stiffness, material or form. In some embodiments, the space between the wheels 170A and 170B is formed in a groove, such that the medical instrument 154 is slightly bent, to allow better rotation of the medical instrument. A potential advantage of a built-in bent in the guidewire's path may include increasing the perpendicular distance of the line of action of force from the axis of rotation (which would be equal to the radius of the guidewire if the guidewire were to follow a linear path), thus enabling to exert a sufficient rotating moment (torque) on the thin guidewire, without having to apply a high normal force on the guidewire.

Reference is now made to FIG. 8, which schematically illustrates a movement control unit, according to some embodiments. As shown in FIG. 8, movement control unit is configured to allow linear advancement and/or rotational movement of a medical instrument (such as a guidewire 202). In some embodiments, the medical instrument 202 can advance along a path, for example, as defined by a channel or shaft (shown as channel 204). In order to allow linear movement of the medical instrument 202, the movement control unit may comprise a linear drive element 200, which may include two or more spinning/rotating elements, shown in FIG. 8 as wheels/discs/rings 206A and 206B.

As shown in FIG. 8, the wheels may be placed side by side, forming a tight space therebetween. The medical instrument 202 me be threaded between the wheels, such that it may pass below a first wheel 206A and above a second wheel 206B, so as to form an S shape, or substantially an S shape. By this manner, since the medical instrument 202 is at least partially in contact with the wheels, spinning/rotation of the wheels in opposite directions causes the instrument 202 to linearly advance. The relative spinning direction of the wheels 206A and 206B can determine the direction of the linear movement of the medical instrument 202.

In some embodiments, the movement control unit may further include a rotational drive element 210, which can allow rotation (for example, in direction 212) of the linear drive element 200 and hence of the medical instrument 202 intertwined therein. By utilizing the intertwining of the medical instrument around the wheels in an S shaped path as detailed above, the medical instrument can rotate freely around its axis, without slippage and without forming bents along its length. In some embodiments, the movement control unit is located/placed on a platform (shown as platform 214), to allow free rotation of the unit.

Reference is now made to FIGS. 9A-9B, which illustrate moving units for linear advancement and/or rotational movement of the medical instrument, according to some embodiments. In some embodiments, as shown in FIG. 9A-9B, linear and/or rotational movement of the guidewire may be generated by means of piezoelectric actuators. Piezoelectric elements are composed of ceramic material which changes its geometric dimensions as a function of the applied voltage. Piezoelectric elements enable activation at high frequencies, e.g., 50-150 kHz, and they can produce relatively large forces, which are linearly correlated to the degree of lengthening of the element (stroke). Using piezoelectric actuators in an automated medical device is advantageous as their activation does not generate a magnetic field, which is undesirable in medical applications. Further, piezoelectric actuators are MRI compatible. In some embodiments, other actuator types may be used, for example, electromagnetic actuators (solenoid), DC motors, stepper motors or AC motors.

According to some embodiments, the insertion device may include two separate portions/units; a first portion for generating linear movement (also referred to hereinafter as "linear portion") and a second portion for generating rotational movement (also referred to hereinafter as "rotational portion"), to allow each movement type, i.e., linear and rotational, to be generated independently of the other. A combined movement, i.e., simultaneous rotation and linear advancement, may be generated by activating the two portions in an ordered or alternate manner.

In some embodiments, the linear portion may be in the form of an inchworm motor, and it may comprise three piezoelectric actuators, as shown in FIG. 9A. Piezo actuators 301 and 303 are used to grip the medical instrument 304 (e.g., a guidewire), by extending (lengthening) and relaxing (shortening) along the vertical axis when powered, and motion is achieved by piezo actuator 302 lengthening and shortening along the horizontal axis when powered. In some embodiments, piezo actuator 301 and/or 303, may include a single actuator which presses the guidewire 304 against a static element, when extending, to grip the guidewire 304. In other embodiments, piczo actuators 301 and/or 303 are de facto a pair of piezo actuators, positioned on opposite sides of the guidewire 304, such that both extend and relax to grip and release, respectively, the guidewire 304. The actuation process of the linear portion is a cyclic process. In order to move the instrument 304 from left to right, for example, piezo actuator 303, which is the forward clutch piezo in this example, is first extended so as to grip the instrument, as shown in FIG. 9A. Next, piezo actuator 302, the lateral piezo, is extended, resulting in piezo actuator 1003, together with the instrument, moving a small distance to the right. It should be noted that the center of piezo actuator 302 is fixated, such that when power is supplied to piezo actuator 302, its extension is symmetrical to both sides, left and right. Since at this stage of the process piezo actuator 301, which is the aft clutch piezo in this example, is in a relaxed state, and does not grip the instrument, the instrument, which is gripped by piezo actuator 303, moves to the right. Next, piezo actuator 301 is extended so as to grip the instrument, followed by the relaxation of piezo actuator 303, so as to release its grip of the instrument. Next, piezo actuator 302 is relaxed. Next, piezo actuator 303 is extended to re-grip the instrument, followed by the relaxation of piezo actuator 301.

As shown in FIG. 9B, the rotational portion/moving unit of the device may include a pair of piezo actuators 306, 307, which contact the instrument 308 on opposite sides, parallel to one another. Extending the two piezo actuators in opposite directions 309A and 309B causes the instrument to rotate. In some embodiments, at least one of the clutch piezo actuators/pairs, i.e., piezo actuator 301 and/or piezo actuator 303, may be part of the rotational portion of the device, as well as of the linear portion of the device, as described above. In other embodiments, an additional pair of piezo actuators may be used for rotating the guidewire.

Reference is now made to FIG. 10, depicting a schematic illustration of an exemplary device capable of imparting both linear and rotational motion on a medical tool, according to some embodiments. In some embodiments, the linear motion may be achieved in an inchworm manner using piezo motors 401, 402 and 403, essentially as described above with respect of FIGS. 9A-9B, but with additional piezo motors 404 and 405 serving as clutches which are moved toward and away from the medical tool (shown as guidewire 408) by piezo motor 403. In order to rotate the guidewire clockwise ("CW"), for example, piezo motor 403 is relaxed/contracted, such that it moves piezo motors 404 and 405 toward the guidewire 408, until they grip the guidewire, at opposite sides. Piezo motor 405 is then extended (moved downward), while piezo motor 404 is simultaneously relaxed/contracted (moved upward), causing the guidewire to rotate. Piezo motor 401 is then extended, so as to grip the guidewire, and piezo motor 403 is extended, so as to release the grip of the guidewire by moving piezo motors 404 and 405 away from the guidewire, to their original position. In alternative embodiments, an additional piezo motor may be coupled to one of piezo motors 404 and 405, instead of piezo motor 403, to move it toward and away from the guidewire. In such embodiments, rotation of the guidewire may be achieved by both piezo motors 404 and 405 extending (or contracting), in opposite directions. The utilized piezo actuator/s may be, for example, the PICMA® Monolithic Multilayer PZT Actuator, manufactured by PI Ceramic GmbH, Germany. In some embodiments, the rotating piezo actuators can rotate the entire linear advancement assembly.

Reference is now made to FIG. 11, which illustrates a movement control unit having two concentric circular components, which can rotate one relative to the other, according to some embodiments. As shown in FIG. 11, movement control unit 500 includes a first movement control element 502 (such as a piezoelectric motor) configured to allow linear motion (advancement) of a medical instrument (such as guidewire 510), in any linear desired direction 505. The first movement control element 502 is fixed to the inner concentric circular component 530 (see also FIG. 12). Movement control unit 500 further includes a second movement control element 504 configured to allow rotational motion of the first movement control element 502 by rotating the inner concentric circular component, in any desired clockwise or counter-clockwise direction 507.

Further shown in FIG. 11 is an optional setting, in which the proximal end of the medical instrument is secured to a dedicated holder 520. In some embodiments, for example when the guidewire comprises a double concentric guidewire (i.e., an inner wire disposed within the lumen of an outer hollow wire), the holder may include a mechanism which allows controlling parameters of the medical instrument, such as tip stiffness, which includes at least an adjuster/slider 503 configured to linearly move the inner wire relative to the outer wire. Further, an additional movement control unit 506 may be present, which allows control over the rotation of the holder 520 with the instrument attached thereto.

Reference is now made to FIG. 12, which illustrates an assembly of movement control units, for controlling movement of more than one medical instrument, according to some embodiments. As shown in FIG. 12, movement control assembly 600, includes two separate moving control units 602 and 604 that may be utilized in conjugation, such that each unit is configured to allow actuating and controlling movement of a different medical instrument.

As shown in FIG. 12, a first movement control unit 602 includes various moving elements, allowing linear motion (advancement) and/or rotational motion of a first medical instrument (such as guidewire 610), essentially as detailed above with respect of FIG. 11. A second movement control unit 604, includes various moving elements, allowing linear motion (advancement) and/or rotational motion of second medical instrument (such as microcatheter 612). In some embodiments, the movement (linear and/or rotational) of the first medical instrument 610 may be independent of the movement (linear and/or rotational) of the second medical instrument 612.

In some embodiments, the movement (linear and/or rotational) of the first and second medical instrument may be synchronized. In some exemplary embodiments, as illustrated in FIG. 12, the first medical instrument (for example, a guidewire) may pass and advance through the lumen of the second medical instrument (for example, a catheter). According to some embodiments, any suitable actuator type may be used in any of the movement control units, devices and systems disclosed herein, including, but not limited to: motors (such as, DC motors, AC motors, stepper motors, and the like), electromagnetic actuators (solenoid), piezoelectric actuators, pneumatic actuators, hydraulic actuators, and the like.

FIG. 13 is a block diagram of a surgical robotic system, according to some embodiments.

In some embodiments, a robotic system 1301 is suitable for use in a surgical room. Optionally, one or more system components (such as controlling components, imaging components) are physically separate from the rest of the system and may be used remotely.

In some embodiments, system 1301 is configured to receive one or more surgical tools (e.g. a guidewire, a microcatheter, a guiding catheter, an intermediate catheter, and/or other elongate surgical tool) and to actuate movement of the tools.

In some embodiments, the system is configured to drive linear movement (e.g. advancement and/or retraction) of a tool received therein, and/or drive rotational movement (e.g. axial rotation) of a tool received therein. In some embodiments, linear and rotational movements are actuated simultaneously.

In some embodiments, system 1301 includes a robotic device 1303 for driving movement of one or more tools. In some embodiments, the device housing accommodates and/or is operably connected to one or more of the following components:

one or more actuators such as one or more motors 1305, and optionally associated transmission of the motors.

Tool moving elements 1317, such as wheels, configured to operably contact a tool received by the system to move the tool (e.g. advance, retract, rotate the tool). In some embodiments, the tool moving elements are driven directly (e.g. by contacting) or indirectly (e.g. via one or more gears or other transmission) by the motors 1305. Optionally, only some tool moving elements are driven (directly or indirectly) by motors, while other tool moving elements move in response to movement of the tool and/or in response movement of a motor-driven tool moving element.

a controller 1307, configured to receive and/or send operation signals to and/or from a general control unit 1309. General control unit 1309 may be configured as a remote control device, a console, a control unit physically attached to the system base, or a combination thereof. In some embodiments, the controller 1307 is configured to coordinate manipulation (e.g. linear movement, rotation) of tools received and operated by the robotic system.

powering means 1311, including for example a battery and/or connection means for mains electricity.

sensing means 1315, for example, one or more sensors configured for detecting, for example, whether a tool has been inserted; a relative position of the tool; a position of tool-moving elements (e.g. wheels); actual movement of the tool-moving elements (e.g. by a counter counting the number of wheel rotations); sensors for communicating with other system sensors, and/or for other measurements and/or indications. In some embodiments, sensors are configured for detecting motor status, for example, a motor position, a motor rotation rate. Sensors of various types may be used, such as optical sensors, pressure sensors, force measurement sensors, speed sensors, sensor for detecting electrical current, flow sensors, position sensors (e.g. optical, magnetic, electrical position sensors).

a memory 1313, which stores, for example, parameters related to tool movement, such as speed of movement, rotation, translation, angulation, deflection angle; indications obtained by one or more system sensors, such as a measure of force acting on the tool, stiffness of the tool; parameters related to the patient body and sensed by the inserted tools (e.g. heart rate, blood pressure, temperature, oxygenation level, and/or other sensed parameters).

In some embodiments, the robotic device (also referred to herein as an insertion device) is compact and is small enough in dimensions so as to reduce interference to surgical room personnel (e.g. nurse, surgeon) and/or to surgical room equipment and/or to the patient. In some embodiments, the device footprint is smaller than 500 cm^2, 250 cm^2, 180 cm^2 or intermediate, larger or smaller area. In some embodiments, a volume of the device is less than 3500 cm^3, 2800 cm^3, 2000 cm^3 or intermediate, larger or smaller volume. In some embodiments, a weight of the device is less than 1.5 kg, less than 1 Kg, less than 800 grams, less than 500 grams or intermediate, higher or lower weight.

In some embodiments, the robotic device is substantially block shaped, for example having a box shaped compact configuration. Other configurations may include a cylindrical configuration, a rounded (e.g. ball shaped) configuration, a saddle shape, and/or other.

In some embodiments, system 1301 includes an integrated imaging modality 319. Alternatively, the system is configured to be operably attached to (for example, communicate with) an existing imaging modality. An imaging modality may include, for example, X-ray fluoroscopy, CT, cone beam CT, CT fluoroscopy, MRI, ultrasound, or any other suitable imaging modality.

In some embodiments, system 1301 comprises a mounting 1321 for placing device 303 relative to the patient and/or relative to the surgical bed. In some embodiments, the mounting comprises or is configured to attach to an adjustable fixture. Optionally, a height and/or angle and/or distance of the system relative to the patient (e.g. relative to the location of body entry) and/or relative to the bed are adjustable.

In some embodiments, system 1301 comprises or is configured to engage an adaptor 1323 for operably engaging a tool's proximal portion, for example, a handle.

In some embodiments, the adaptor defines a mechanical engagement between the one or more motors 1305 and one or more components of the handle which move the tool. For example, the adaptor connects one or more motor(s) or associated transmission with a slider component of the handle which deflects the tool tip upon sliding; with a knob component of the handle which rolls the tool when rotated; and/or with other handle components. Additionally or alternatively, the adaptor itself includes one or more integrated motors for driving movement of the handle components.

FIG. 14 is a flowchart of a general method of using a surgical robotic device, according to some embodiments.

In some embodiments, a decision is made, for example by a physician, surgeon and/or other clinical personnel, to operate (1401). In some embodiments, the operation is for therapeutic purposes. Additionally or alternatively, the operation is for diagnostic purposes.

In some embodiments, the operation involves catheterization. In some embodiments, the operation involves insertion of one or more tools into and/or through vasculature and/or into other non-vascular endoluminal structures. Examples of tools may include: a guide wire, a microcatheter, a rapid exchange catheter, a guiding catheter, a balloon catheter, a stent or coil, ablation tools, an intermediate catheter, a suction catheter, an ultrasound catheter, a pressure catheter and/or other tools. In some embodiments, the operation is a through-lumen based procedure. In some embodiments, the operation is an over-the-wire based procedure.

In some embodiments, the device is positioned relative to the patient (1403). In some embodiments, the device is mounted onto the surgical bed, for example via a fixation. In some embodiments, the device is attached to the patient, for example mounted onto the patient's leg (e.g. to the thigh), to the patient's arm, and/or to other body parts. Attachment of the device to the surgical bed and/or to the patient may be carried out using straps, bands, a rigid mounting, and/or other attachment means.

In some embodiments, attachment to the bed is carried out using a stand which is stabilized relative to mattress and/or to the rail of the bed and/or to the floor. The system can then be mounted on the stand, for example attached via a snap fit mechanism, magnetic means, straps (e.g. Velcro), and/or other. In some embodiments, the stand is adjustable so as to enable use with patients of various sizes and/or different bed height and the like. In some embodiments, when setting a position of the device, one or more of a height, entry angle to the body, alignment of the device relative to the patient are selected. The device position may be defined with respect to the patient body or parts thereof (e.g. relative to the surgical entry point) and/or relative to the surgical bed and/or relative to other surgical room equipment, e.g. relative to imaging modules.

A potential advantage of attaching the device to the patient's body, for example to a limb and/or other body portion (e.g. leg, arm (optionally the snuffbox of the hand), neck, foot, etc.) may include that the device can be positioned closer to the entry opening into the body. In such configuration, a length of a tool segment extending between the device and the body may be reduced, potentially allowing for more efficient use of a tool's length. In some embodiments, the device is compact enough so as to fit on top of a patient's limb, for example, without protruding laterally from the limb when the device is attached onto the limb (for example, the device is sized not to extend laterally from a patient's thigh).

In some embodiments, loading of the tools is performed (1405). In some embodiments, loading of tools is performed after the device position (e.g. relative to the patient and/or to the bed) is set; alternatively, loading of tools is performed before the device position is set. Optionally, one or more tools are preloaded onto the device, and are optionally provided along with the device. In an example, the device is provided in a sterilized package while already being loaded with one or more tools. Additionally or alternatively, tools are unwrapped in the surgical room and are loaded onto the device, for example by a nurse, technician and/or other clinical personnel. In some embodiments, tools are loaded and/or replaced during operation, for example when switching from a navigational tool (e.g. a guidewire) to a treating tool, such as an embolization tool, a catheter balloon, and/or other treating tool.

In some embodiments, the device is constructed so that no shielding (e.g. no physical separation by a wall, a wrap, a drape) exists or is required between the tool-moving element and the tool being loaded, for example, such that direct contact is formed between the tool and the tool-moving elements (e.g. wheels, gears, and/or other actuators). Optionally, no draping by a sterile drape or other cover is required. For example, in a single-use device that is disposed following surgery, due to having no permanent components, there is no need to cover the device and/or specific components of it which contact the tools by a sterile drape. A potential advantage of a device in which the device is configured to engage the surgical tools directly, without a separation or cover may include a simpler, more efficient, time and/or cost effective preparation process and/or cleaning process following surgery.

Alternatively, in some embodiments, the device (and/or selected components of the device, such as the tool moving elements) are at least partially covered by a sterile drape or sheath.

In some embodiments, operation is performed by controlling, via a user interface of the device, movement of the surgical tools received within the units (1407). Exemplary manipulation of tools controlled by the device may include: linear advancement and/or retraction of a tool; rotation of a tool (e.g. roll about the tool axis); twisting of a tool; angular orientation of a tool (e.g. by curving a distal tip of a tool); articulation (e.g. of a distal tip of a tool); changing of mechanical properties of a tool, such as stiffness, for example by controlling, from a proximal end of the tool, a distal tip structure or inner arrangement.

In some embodiments, manipulation of tools is performed remotely. Optionally, the surgeon operates the system from a different room. Alternatively, the surgeon stays in the surgical room, and may operate the system while being adjacent or far from the bed.

In some embodiments, manipulation of tools involves maneuvering of tools that are attached to each other and/or inserted into one another and/or otherwise assembled in a manner in which movement of one tool may affect the other, for example, when a guidewire extends within a lumen of a microcatheter. In such situation, controlling movement may involve carrying out (via user control and/or automatically by the system, upon identification of movement) "compensation" movements of the guidewire and/or microcatheter with respect to each other, which may be required when both are driven together in an assembled configuration (such as when the guidewire is within the microcatheter lumen in the position of the tool moving elements of the unit, where the tool is manipulated). In an example, when the microcatheter is advanced or retracted, it may be desired to hold the guidewire in place without having the guidewire move along with the microcatheter. This may be carried out, for example, by driving the linear movement mechanisms of both tools, but in opposite directions (e.g. advancing the microcatheter distally while at the same time driving the guidewire mechanism in a manner that would retract the guidewire proximally). A potential advantage of synchronized controlled movement of tools that are used together (such as a guidewire extending within a lumen of a microcatheter) may include the ability to hold one tool while advancing the other tool, for example by driving the actuation mechanisms of the tools in opposite directions—one tool would be advanced or retracted while the other tool would effectively remain in place.

In some embodiments, the user interface is configured on the device itself (e.g. as a screen and/or buttons and/or a joystick attached to the system units and/or to the base), and/or on a separate physician console, and/or on a separate remote control device. Control signals may be communicated via wired and/or wireless communication (e.g. network based communication) to the device.

In some embodiments, the device (e.g. the device controller) is programmed to include a loading mode, for insertion and/or calibration of tools and/or of the device motors; and an operational mode, where movement of the tools is carried out.

In some embodiments, the device or specific components of it are disposed following operation (1409). Optionally, the device is disposed as a whole, optionally including the tools loaded on it.

FIG. 15 is a flowchart of a method of loading a plurality of surgical tools onto the surgical robotic device, according to some embodiments.

In some embodiments, a robotic device for example as described herein is provided (1501). In some embodiments, one or more elongate surgical tools such as a guidewire, a microcatheter, a guiding catheter, a rapid exchange catheter and/or other surgical tools are provided (1503).

In some embodiments, a proximal handle of a tool such as a guidewire is placed in engagement with a designated adaptor or holder (1505), for example as described in co-filed PCT titled "ROBOTIC MANIPULATION OF A SURGICAL TOOL HANDLE" (PCT Patent Application No. PCT/IL2020/051225) which is incorporated herein by reference.

In some embodiments, the guidewire is threaded (such as from the distal end direction) into a designated shaft of the guidewire driving mechanism of the robotic device (1507). Then, at least a portion of the guidewire length which exits the shaft (existing the device housing) is threaded into a lumen of a microcatheter (1509).

In some embodiments, a proximal end of the microcatheter (which has not yet been physically attached to the device) is secured to the device at an exit port of the guidewire from the housing (1511). Then, at least a portion of the microcatheter length (including the guidewire received inside) is threaded into a designated shaft of the microcatheter driving mechanism of the device (1513). The microcatheter is then passed (along with the guidewire received inside) through a lumen of a guiding catheter (1515).

Optionally, the guiding catheter is received or engaged by a guiding catheter driving mechanism, which may be externally operably coupled to the device housing or, alternatively, integrated inside the device.

Then, in some embodiments, the one or more tools are introduced into the patient's body (1517) and are manipulated using the device.

In an exemplary use, the robotic device is loaded with a guidewire and optionally a microcatheter. Optionally, a guiding catheter (a distal portion thereof) is manually inserted into the patient's body. Then, the robotic device is placed adjacent a proximal end of the guiding catheter, and the guiding catheter (optionally along with a microcatheter in which the guidewire is received) is inserted into the lumen of the guiding catheter. In some embodiments, insertion into the guiding catheter lumen is performed via a seal element, which may be an integrated part of the robotic device or, alternatively, separate from it. Then, in some embodiments, the user connects the proximal end of the guiding catheter to the robotic device. From this point on, manipulation (e.g. linear advancement/retraction, and/or rotation) of the guidewire and/or of the microcatheter inside the lumen of the guiding catheter and optionally upon the guidewire and/or microcatheter exiting the guiding catheter (such as into a lumen of a vessel) may be carried out robotically using the device (for example, through a remote control interface). In some embodiments, linear advancement and/or retraction of the guiding catheter, for example to a certain limited extent, is also carried out using the robotic device.

FIGS. 16A-D are various configurations of a remote control device of the surgical robotic system, according to some embodiments.

In some embodiments, the remote control device is shaped to be manually held by a user, e.g. a physician. Optionally, the remote control device is lightweight and small enough to be held by the user without blocking the user's view of visual aids such as a screen showing the results of imaging during operation. In some embodiments, the remote control device includes one or more portions shaped to be gripped by the user palm and/or engaged by the user's fingers.

In some embodiments, the remote control device communicates with the modular robotic system. In some embodiments, the communication is wireless, performed for example via wi-fi, infrared, Bluetooth, RF, and/or other wireless modules.

In some embodiments, the remote control device includes or is in communication with a controller of the modular robotic system. In some embodiments, maneuvering of tools received by the system is performed via the remote control device. Examples of tool movements and/or other operational manipulations of the tools which are controlled by the remote control device may include: linear advancement and/or retraction of a tool; axial rotation of a tool; control of a tool distal tip; speed of movement; control of unique tool functions (e.g. inflation/deflation of a balloon in a balloon catheter, stent deployment and/or advancement), and/or other tool manipulation.

Other functions which may be controlled via the remote control device include, for example: automated injection of materials (e.g. contrast agents, washing solutions) into and through a tool lumen; linear and/or angular movement of the assembled system as a whole (e.g. sliding of the assembled system relative to a mounting); safety stop of the system; on/off actuation of the system; supply of electrical power to the system or to specific components; and/or other system functions.

Figure 16A:
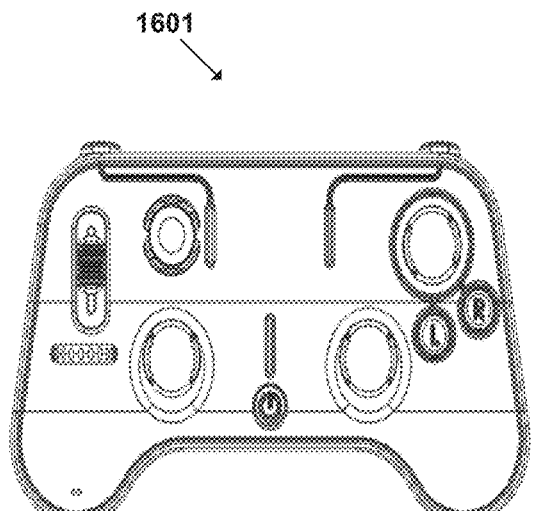
Figure 16B:
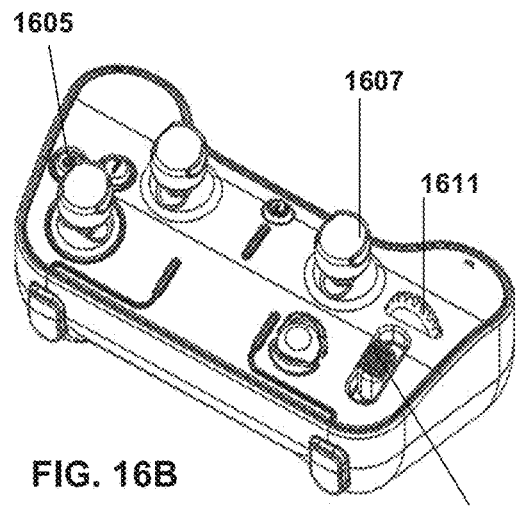
Figure 16C:
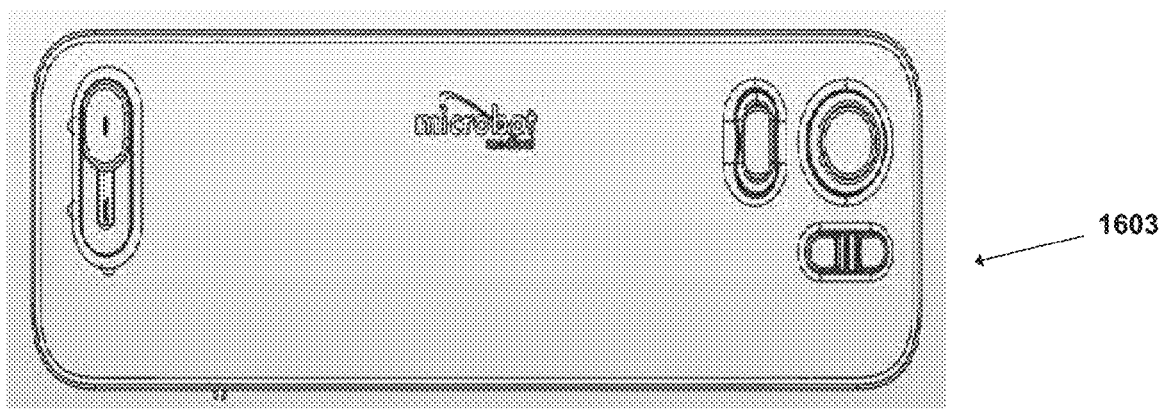
Figure 16D:
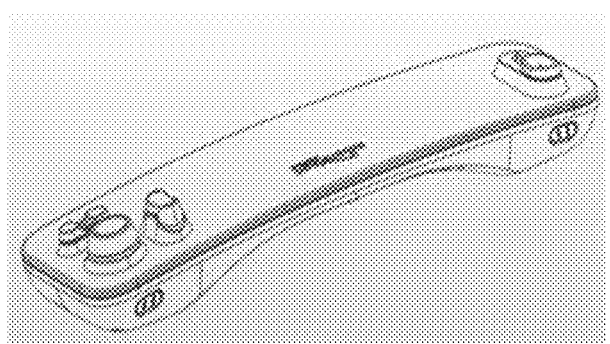

FIGS. 16A-B show a first example of a remote control device 1601, and FIGS. 16C-D show a second example of a remote control device 1603. In some embodiments, the device includes interfaces in the form of one or more of: push buttons 1605, joystick handles 1607, manual sliders 1609, rotating knobs, 1611 and the like.

In some embodiments, the remote control device comprises a screen, such as for notifying a user regarding current controls and/or for receiving commands from the user.

In some embodiments, the remote control device includes an interface (e.g. a button) for rapid retraction of tools. Such interface may be used in case of an emergency, device failure, or the like and/or for planned retraction of a tool, such as for replacing the tool with a new tool.

In some embodiments, the remote control device is modular. Optionally, specific buttons and/or add-on interfaces are selectively attached (and/or are uncovered to enable their use). For example, buttons for controlling movement of a guiding catheter (when a guiding catheter receiving unit has been attached on the system) are exposed for use only when required (e.g. are positioned under a removable or movable cover). In another example, an interface for controlling injection of materials through one or more system junctions is attached to the remote control device and/or uncovered for use upon need.

The remote control device may be operated at a distance from the system. Optionally, the remote control device is operated by a surgeon located in a different room. Optionally, the remote control device is operated by a surgeon located in the surgery room (adjacent the bed or at a distance from the bed).

In some embodiments, the remote control may be configured as a screen interface, for example for use in a cell phone, tablet, computer or the like, such as described below.

FIG. 17 is a schematic example of a screen interface associated with the surgical robotic system, according to some embodiments.

In some embodiments, additionally or alternatively to a remote control device for example as described hereinabove, a screen interface 1701 in communication with the system may be used. In some embodiments, the screen interface is configured for receiving data (such as from the device and/or from imaging means and/or from the physician and/or from a hospital system), presenting data, sending and/or receiving commands to and from the robotic device, and/or other.

In some embodiments, the screen interface may be configured in a computer, a laptop, a tablet, as a cell phone application and/or other.

The user interface screen shown in this figure presents examples of functions and/or indications related to operation of the tools by the robotic device, including, but not limited to: tool movement type (e.g. guidewire roll, guidewire advancement/retraction, microcatheter advancement/retraction, guiding catheter roll, guiding catheter advancement/retraction); guidewire tip control (e.g. guidewire tip deflection); tool speed and/or movement direction (e.g. increasing the speed using "turbo" mode, initiating fast or partially fast retraction); emergency stop (in case of device failure, medical emergency situation or the like; in some embodiments, the emergency stop button stops power supply to the robotic device); controlling movement of two (or more) tools together; customized control of tool movement, such as: control of accessories including devices and/or add-on accessories used with the system and/or tools, such as: injection of material through a port; inflation of a balloon; stent expansion; tip curvature, tool stiffness.

FIGS. 18A-B are different views of a robotic device, according to some embodiments.

In some embodiments, a robotic device 1801 is shaped and sized to be located adjacent the patient (e.g. attached to the bed) and/or located on the patient, for example on a patient's limb (e.g. on the patient's thigh). In the example shown, device 1801 comprises a compact housing 1802 having a saddle shaped bottom portion 1803. Optionally, the saddle shaped portion is shaped and sized to be seated on a patient's limb, on a rail of the bed, on a designated mounting (e.g. a mounting having a planar bottom for positioning on a planar surface, not shown), and/or other. In some embodiments, a second portion 1805 of the housing extends from the saddle bottom, the second portion accommodating the one or more tool driving mechanisms.

In some embodiments, a guidewire is loaded onto the device 1801 as follows: in some embodiments, a proximal portion (e.g. a handle) of the guidewire is received within an accessible compartment 1807, optionally covered by a lid 1809 (compartment 1807 may also be referred to herein as an "adaptor" or "holder"). Optionally, manipulation of one or more guidewire handle components is performed within compartment 1807 by one or more movers which engage the handle (e.g. engage a slide of the handle, a rotational knob of the handle, and/or other handle components).

In some embodiments, a more distal portion of the guidewire (adjacent the handle) exits compartment 1807 via aperture 1813. Then, in some embodiments, an even more distal portion of the guidewire (optionally, the distal most end of the guidewire) is then inserted through an entry aperture 1811 into the device housing, where the inserted guidewire is received within a designated shaft (not shown) of its driving mechanism. In some embodiments, the guidewire exits the housing again, optionally from an opposite wall of the housing, via aperture 1815. In some embodiments, a location of aperture 1815 also serves as a securing point for a proximal end of a microcatheter. Optionally, the microcatheter is threaded on a knob 1817 and/or other suitable protrusion to be secured to the housing. When the guidewire exits through aperture 1815, it is received within a lumen of the microcatheter.

In some embodiments, the microcatheter (along with the guidewire extending inside) is curved (e.g. to a "U" shape) outside the housing to be inserted, via an aperture 1819, into a designated shaft of the microcatheter driving mechanism. The microcatheter (along with the guidewire inside) then exits the housing on an opposite wall, via aperture 1820.

In some embodiments, the device housing is shaped and sized solely for accommodating the tool driving mechanisms, without being affected by tool size considerations, such as tool length, a tool width (e.g. diameter). Optionally, the housing protects the tool driving mechanism inside while only the tools themselves remain visible and/or contactable externally to the housing. Optionally, no driving mechanisms are visible. A potential advantage of such construction may include reducing a risk of damage (e.g. by unwanted contact) with the tool driving mechanisms.

In some embodiments, a portion of a tool that extends within the housing itself is less than 25%, less than 20%, less than 10%, less than 5% or intermediate, larger or smaller percentage of the total length of the tool. A potential advantage of a housing which accommodates the driving mechanisms and does not require a long portion of a tool to be received inside may include allowing for a relatively compact housing having small dimensions and/or small weight.

In some embodiments, the housing includes a removable or movable portion such as a lid. Optionally, the lid is opened in case of an emergency and/or robot malfunction, for example to manually release the tools. Alternatively, the lid is opened in case of a need to replace the tools.

In some embodiments, opening of the lid automatically returns the device motors to an initial (home) position and/or orientation. Optionally, the actuation mechanisms of the tools, for example a designated shaft in which a tool is received, are rotated to be aligned such that a slot extending along the shaft faces upwards, in the direction of the open lid. A potential advantage of the motors and/or tool shafts being automatically aligned upon opening of the lid of the device housing may include that tools can be more easily approached for adjustment and/or removal of a tool from its mechanism.

Exemplary dimensions of upper portion 1805 of the device (without the saddle shaped bottom, which could alternatively be formed as a planar surface) may include: an axial length 1821 of less than 12 cm, a width 1823 of less than 7 cm, a height 1825 of less than 9 cm.

In some embodiments, housing 1802 is formed of a relatively lightweight yet durable material, such as plastic, aluminum, composite materials. Optionally, the material is recyclable, so that a disposed device (e.g. a single use device) may be at least partially recycled.

FIGS. 19A-B schematically illustrates a surgical robotic device including or attached to a guiding catheter driving unit, according to some embodiments.

FIGS. 19A-B show robotic devices having different shaped housings. FIG. 19A shows a robotic device housing 1900 such as described above in FIGS. 18A-B, seated on a mounting 1921 which defines a planar surface. FIG. 19B shows a substantially box shaped housing 1902, having a square or rectangular cross section profile.

In some embodiments, a guiding catheter driving mechanism 1901 is configured as a separate add-on unit configured to operably couple to the robotic device, for example, to be appended to device housing 1903.

In some embodiments, the guiding catheter driving unit attaches to the housing in a manner in which a microcatheter existing the housing (such as via an aperture 1905) enters a lumen of a guiding catheter loaded onto the guiding catheter unit. In some embodiments, attachment of the guiding catheter unit to the housing is by one or more of: an interference fit coupling (e.g. via respective protrusions and indentations of the device housing and a housing of the guiding catheter driving unit), a sliding attachment (e.g. including a rail 1906, for example as shown in FIG. 19A).

In some embodiments, rail 1906 moveably couples the guiding catheter driving unit 1901 to one or more motors located inside the housing of the device, for example so that a motor drives back and forth movement of the unit for moving the guiding catheter. In some embodiments, the guiding catheter driving mechanism is configured to drive linear movement and/or rotational movement (i.e. roll) of the guiding catheter. In some embodiments, the guiding catheter driving unit is configured to electrically connect to the robotic device and receive power supply from it. Alternatively, the guiding catheter driving unit includes an independent power supply (e.g. a battery).

In some embodiments, the guiding catheter driving unit connects to the robotic device via mechanical connections, such as by a snap fit connection, an interference fit connection, pin and socket, and/or other suitable mechanical coupling.

Alternatively, in some embodiments, the guiding catheter driving mechanism is inside the robotic device housing, and forms an integral part of the robotic device.

In some embodiments, the guiding catheter driving mechanism is configured for driving linear movement of the guiding catheter within a selected distance range, for example, to advance and/or retract the catheter a distance of 3 cm, 5 cm, 10 cm, or intermediate, longer or shorter distance. In some embodiments, this provides for fine tuning of a position of a guiding catheter previously inserted into the patient.

In some embodiments, to ensure that a microcatheter within the guiding catheter moves along with the guiding catheter, the microcatheter driving mechanism is controlled for compensating for that movement, for example, the microcatheter is actuated to move in an opposite direction to the guiding catheter. Optionally, a guidewire within the microcatheter moves along with the microcatheter as a single unit and does not require independent actuation.

FIGS. 20A-C are an example of an isolated mechanism of the guiding catheter driving unit, an example of a guiding catheter driving unit housing, and a guiding catheter driving unit assembled onto the robotic surgical system, according to some embodiments.

In some embodiments, a guiding catheter mechanism (see FIG. 20A) includes one or more motors, such as a motor 2001 for driving linear movement, and a motor 2003 for driving rotation. In some embodiments, a proximal portion of the guiding catheter 2005 is attached at connector 2009. In some embodiments, in operation, motor 2001 rotates a lead screw 2007 which in turn advances or retracts connector 2009, thereby advancing or retracing the guiding catheter 2005. In some embodiments, motor 2003 moves linearly along with connector 2009. In some embodiments, activation of motor 2003 rotates connector 2009, thereby rotating (rolling) the guiding catheter 2005.

FIG. 20B is an external view of a guiding catheter unit 2000. In some embodiments, the unit comprises an elongate housing 2011, and the lead screw 2007 (such as shown in FIG. 20A) extends throughout the housing. In some embodiments, housing comprises one or more ports leading into the guiding catheter lumen. For example, an injection port 2010 through which materials (e.g. liquid agents, saline, etc.) can be injected into and through the lumen of the guiding catheter.

In some embodiments, housing 2011 is shaped for attaching to the robotic device. In an example, the housing defines an abutment 2012 which can lean against the external housing of the robotic device and/or at least partially connect to it, such as by being received within a respective recess or indentation defined at the robotic device housing.

FIG. 20C shows the guiding catheter unit 2000 connected to a robotic device 2013. In some embodiments, the guiding catheter unit is coupled to an external wall of the device housing 2015. Optionally, the guiding catheter unit extends distally in the direction of insertion into the patient.

As further shown in this example: a guidewire 2019 extends from a guidewire holder 2021 and into a designated shaft of the guidewire driving mechanism; the guidewire then exits the housing at 2025, which also serves as a securing point for the microcatheter 2027, and the guidewire enters the microcatheter lumen. Then, the microcatheter is bended to enter the device housing at 2029, being received within a designated shaft of the microcatheter driving mechanism. When the microcatheter (along with the guidewire received within) exits the housing, it is received within a lumen of the guiding catheter 2005 held and manipulated by the guiding catheter unit 2000.

FIGS. 21A-C show mechanisms for actuating rotation (roll) and/or linear movement of a tool actuated by the robotic surgical system, according to some embodiments.

In some embodiments, as shown in the exemplary mechanism of FIG. 21A, a guidewire 2101 inserted into a designated shaft is engaged by at least one pair of driving wheels 2103 positioned opposite each other and contacting the guidewire that passes between them. A motor 2105 for driving linear movement of the tool actuates rotation of the wheels which, depending on the rotation direction, cause the guidewire to move axially in a proximal or distal direction.

In some embodiments, a motor 2107 is configured to drive rotation of a first gear 2109 which in turn interferes with a second gear 2111 (positioned adjacent or on top of gear 2109), causing second gear 2111 to rotate. In some embodiments, rotation of second gear 2111 produces rotation of the assembly which includes the driving wheels 2103 and the linear motor 2105, rotating the assembly (along with guidewire held therein) in its entirety.

In some embodiments, when gear 2109 is rotated, it rotates a holder 2121 of the guidewire, rotating (rolling) the guidewire. Therefore, in some embodiments, rotation (roll) of the guidewire is carried out at two locations along the guidewire: a first location at holder 2121, and a second location at the assembly which includes the driving wheels and linear motor—which is rotated, along with the guidewire, as a whole. A potential advantage of rolling the guidewire at two locations along the guidewire, where optionally one location is proximal to the curve and the other is distal to the curve, may include reducing twisting of the guidewire during roll, for example by synchronized actuation of rotation at both locations, optionally by executing the roll movement of both sites by a single motor.

A potential advantage of driving rotation of the guidewire at two locations along the guidewire length using the same single motor (e.g. via motor 2107 which moves gear 2109) may include improved control over roll of the guidewire, for example as compared to driving rotation at the two (or more) locations using different motors, which may require synchronization between the motors direction and/or speed and/or actuation timing. Another potential advantage of using a same single motor for driving rotation at two different guidewire length locations may include providing for a more compact, smaller device housing.

Additionally or alternatively, rotation of gear 2109 does not rotate the guidewire directly (such as by not rotating holder 2121), and actuates rotation of the guidewire which starts only from the point of the assembly that is rotated by gear 2111 (as gear 2111 is rotated by gear 2109).

In some embodiments, one or more slip rings are used for supplying electrical current to the motors regardless of a current orientation (e.g. rotational orientation) of the assembly. For example, a slip ring constructed of a reel 2117 and base 2119 is located at the attachment of the second gear 2111 to the driving wheels and linear motor assembly. In some embodiments, the slip ring maintains an electrical coupling to the linear motor so that the linear motor may be actuated regardless of the rotational orientation of the assembly.

In another exemplary construction, shown in FIG. 21B, a motor which drives rotation and/or a gear 2113 which transmits rotation from the motor may directly interface with the assembly of the driving wheels and/or motor 2105 which drives linear movement and/or with a shaft in which the tool is received. In an example, gear 2113 is positioned along a similar long axis as the assembly.

In some embodiments, gear 2113 is formed with a slot 2123 through which the guidewire passes. Optionally, slot 2123 forms a direct extension of a slot 2125 in a designated shaft 2127 in which the guidewire is received. In some embodiments, the slot extends along a 5 degrees, 10 degrees, 20 degrees are of the gear circumference. A potential advantage of a slot through the gear may include that removal of the guidewire from the actuation mechanism may be facilitated.

FIG. 21C is a cross section view showing an actuation assembly comprising a shaft 2127 and wheels 2103 which drive linear movement of the guidewire. In some embodiments, shaft 2127 defines an elongate inner lumen 2129 in which guidewire is received, the lumen being in communication with slot 2125. In some embodiments, inner walls of shaft 2127 are constructed to match a contour of the wheels (see for example curvature 2128) so that a guidewire within lumen 2129 is guided right into (and then out from) a path in-between the wheels. In some embodiments, lumen 2129 extends in close proximity to the wheels outer contour, to bring the guidewire directly in-between the wheels.

In some embodiments, wheels 2103 are arranged (lie) on a plane that is substantially perpendicular to a plane defined by slot 2125.
Alternatively, the wheels may be arranged on a plane parallel to a plane defined by slot 2125.

A potential advantage of shaft constructed to match a contour of the wheels may include improved control of the guidewire as it is fed into (and exits out from) the path in between the driving wheels. Another potential advantage may include reducing a risk of slippage and/or other movement of the guidewire out of its designated path.

A potential advantage of an assembly which includes wheels for driving linear movement of the guidewire and which is configured to rotate, as a whole, to generate roll of the guidewire may include that linear movement can be performed during roll movement (or vice versa). Another potential advantage of a dual-movement assembly where linear movement and rotation are actuated at the same physical location (inside the robotic device) may include reducing slippage or other undesired guidewire movement which may occur, for example, if two spaced-apart mechanisms were each to drive linear movement and roll movement, and the guidewire would need to extend between them. In spaced apart mechanisms where one mechanism actuates rotation and another spaced-apart mechanism actuates linear movement, rotation of the guidewire may cause slippage of the guidewire between the rotation mechanism and the linear movement mechanism (or vice versa—linear movement of the guidewire may cause it to slip from the rotation mechanism). Another disadvantage of separate spaced apart mechanisms is the possible induction of friction at the idle site (i.e. the applying of friction onto a tool segment at a mechanism which is currently not in use), which may, require some type of release mechanism that would disengage one mechanism while the other is operated.

FIG. 22 shows an exemplary arrangement of mechanisms driving movement of a guidewire, according to some embodiments.

In some embodiments, guidewire rotation is carried out by more than one mechanism. Optionally, two or more mechanisms which engage the guidewire are configured to cause rotation (roll) of the guidewire. In such situation, the two mechanisms are controlled in a synchronized manner, for example to ensure that the guidewire is not twisted or kinked.

In some embodiments, a guidewire proximal portion or handle is held within an adaptor or holder 2201, suitable to generate rotation of the guidewire by either rotating to rotate the handle as a whole, and/or by actuating a handle component, such as a rotatable knob (not shown), which generates rotation (roll) of the guidewire (optionally, roll of a distal tip of the guidewire). The guidewire extends from the holder 2201 along an axis 2203 about which it rotates, until exiting the housing. When the guidewire renters the housing, it may be passed through a second mechanism suitable to actuate rotation (and in this example—linear movement as well). The second mechanism, for example a mechanism as shown in FIG. 21B, may be configured to actuate rotation (roll) of the guidewire about an axis 2205 along which the guidewire extends. Optionally, axis 2205 is parallel to axis 2203, defining parallel paths along which tool actuation takes place. Alternatively, paths of the tools defined along axes 2205 and 2203 are not parallel, for example, angling in or angling out relative to each other.

In some embodiments, the mechanisms extend to a similar height and/or axial length, so that they can be fitted within a compact housing.

FIGS. 23A-B are a schematic diagram and a flowchart pertaining to controlling a length and/or position of a tool by adjusting a curved portion of the tool, according to some embodiments.

In some embodiments, as schematically illustrated in FIG. 23A, a tool 2301 manipulated by the robotic device 2302 is engaged at two or more locations 2303, 2305 that are spaced apart from each other (along the length of the device), such that a segment 2307 of the tool extending in between the two locations can be adjusted (lengthened or shortened). In some embodiments, locations 2303, 2305 define attachment points of tool 2301 to the robotic device housing 2302, while segment 2307 extends externally to the device (i.e. externally to the device housing).

In some embodiments, locations 2303, 2305 are arranged relative to each other in a manner that causes a bend or curvature of the segment 2307, for example, into a "U" shape curvature as shown. In an example, locations 2303 and 2305 are aligned side-by-side.

Alternatively, locations 2303 and 2305 are not aligned side by side.

In some embodiments, for controlling a length of the tool, the curve (e.g. the "U" shape) is changed in size (e.g. expanded or contracted), changing a maximal distance 2309 between a peak of the curve and the housing of device 2302.

In some embodiments, an extent of the curve (e.g. as defined by a radius of curvature 2310) is set by linear movement of the tool (e.g. an extent in which the tool is advanced or retracted) and/or by manual loading of the tool, where a certain segment of the tool length is loaded into the system. In some embodiments, the extent of the curve depends on a total length of the tool.

In some embodiments, a distance 2312 between the attachment points of the tool to the housing is a function of the radius of curvature 2310 of the tool. Optionally, distance 2312 is twice the minimal radius of curvature to which the tool can be bent.

In some embodiments, dimensions of housing 2302 such as an extent of a wall of the housing in which the entry and exit apertures for the tool are formed is sized in accordance with the radius of curvature of the tool, for example being at least twice a minimal radius of curvature of the tool, but no more than 5 times, 6 times, 8 times, 10 times or intermediate, larger or smaller times the minimal radius of curvature of the tool intended for manipulation by the device.

In some embodiments, a maximal dimension of the housing (such as a width of the housing or a height of the housing) is between 5-10 cm, 8-20 cm, 12-40 cm or intermediate, longer or shorter.

In some embodiments, the device includes more than two engagement locations with the tool, allowing for a plurality of curves (e.g. "U" curves) to be formed in between the locations.

A potential advantage of a device that defines tool engagement locations such that a tool segment extending in between the locations is adjustable in length may include improving control over a length of the tool being manipulated. Optionally, a length of a most distal tool segment, such as a segment extending between the last exit from the robotic device housing and a target point inside the patient's body, is controlled, thereby potentially allowing fine control of a tool distal tip position. In some embodiments, advancing the tool towards the target point inside the body reduces the size of the curve of the tool outside the housing, and vice versa: retracting the tool back from the target point increases the size of the curve.

Another potential advantage of a device that defines tool engagement locations such that a tool segment extending in between the locations is adjustable in length may include the ability to receive and manipulate tools of various lengths.

Another potential advantage of a device that defines tool engagement locations such that a tool segment extending in between the locations is adjustable in length may include that the curved segment extends externally to the device housing, potentially allowing for a device of relatively small dimensions (e.g. axial length) which is substantially not affected by the tool length, enabling a compact housing of small dimensions.

The flowchart of FIG. 23B is an example of the mechanism described by the diagram of FIG. 23A. In some embodiments, a tool proximal end is secured to the robotic device (2321). For example, a handle of the tool is received by and/or attached to a designated adaptor or holder of the device. This attachment may be referred to as a first engagement location, for example as described above. In some embodiments, a more distal portion of the tool is threaded or inserted into the robotic device (2323). For example, a more distal portion of the tool is threaded into a designated shaft of the manipulating mechanism (e.g. a guidewire is inserted to be engaged by the tool-moving wheels). This second attachment may be referred to as the second engagement location, for example as described above.

Then, optionally, a tool segment extending in between the securing location of the tool proximal end and the engagement location of the tool (e.g. by the tool-moving wheels) is adjusted in length (2325).

FIG. 24 shows a system configuration defining an arrangement of tools in which a tool length can be adjusted, according to some embodiments.

In the example shown, a robotic device 2401 including and/or being coupled to a guiding catheter unit 2403 is configured to receive and drive movement of: a guidewire 2405, a microcatheter 2407, and a guiding catheter 2409. In some embodiments, as shown in this example, two "U" shaped curves 2411 and 2413 are defined by tools passed through the system: curve 2411 of the guidewire alone, and curve 2413 of the guidewire as it extends inside the lumen of the curved microcatheter. In some embodiments, a change in a size of curve 2413 results in joint movement of the microcatheter and guidewire at segments that are distal to the curve. In some embodiments, movement of the microcatheter (advancement or retraction) changes the size of curve 2413.

As can be observed in FIG. 24, the device housing 2402 (i.e. the walls of the housing) define the following apertures through which the tools pass into and/or out from of the inner device space defined by the housing: in some embodiments, a proximal end portion of guidewire 2405 is anchored at a holder 2404 to the device; the guidewire then enters the housing at an aperture 2406 and exits via an aperture 2408, where aperture 2408 is optionally located at an opposing wall of the housing to a wall in which aperture 2406 is defined. In some embodiments, a proximal portion of the microcatheter 2407 is anchored to the device at a holder 2410, where also the guidewire is received within the microcatheter lumen. Then, in some embodiments, the microcatheter enters the housing at an aperture 2412 and exits the housing at an aperture 2414, which is optionally configured at an opposite wall of the housing to aperture 2412.

FIG. 25 schematically illustrates tool-movement driving mechanisms of the system, according to some embodiments.

In some embodiments, as shown in this example, tool-movement mechanisms are arranged parallel to each other, for example, aligned side-by-side. A potential advantage of the tool moving mechanisms being parallel to each other (and optionally aligned along a similar axial extent) may include that a tool extending throughout the mechanisms can be adjustably bent, thus providing for variable tool length. A potential advantage of the tool moving mechanisms being parallel to each other (and optionally aligned along the a similar axial extent) may include that the device housing which accommodates these mechanisms can be maintained at relatively small, compact dimensions which are not determined by the tool actual length.

The tool-movement mechanisms shown herein include a mechanism 2501 for holding and optionally rotating a guidewire 2502 (see for example the description of FIG. 21A); a mechanism 2503 for actuating linear translation of the guidewire, including for example a set of wheels 2505; and a mechanism 2507 for actuating linear translation of a microcatheter 2508, including for example a set of wheels 2509.

In some embodiments, guidewire rotation may be carried out at one or both of mechanisms 2501, 2503, optionally under synchronization (such as a by a device controller).

FIGS. 26A-B are examples of a device configuration including elastic elements (e.g. springs) for selectively engaging tools received by the system, according to some embodiments.

In some embodiments, elastic elements (e.g. springs, bands) are positioned and configured to move (e.g. push) the driving wheels towards a tool received within the device, bringing the wheels into close contact with the tool. Additionally or alternatively, elastic elements are positioned and configured to move (e.g. push, center) a tool received within the device into operable contact with the driving wheels.

In the example shown, a spring 2601 is mounted onto a lever 2603 holding the driving wheels 2605 so that upon exertion of force onto the spring, the lever moves the wheels into contact with the tool. In some embodiments, force is exerted onto the spring by closure or movement of a portion of the housing, such as closure of a lid. In some embodiment, the spring is configured to retract the lever to move the wheels away from the tool, for example to allow for removal of the tool. Optionally, the spring is pulled on when the lid (or other portion of the housing) is opened or otherwise moved, thereby moving the wheels away from the tool.

In some embodiments, the spring is pre-configured to exert a force selected for a specific tool or tool size (e.g. tool diameter), for example, to position the wheels in contact with a tool of a certain thickness.

FIG. 27 is a schematic block diagram of a robotic device configured for manipulating two or more elongate surgical tools, according to some embodiments.

In some embodiments, walls of a housing 2701 of the robotic device define an inner volume 2703 in which at least two distinct pathways such as 2705, 2707 for the elongate surgical tools are defined. In some embodiments, the pathways extend across the inner volume, for example, between two opposing walls of the housing, such as wall 2709 and wall 2711. Optionally, the housing is shaped in an elongated form, for example having a substantially rectangular cross section profile, and the pathways extend along the length of the housing.

In some embodiments, each of the pathways extends between an entry aperture formed at the wall of the housing, and an exit aperture formed at an opposite wall of the housing. In the example shown, pathway 2705 extends between entry aperture 2713 formed at wall 2709 and an exit aperture 2715 formed at wall 2711; and pathway 2707 extends between an entry aperture 2717 formed at wall 2711 and an exit aperture 2719 formed at wall 2709.

In some embodiments, an aperture formed in a wall of the housing is shaped and/or sized according to the surgical tool that is passed through it. For example, a rounded (e.g. circular) aperture is sized for fitting a cylindrical tool, such as a guidewire or microcatheter, where the aperture diameter is optionally no more than 5%, 10%, 25% or intermediate, higher or smaller percentage larger than a diameter of the tool. In some embodiments, an aperture is sized for more than one tool to be passed through. Optionally, the aperture profile is oval (e.g. ellipsoid), rectangular, slot shaped and/or other. In some embodiments, a single elongated slot serves as an aperture for both inner pathways.

In some embodiments, a single tool passes through an entry aperture into the inner volume of the housing, and exits the housing through a respective exit aperture. Alternatively or additionally, in some embodiments, a plurality of tools telescopically arranged (e.g. 2 tools, such as a guidewire provided within the inner lumen of a microcatheter) pass together through the same entry aperture and exit the housing together through a respective exit aperture. Thus, in such an example, a first tool passes through a first inner pathway, exits the housing into the lumen of a second tool, and the telescopic assembly of both tools passes through a second inner pathway. In some embodiments, the telescopic arrangement of the tools occurs outside of the housing, after both tools have passed through their inner pathways, for example, in the case of a rapid exchange catheter which can be interfaced with the guidewire after each of the guidewire and the rapid exchange catheter have passed independently through their respective actuation assemblies located in the inner pathways.

In some embodiments, the pathways extend in a similar plane, for example, a similar horizontal plane, a similar vertical plane, a similar plane extending diagonally between the walls of the housing. In some embodiments, the pathways extend along parallel axes. A distance 2721 between the parallel axes may range, for example, between 3-12 cm, 2-10 cm, 5-9 cm or intermediate, longer or shorter distance.

Alternatively, in some embodiments, the pathways are not parallel, for example, one pathway extends directly between opposite walls while another takes a diagonal or other indirect route.

In some embodiments, except for the aperture locations, the housing is sealed. Optionally, the housing includes a removable or moveable cover or lid. In some embodiments, the housing is open at least in part, for example, shaped as a box with no top face.

In some embodiments, all components which engage the tool to manipulate it and/or to drive its movement are fully encased inside the inner volume of the housing and at least some of these components are positioned along the pathway defined for the tool. In some embodiments, these components include an actuation assembly, for example the tool-moving elements described in FIGS. 21B-C.

In some embodiments, as shown, a plurality of motors 2722, 2723 is configured to drive the actuation assemblies, for example configured to drive tool-moving elements 2725 (e.g. wheels) of each assembly. In some embodiments, the motor and the tool moving elements are positioned along the pathway defined for the tool. In some embodiments, the actuation assemblies of the two (or more) pathways are aligned side-by-side. A potential advantage of the actuation assemblies being aligned side-by side may include allowing for a short or minimal distance 2728 (optionally being the device width or height) between opposing walls 2733, 2735. In an example, distance 2728 is smaller than 15 cm, 12 cm, 10 cm or intermediate, longer or shorter distance.

In some embodiments, the actuation assemblies of the two or more pathways have a similar axial extent (or do not extend beyond a certain axial extent). A potential advantage of the actuation assemblies being positioned relative to each other and/or sized such that they do not extend beyond a certain axial extent may include that a distance 2730 between walls 2709 and 2711 (optionally being the device length) may be kept to a minimal axial extent needed to contain the movement driving components. In an example, distance 2730 is smaller than 10 cm, 7 cm, 12 cm or intermediate, longer or shorter distance. In some embodiments, the plurality of motors 2722, 2723 are also positioned within the axial extent of the actuation assemblies, and in proximity to the actuation assemblies, to facilitate the compact design of the device. The ability to position the motor(s) in close proximity to the actuation assemblies and potentially in contact with at least a portion of the actuation assemblies is provided, for example, due to that no barriers (e.g. sterile protection or shield) are needed between the actuation assembly, the motor(s), and the surgical tool being manipulated.

In some embodiments, the actuation assemblies of the two or more pathways are positioned within the same, shared inner volume defined by the walls of the housing. In some embodiments, no barriers (e.g. inner walls, shields, drapes, and the like) exist between the movement driving components of the two or more pathways. In some embodiments, no barriers (e.g. inner walls, shields, drapes, and the like) exist between the actuation assemblies and the tools that are being manipulated by them.

Alternatively, in some embodiments, a partial partition or barrier are provided. For example, the device housing may include an inner wall or protrusion which do not fully block the inner volume, leaving at least some regions of the pathways in communication with each other.

In some embodiments, an actuation assembly of an inner pathway (e.g. an actuation assembly that includes a shaft in which a tool is received and/or wheels which drive linear movement of the tool) is exposed to an actuation assembly of a different inner pathway, for example an adjacent pathway.

In some embodiments, actuation assemblies of a plurality of pathways are arranged and held with respect to each other on a chassis. Optionally, the chassis is exposed and open to its surroundings, for example, no housing is provided.

In some embodiments, an actuation assembly of a pathway at least partially restrict movement of the tool within the inner pathway, for example, restricting lateral movement of a tool received within the pathway. For example, movement of the tool out of notional limits defined by the elongate pathway is restricted. In some embodiments, the tool is channeled through the pathway, for example, received within a slot of an elongate shaft (such as the shaft of an actuation assembly, e.g. shaft 2127, FIG. 21B). Alternatively or additionally, the pathway is defined by a path generated between a plurality of pairs of opposing wheels.

In some embodiments, in addition to extending through the pathway, a tool engages the device at one or more additional fixation locations (also referred to herein as "securing points", "engagement points"). In some embodiments, a fixation location comprises a holder (such as 2727, 2729) located outside the housing, inside the housing, or partially inside the housing and partially outside the housing. In some embodiments, a fixation location couples a tool to the housing and/or to one or more other tools. For example, at fixation location 2729 a first elongate surgical tool 2731 which extends through pathway 2705 (e.g. a guidewire) enters an inner lumen of a second elongate surgical tool 2733 (e.g. a microcatheter), which is coupled to the housing at fixation location 2729. In some embodiments, a proximal end of tool 2731 is coupled to the housing at fixation location 2727.

In some embodiments, fixation location 2727 is shaped and configured to accommodate a proximal handle of tool 2731, for example, a handle that manipulates the distal portion of the tool in terms of bend and/or stiffness. In some embodiments, an additional motor (not shown) is configured for rotating tool 2731 through two locations, one of which is the handle of the tool (for example at fixation location 2727) and the other is a region more distal of the tool. For example, a motor configured for rotating tool 2731 by rotating an actuation assembly which is associated with a portion of the tool 2731, is also operably connected to the handle of the tool, optionally through a gear system. As such, the motor is configured for rotating the tool simultaneously from these two distinct locations. An advantage for commencing roll movement by the same motor in two different locations along the tool may include enhancing the torque applied on the tool and eliminating the risk of slippage of the tool in its gripping locations found in the actuation assembly.

In some embodiments, a fixation location of a tool with the housing (such as 2727) and an entry aperture leading the tool into the inner volume (such as 2713) are located on a same wall of the housing, so that a section of the tool that is found outside the housing forms a curve, for example, a U-shaped curve. In some embodiments, for example as described in FIGS. 23A-B, the extent of the U-curve is dynamically adjustable. Optionally, linearly moving the tool (such as via the tool-moving elements, e.g. wheels) changes the extent of the U-curve relative to the external side of the wall of the housing.

In some embodiments, the curve is defined along a path which extends from and to the same wall of the device housing.

In the example shown, the housing comprises sharp corners and straight edge walls, but other configurations are also contemplated, including, for example, rounded corners, curved walls, and the like.

In some embodiments, actuation of the actuation assembly (e.g. via a motor) of each of the pathways is controlled by a controller 2735. In some embodiments, components of each pathway are controlled independently, yet in a synchronized manner.

In some embodiments, controller 2735 is controlled remotely by an external device, for example by a remote control device such as described herein.

FIG. 28 schematically illustrates a robotic device for manipulation of two or more elongate surgical tools configured for a telescopic arrangement, such as in a non-limiting manner a guidewire and a microcatheter, the first elongate tool extending at least in part within the lumen of the second elongate tool, according to some embodiments.

In some embodiments, robotic device 2801 comprises a housing 2803 comprised of a plurality of walls which form an inner volume 2805 between them. In some embodiments, two or more inner pathways extend inside the inner volume, such that tools 2810, 2813 received and operated by the device extend, at least in part, along the inner pathways.

In some embodiments, each of the inner pathways includes an actuation assembly positioned at a position of the pathway, for example, axially extending along at least a portion of the pathway. In some embodiments, an actuation assembly, such as 2806, 2807, is configured for linearly moving the tool, for example, one or more sets of wheels configured to advance and/or retract the tool. Alternatively or additionally, an actuation assembly, such as 2806, is configured for moving the tool in a roll manner, for example by rotating a set of wheels gripping the tool therebetween.

In some embodiments, actuation assemblies are operably coupled to a plurality of motors, for example motors 2811, 2808, 2809. In some embodiments, the motors are configured for operating the actuation assemblies to generate linear movement of the tools received therein. Alternatively or additionally, the motors are configured to generate a roll movement of the received tool, optionally by generating a roll movement of the tool's associated actuation assembly as a whole. For example, motor 2809 is operably connected to linear movement mechanism 2807, optionally via a gear system, and is configured to rotate linear movement mechanism 2807 together with motor 2811, thereby rolling tool 2810 which is gripped within linear movement mechanism 2807. A potential advantage for rotating the entire linear movement mechanism along with the tool is a simplification of the associated gear system, and the enablement of simultaneous operation of linear and roll movement together. Rolling of motor 2811 together with the linear movement mechanism 2806 is enabled, in some embodiments, due to that no sterile barrier exists between the motors and the actuation assemblies.

In the example shown, a first elongate surgical tool 2810 (e.g. a guidewire) extends along a first inner pathway, for example between an entry aperture 2814 into the housing and an exit aperture 2816 from the housing.

In some embodiments, linear movement of tool 2810 is driven by motor 2811, and roll of tool 2810 is driven by motor 2809, both located and configured at a position of the inner pathway (e.g. along a notional axis defined by the pathway across the inner volume).

In some embodiments, at the exit aperture 2816 of tool 2810 from the housing, the tool 2810 is telescopically received within a lumen of a second elongate surgical tool

2813, for example, a microcatheter. Tool 2813, in turn, enters the housing at an entry aperture 2815 and extends along a second inner pathway to an exit aperture 2817, with tool 2810 extending inside it.

In some embodiments, linear movement of the tool 2813 is driven by actuation assembly 2807.

In some embodiments, the actuation mechanism(s) and the plurality of motors all share the same inner volume, with no barrier or other physical separation therebetween.

FIG. 29 schematically illustrates another exemplary embodiment of the robotic device configured for receiving three telescopically arranged elongate surgical tools, for example, a guidewire, a microcatheter and a guiding catheter.

In some embodiments, robotic device 2901 comprises a housing 2903 having an inner volume 2905, wherein entry aperture 2914 and exit aperture 2916 define, between them, a first inner pathway for receiving a first elongated surgical tool 2910, and entry aperture 2915 and exit aperture 2917 define, between them, a second inner pathway for receiving a second elongate surgical tool 2913.

In some embodiments, actuation assemblies 2906, 2907 are positioned along the inner pathways and configured to come into contact with the tools received therein for at least one of advance, retract and/or roll the tool. In some embodiments, a plurality of motors, such as motors 2909, 2911 and 2908, are positioned in proximity to the inner pathways and are operably connected to the actuation assemblies. In some embodiments, the motors and the actuation assemblies are found within the same inner volume accommodating the inner pathways, for example without barriers blocking the air circulating between them.

In some embodiments, only one motor is operably connected to an actuation assembly, as exemplified by actuation assembly 2907 and motor 2908, which is operably connected to the actuation assembly to advance or retract elongate surgical tool 2913. In some embodiments, two or more motors are operably connected to an actuation assembly, as exemplified by actuation assembly 2906 and motors 2909 and 2911. In this example, motors 2909 and 2911 are operably connected to actuation assembly 2906 to advance, retract and roll elongate surgical tool 2910. Optionally, motor 2909 rolls tool 2910 by rolling the complex 2904, wherein complex 2904 comprises at least actuation assembly 2906 and motor 2911.

In some embodiments, the proximal end of elongate surgical tool 2910 is secured to a fixation location 2920. In some embodiments, fixation location 2920 includes a protrusion configured to attach to a luer (not shown) optionally found in the proximal end of tool 2910. Alternatively, fixation location 2920 comprises a cavity sized and shaped to accommodate a handle (not shown) optionally found at the proximal end of tool 2910. In some embodiments, the proximal end of tool 2910 is operably connected to adaptor 2950 which, in some embodiments, causes the tool to roll around its longitudinal axis, for example by roll of a proximal handle portion of the tool which is received at the adaptor. In some embodiments, the motor which is operably connected to the adaptor to induce the roll movement, is the same motor operably connected to the actuation assembly associated with the tool at a more distal location. For example, as shown and exemplified through motor 2909, which is operably connected to adaptor 2905 and at the same time operably connected to complex 2904, to cause roll actuation of tool 2910 from at least these two distinct locations.

In some embodiments, a U-shape curve is formed in tool 2910 between fixation location 2920 and entry aperture 2914. In some embodiments, when tool 2910 is moved linearly in actuation assembly 2906 it causes the distal end 2930 of tool 2910 to advance or retract, optionally, when a distal portion has been introduced into the patient's body. In some embodiments, as tool 2910 is advanced or retracted, a distance between a maximal point of the U-shape curve and housing 2903 is shortened or lengthened. An advantage of the U-shape curve being formed outside of housing 2903 is that the housing size does not need to accommodate this distance, and the device is capable of navigating a range of tool lengths, with no dependency on the size of the device.

In some embodiments, a fixation location of one elongate surgical tool is found at the exit aperture of another elongate surgical tool, as shown and exemplified in fixation point 2922, which overlaps with exit aperture 2916, and as such, causes elongate surgical tool 2910 to exit housing 2903 through exit aperture 2916 directly into the lumen of elongate surgical tool 2913, when tool 2913 is connected to fixation location 2922.

In some embodiments, a second U-shaped curve for tool 2910 and a first U-shaped curve for tool 2913 are formed between fixation location 2922 and entry aperture 2915. In some embodiments, when advancing or retracting the distal end 2940 of tool 2913, both tool 2910 and tool 2913 are moved to lengthen or shorten the distance between the maximal point of the joint curve and housing 2903. In some embodiments, when it is desired to linearly translate the distal end 2940 (of tool 2913) without translating distal end 2930 (of tool 2910), motor 2911 linearly translates tool 2910 at an opposite direction to the translation of motor 2907 which affects both tools, thereby, causing the distal end 2930 of tool 2910 to effectively to stand in place.

In some embodiments, an elongate surgical tool (for example, a guide catheter, or sheath) connected to a fixation location from outside of housing 2903 is configured to be operated by motors residing inside housing 2903, for example, elongate surgical tool 2919 connected to fixation location 2917 and can be linearly moved actuation assembly 2927, operably connected to motor 2928 and motor 2929 for linear and roll movement, respectively. In some embodiments, actuation assembly 2927 together with motors 2928 and 2929 all reside in the same inner volume as motors 2909, 2911 and 2908 and in the same inner volume as the actuation assemblies they are operably connected to, 2906 and 2907. In such exemplary embodiments, at least 5 motors reside within the same inner volume as the inner pathways of the elongate surgical tools 2910 and 2913.

In some embodiments, fixation location 2924 overlaps with exit aperture 2917, such that the telescopically arranged elongate surgical tools 2910 and 2913 exit housing 2903 through exit aperture 2917, directly into the lumen of elongate surgical tool 2919. In some embodiments, actuation assembly 2927 is positioned along the same inner pathway as that of tool 2913.

As used herein, the terms "insertion device" and "medical device", "robotic device", "robotic system", "device", "system" and the like may interchangeably be used. In some instances, a device is addressed as part of a system.

As used herein, the terms "medical instrument" and "medical tool", "surgical tool", "elongate tool" and the like may interchangeably be used.

Although some examples described throughout this disclosure mainly relate to insertion of a guidewire into the patient's blood vessel, this is done for simplicity reasons alone, and the scope of this disclosure is not limited to devices for insertion of guidewires alone, but may include insertion of additional medical tools/instruments, such as, microcatheters, balloon catheters, etc. Further, the scope of this disclosure is not limited to insertion of medical tools into blood vessels, but it may include insertion of medical tools into other bodily lumens, such as the urethra, gastrointestinal tract and the trachea. In the description and claims of the application, the words "include" and "have", and forms thereof, are not limited to members in a list with which the words may be associated.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A compact robotic device for driving movement of two or more elongate surgical tools when said two or more elongate surgical tools are at least partially received within said device, said device comprising:
    a housing comprising walls which define an inner volume including at least two inner pathways for accommodating said two or more elongate surgical tools;
    said housing encasing:
        a plurality of motors;
        two or more tool actuation assemblies, each of said two or more actuation assemblies configured at a position of one of said two or more inner pathways; each of said two or more actuation assemblies driven by at least one of said plurality of motors, each of said two or more actuation assemblies configured to operably contact an elongate surgical tool of said two or more elongate surgical tools which is at least partially received in one of the two or more inner pathways to at least one of advance, retract and/or roll said respective elongate surgical tool;
    wherein at least one fixation location is defined at said walls of said housing, externally to said inner volume; said fixation location including a holder which secures a proximal end of at least one of said two or more elongate surgical tools to the housing while a more distal segment of said at least one elongate surgical tool is received inside the housing within one of said two or more inner pathways.

2. The device according to claim 1, wherein each of said two or more inner pathways extends across said inner volume between an entry aperture and an exit aperture, said entry aperture and said exit aperture being configured on opposite walls of said device housing and in communication with said inner volume.

3. The device according to claim 2, wherein said at least one fixation location is located at one of said exit apertures, such that the elongate surgical tool exiting said inner volume through said exit aperture is led into a lumen of a proximal end of a second elongate surgical tool of said two or more elongate surgical tools, forming a telescopic arrangement of the two elongate surgical tools.

4. The device according to claim 2, wherein said at least one fixation location and one of said at least two entry apertures are defined along the same wall of the housing such that the elongate surgical tool secured to said device at said at least one fixation location forms a curve before entering said inner volume through said at least one entry aperture.

5. The device according to claim 2, wherein said housing, at at least one of said entry apertures and/or at at least one of said exit apertures, comprises a conically shaped protrusion having a rounded external lip.

6. The device according to claim 1, wherein no inner barrier exists between said two or more inner pathways such that said two or more tool actuation assemblies and said plurality of motors all share said inner volume with no separation therebetween.

7. The device according to claim 6, wherein said plurality of motors comprises 3-5 motors.

8. The device according to claim 1, wherein said two or more inner pathways are parallel to each other and have a similar axial extent.

9. The device according to claim 1, wherein a distance between long axes of said inner pathways is shorter than 10 cm.

10. The device according to claim 1, wherein said tool actuation assemblies are both confined within said walls of said housing, and wherein only portions of said two or more elongate surgical tools, when received within said device, extend outwardly from said walls of said housing to a distance of at least 1 cm away from said housing.

11. The device according to claim 1, wherein said inner volume is smaller than 2800 cm^3 and wherein said device has a weight of less than 850 grams.

12. The device according to claim 1, wherein each of said actuation assemblies comprises a plurality of wheel pairs, each wheel pair comprising a set of opposing wheels arranged to define said inner pathway therebetween.

13. The device according to claim 1, wherein dimensions of said housing include a height shorter than 30 cm, a width shorter than 30 cm, a length shorter than 30 cm; wherein each of said two or more inner pathways extends axially along said length.

14. The device according to claim 1, wherein said housing comprises a removable or movable cover providing access to said two or more elongate surgical tools loaded onto said device and extending along at least a portion of said inner pathways.

15. The device according to claim 1, wherein said two or more elongate surgical tools include a guidewire and a microcatheter, the guidewire configured to at least partially extend through a lumen of said microcatheter.

16. The device according to claim 1, comprising a controller configured to control said plurality of motors for driving said two or more actuation assemblies.

17. The device according to claim 16, wherein said controller is controlled remotely by an external remote control device.

18. The device according to claim 1, wherein said at least one fixation location defines a cavity shaped and configured to accommodate a proximal handle of said at least one elongate surgical tool.

19. The device according to claim 1, wherein said holder comprises a luer.

20. The device according to claim 1, wherein said holder is configured to provide for roll of said respective elongate surgical tool about a long axis of said tool.

21. A kit comprising:
a device according to claim 1;
a guidewire for loading onto said device such that at least a portion of said guidewire extends along one of said two or more inner pathways;
a microcatheter for loading onto said device such that at least a portion of said microcatheter extends along a second of said two or more inner pathways.

22. A surgical system comprising:
a robotic device according to claim 1;
an add-on unit for driving movement of a guiding catheter, said add-on unit mechanically attachable to said housing of said robotic device.

* * * * *